United States Patent
Lee et al.

(10) Patent No.: US 12,410,130 B2
(45) Date of Patent: Sep. 9, 2025

(54) LIGHT-EMITTING DEVICE AND ELECTRONIC APPARATUS INCLUDING THE SAME

(71) Applicant: Samsung Display Co., Ltd., Yongin-si (KR)

(72) Inventors: Daewoong Lee, Yongin-si (KR); Hyomin Ko, Yongin-si (KR); Bora Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 704 days.

(21) Appl. No.: 17/450,175

(22) Filed: Oct. 7, 2021

(65) Prior Publication Data

US 2022/0285619 A1   Sep. 8, 2022

(30) Foreign Application Priority Data

Feb. 26, 2021 (KR) .................. 10-2021-0026473

(51) Int. Cl.
  *H10K 85/60*    (2023.01)
  *C07C 211/61*   (2006.01)
  *C07D 209/86*   (2006.01)
  *C09K 11/06*    (2006.01)
  *H10K 50/15*    (2023.01)
  *H10K 50/17*    (2023.01)
  *H10K 50/19*    (2023.01)
  *H10K 102/00*   (2023.01)

(52) U.S. Cl.
  CPC .......... *C07D 209/86* (2013.01); *C07C 211/61* (2013.01); *C09K 11/06* (2013.01); *H10K 85/633* (2023.02); *H10K 85/636* (2023.02); *C07C 2601/14* (2017.05); *C07C 2603/18* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *H10K 50/15* (2023.02); *H10K 50/17* (2023.02); *H10K 50/19* (2023.02); *H10K 85/615* (2023.02); *H10K 85/624* (2023.02); *H10K 85/6572* (2023.02); *H10K 2102/351* (2023.02)

(58) Field of Classification Search
None
See application file for complete search history.

(56) References Cited

U.S. PATENT DOCUMENTS

| | | |
|---|---|---|
| 10,916,593 B2 | 2/2021 | Kashiwabara et al. |
| 2019/0123291 A1 | 4/2019 | Jeon et al. |
| 2021/0005814 A1* | 1/2021 | Watabe ............ H10K 85/631 |
| 2021/0036226 A1 | 2/2021 | Osaka et al. |
| 2022/0204438 A1* | 6/2022 | Kubota ............ C09K 11/06 |

FOREIGN PATENT DOCUMENTS

| | | |
|---|---|---|
| CN | 109755400 A | 5/2019 |
| JP | 2005-272805 A | 10/2005 |
| JP | 3801330 B2 | 7/2006 |
| KR | 10-2006-0079225 A | 7/2006 |
| KR | 10-2011-0022605 A | 3/2011 |
| KR | 10-2019-0044148 A | 4/2019 |
| KR | 10-2021-0004874 | 1/2021 |
| WO | WO-2019220276 A1 * | 11/2019 ........... C07C 211/54 |

* cited by examiner

*Primary Examiner* — Robert S Loewe
(74) *Attorney, Agent, or Firm* — Womble Bond Dickinson (US) LLP

(57) ABSTRACT

Provided are a light-emitting device and an electronic apparatus including the same. The light-emitting device includes: an anode; a cathode; an interlayer including an emission layer between the anode and the cathode; and a hole transport region between the anode and the emission layer, wherein the hole transport region includes a first layer and a second layer, the first layer is between the anode and the second layer, the first layer includes a first compound represented by Formula 1, the second layer includes a second compound, and a charge mobility of the first compound is lower than a charge mobility of the second compound.

17 Claims, 5 Drawing Sheets

| 150 |
|-----|
| 130 |
| 110 |

LIGHT-EMITTING DEVICE AND ELECTRONIC APPARATUS INCLUDING THE SAME

CROSS-REFERENCE TO RELATED APPLICATION

This application claims priority and the benefit of Korean Patent Application No. 10-2021-0026473, filed on Feb. 26, 2021, in the Korean Intellectual Property Office, the entire contents of which are hereby incorporated by reference.

BACKGROUND

1. Field

One or more embodiments of the present disclosure relate to a light-emitting device and an electronic apparatus including the same.

2. Description of the Related Art

Light-emitting devices are self-emissive devices that, as compared with devices of the related art, have wide viewing angles, high contrast ratios, short response times, and excellent characteristics in terms of luminance, driving voltage, and response speed, and produce full-color images.

In a light-emitting device, a first electrode is on a substrate, and a hole transport region, an emission layer, an electron transport region, and a cathode are sequentially formed on the first electrode. Holes provided from the first electrode may move toward the emission layer through the hole transport region, and electrons provided from the cathode may move toward the emission layer through the electron transport region. Carriers, such as holes and electrons, recombine in the emission layer to produce excitons. These excitons transition (e.g., relax) from an excited state to a ground state to thereby generate light.

For example, in order to provide a light-emitting device having a high resolution, distances between neighboring subpixels are gradually getting shorter. In this regard, efforts have been made to reduce current loss in the lateral direction which flows into a neighboring subpixel.

SUMMARY

Provided are a light-emitting device including certain compounds in a hole transport region and an electronic apparatus including the light-emitting device.

Additional aspects of one or more embodiments will be set forth in part in the description, which follows and, in part, will be apparent from the description, or may be learned by practice of the presented embodiments of the disclosure.

An aspect of one or more embodiments of the present disclosure provides a light-emitting device including an anode, a cathode, an interlayer including an emission layer between the anode and the cathode, and a hole transport region between the anode and the emission layer,
wherein the hole transport region includes a first layer and a second layer,
the first layer is between the anode and the second layer,
the first layer includes a first compound represented by Formula 1,
the second layer includes a second compound, and
a charge mobility of the first compound is lower than a charge mobility of the second compound.

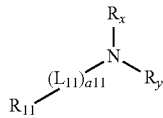

Formula 1

In Formula 1,
$L_{11}$ may be a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$,
a11 may be an integer from 0 to 5,
$R_{11}$ may be a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, or a monovalent non-aromatic condensed heteropolycyclic group unsubstituted or substituted with at least one $R_{10a}$,
$R_x$ and $R_y$ may each be a group represented by Formula 2, and $R_x$ and $R_y$ may be identical to each other,

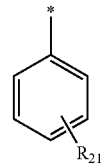

Formula 2 wherein, in Formula 2,
$R_{21}$ may be a cyclopentyl group, a cyclohexyl group, a tert-butyl group, or a $C_5$-$C_{10}$ alkyl group, and
$R_{10a}$ may be:
deuterium (-D), —F, —Cl, —Br, —I, a hydroxyl group, a cyano group, or a nitro group,
a $C_1$-$C_{60}$ alkyl group, a $C_2$-$C_{60}$ alkenyl group, a $C_2$-$C_{60}$ alkynyl group, or a $C_1$-$C_6$ alkoxy group, each unsubstituted or substituted with -D, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —C($Q_{11}$)($Q_{12}$)($Q_{13}$), —B($Q_{11}$)($Q_{12}$), —N($Q_{11}$)($Q_{12}$), —P($Q_{11}$)($Q_{12}$), —C(=O)($Q_{11}$), —S(=O)($Q_{11}$), —S(=O)$_2$($Q_{11}$), —P(=O)($Q_{11}$)($Q_{12}$), —P(=S)($Q_{11}$)($Q_{12}$), or any combination thereof,
a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with -D, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —C($Q_{21}$)($Q_{22}$)($Q_{23}$), —B($Q_{21}$)($Q_{22}$), —N($Q_{21}$)($Q_{22}$), —P($Q_{21}$)($Q_{22}$), —C(=O)($Q_{21}$), —S(=O)($Q_{21}$), —S(=O)$_2$($Q_{21}$), —P(=O)($Q_{21}$)($Q_{22}$) or —P(=S)($Q_{21}$)($Q_{22}$), or any combination thereof, or —Si($Q_{31}$)($Q_{32}$)($Q_{33}$), —C($Q_{31}$)($Q_{32}$)($Q_{33}$), —B($Q_{31}$)($Q_{32}$), —N($Q_{31}$)($Q_{32}$), —P($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), or —P(=S)($Q_{31}$)($Q_{32}$), wherein $Q_{11}$ to $Q_{13}$, $Q_{21}$ to $Q_{23}$, and $Q_{31}$ to $Q_{33}$ may each independently be hydrogen, -D, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, or a $C_3$-$C_{60}$ carbocyclic group or a $C_1$-$C_{60}$ heterocyclic group, each unsubstituted or substituted with -D, —F, a cyano group, a $C_1$-$C_{60}$ alkyl group, a $C_1$-$C_{60}$ alkoxy group, a phenyl group, a biphenyl group, or any combination thereof, and

* indicates a binding site to a neighboring atom.

Another aspect of one or more embodiments of the present disclosure provides a light-emitting device including a substrate partitioned into a first subpixel area, a second subpixel area, and a third subpixel area, a plurality of anodes respectively in the first subpixel area, the second subpixel area, and the third subpixel area of the substrate, a cathode facing the plurality of anodes, and an interlayer including an emission layer and a hole transport region, the emission layer being between the plurality of anodes and the cathode, and the hole transport region being between the plurality of anodes and the emission layer, wherein the hole transport region includes a first layer and a second layer, the first layer is between the plurality of anodes and the second layer, the first layer includes a first compound represented by Formula 1, the second layer includes a second compound, and a charge mobility of the first compound is lower than a charge mobility of the second compound.

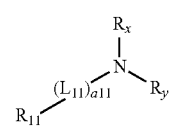

Formula 1

In Formula 1, $L_{11}$ may be a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$, a11 may be an integer from 0 to 5, $R_{11}$ may be a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, or a monovalent non-aromatic condensed heteropolycyclic group unsubstituted or substituted with at least one $R_{10a}$, $R_x$ and $R_y$ may each be a group represented by Formula 2, and $R_x$ and $R_y$ may be identical to each other,

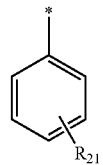

Formula 2 wherein, in Formula 2, $R_{21}$ may be a cyclopentyl group, a cyclohexyl group, a tert-butyl group, or a $C_5$-$C_{10}$ alkyl group, and $R_{10a}$ may be:

deuterium (-D), —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with -D, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —C($Q_{11}$)($Q_{12}$)($Q_{13}$), —B($Q_{11}$)($Q_{12}$), —N($Q_{11}$)($Q_{12}$), —P($Q_{11}$)($Q_{12}$), —C(=O)($Q_{11}$), —S(=O)($Q_{11}$), —S(=O)$_2$($Q_{11}$), —P(=O)($Q_{11}$)($Q_{12}$), —P(=S)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with -D, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —C($Q_{21}$)($Q_{22}$)($Q_{23}$), —B($Q_{21}$)($Q_{22}$), —N($Q_{21}$)($Q_{22}$), —P($Q_{21}$)($Q_{22}$), —C(=O)($Q_{21}$), —S(=O)($Q_{21}$), —S(=O)$_2$($Q_{21}$), —P(=O)($Q_{21}$)($Q_{22}$) or —P(=S)($Q_{21}$)($Q_{22}$), or any combination thereof, or —Si($Q_{31}$)($Q_{32}$)($Q_{33}$), —C($Q_{31}$)($Q_{32}$)($Q_{33}$), —B($Q_{31}$)($Q_{32}$), —N($Q_{31}$)($Q_{32}$), —P($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), or —P(=S)($Q_{31}$)($Q_{32}$), wherein $Q_{11}$ to $Q_{13}$, $Q_{21}$ to $Q_{23}$, and $Q_{31}$ to $Q_{33}$ may each independently be hydrogen, -D, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, or a $C_3$-$C_{60}$ carbocyclic group or a $C_1$-$C_{60}$ heterocyclic group, each unsubstituted or substituted with -D, —F, a cyano group, a $C_1$-$C_{60}$ alkyl group, a $C_1$-$C_{60}$ alkoxy group, a phenyl group, a biphenyl group, or any combination thereof, and

* indicates a binding site to a neighboring atom.

Another aspect of one or more embodiments of the present disclosure provides an electronic apparatus including the light-emitting device as described above and a thin-film transistor, wherein the thin-film transistor includes a source electrode and a drain electrode, and the anode of the light-emitting device is electrically coupled to at least one selected from the source electrode and the drain electrode of the thin-film transistor.

BRIEF DESCRIPTION OF THE DRAWINGS

The above and other aspects and features of certain embodiments of the disclosure will be more apparent from the following description taken in conjunction with the accompanying drawings, in which:

FIG. 1 is a schematic view of a light-emitting device according to an embodiment;

DETAILED DESCRIPTION

Figure 2:
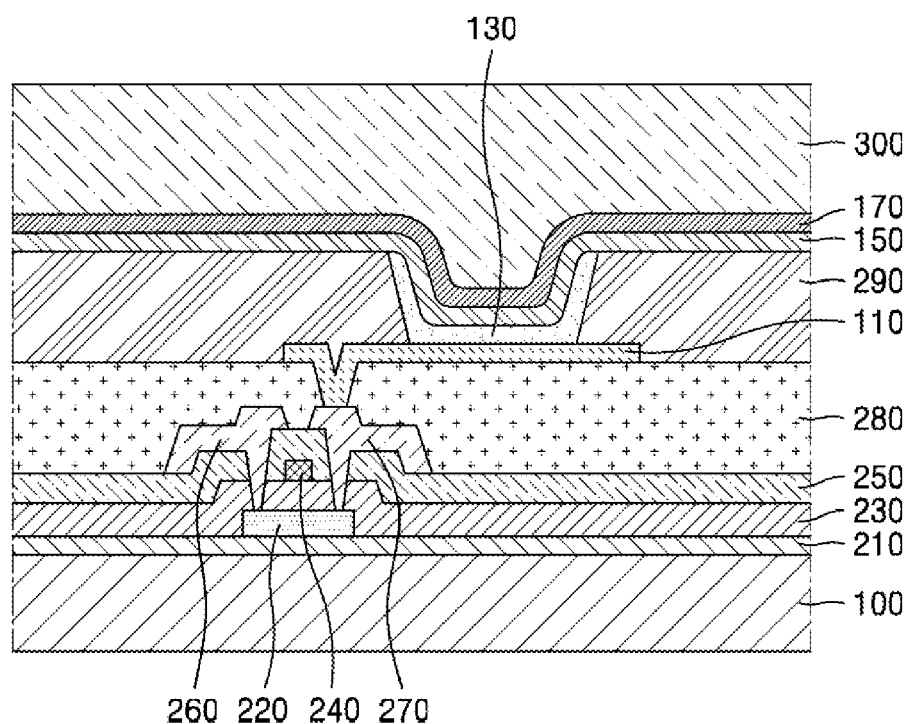
FIG. 2 is a schematic view of a light-emitting apparatus according to an embodiment.

Reference will now be made in more detail to embodiments, examples of which are illustrated in the accompanying drawings, wherein like reference numerals refer to like elements throughout the specification. In this regard, the present embodiments may have different forms and should not be construed as being limited to the descriptions set forth herein. Accordingly, the embodiments are merely described below, by referring to the figures, to explain aspects of one or more embodiments of the present description. As used herein, the term "and/or" includes any and all combinations of one or more of the associated listed items. Throughout the disclosure, the expression "at least one of a, b, or c" indicates only a, only b, only c, both a and b, both a and c, both b and c, all of a, b, and c, or variations thereof.

Because the present disclosure may have diverse modified embodiments, only certain embodiments are illustrated in the drawings and are described in the detailed description. An effect and a characteristic of the disclosure, and a method of accomplishing these will be apparent when referring to embodiments described with reference to the drawings. The present disclosure may, however, be embodied in many different forms and should not be construed as limited to the embodiments set forth herein.

One or more embodiments of the present disclosure will be described below in more detail with reference to the accompanying drawings. Those components that are the same or are in correspondence with each other are identified with the same reference numeral regardless of the figure number, and redundant explanations thereof are generally not repeated.

As used herein, an expression used in the singular encompasses the expression of the plural, unless it has a clearly different meaning in the context.

It will be further understood that the terms "comprises" and/or "comprising," as used herein, specify the presence of stated features or elements, but do not preclude the presence or addition of one or more other features or elements.

It will be understood that when a layer, region, or component is referred to as being "on" or "onto" another layer, region, or component, it may be directly or indirectly formed on the other layer, region, or component. For example, intervening layers, regions, or components may be present.

Sizes of elements in the drawings may be exaggerated for convenience of explanation. In other words, because sizes and thicknesses of components in the drawings may be arbitrarily illustrated for convenience of explanation, the following embodiments are not limited thereto.

The term "interlayer," as used herein, refers to a single layer and/or all of a plurality of layers between an anode and a cathode of a light-emitting device.

A light-emitting device according to an embodiment of the present disclosure includes: an anode; a cathode; an interlayer including an emission layer between the anode and the cathode; and a hole transport region between the anode and the emission layer, wherein the hole transport region includes a first layer and a second layer, the first layer is between the anode and the second layer, the first layer includes a first compound represented by Formula 1, the second layer includes a second compound, and a charge mobility of the first compound is lower than a charge mobility of the second compound:

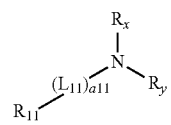

Formula 1 wherein, in Formula 1, $L_{11}$ may be a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$, a11 may be an integer from 0 to 5, $R_{11}$ may be a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, or a monovalent non-aromatic condensed heteropolycyclic group unsubstituted or substituted with at least one $R_{10a}$, $R_x$ and $R_y$ may each be a group represented by Formula 2, and $R_x$ and $R_y$ may be identical to each other,

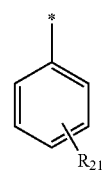

Formula 2 wherein, in Formula 2, $R_{21}$ may be a cyclopentyl group, a cyclohexyl group, a tert-butyl group, or a $C_5$-$C_{10}$ alkyl group, and

* indicates a binding site to a neighboring atom.

In an embodiment, the first compound and the second compound may be different from each other.

In the light-emitting device, the charge mobility of the first compound and the charge mobility of the second compound may be adjusted, so that a light-emitting device having reduced lateral current loss without (or substantially without) an increase in driving voltage may be provided.

In more detail, the charge mobility of the first compound may be $1 \times 10^{-6}$ cm$^2$/Vs or more. When the charge mobility of the first compound is adjusted to be in the range described above, a driving voltage of a light-emitting device may be low.

In more detail, the charge mobility of the first compound may be from about $5\times10^{-6}$ cm$^2$/Vs to about $5\times10^{-5}$ cm$^2$/Vs, and the charge mobility of the second compound may be from about $1\times10^{-4}$ cm$^2$V/s to about $9\times10^{-4}$ cm$^2$V/s.

In an embodiment, a thickness of the first layer may be 30 nm or less, for example, 20 nm or less, for example, 15 nm or less. When the ranges described above are satisfied, a light-emitting device having a low driving voltage may be provided.

In an embodiment, the first layer may further include a charge-generation material. For example, when the first layer further includes a charge-generation material, lateral current loss may be relatively improved. Accordingly, the effect of reducing the lateral current loss may be increased when the first layer further includes the charge-generation material. The charge-generation material will be described in more detail herein below.

Because $R_x$ and $R_y$ in the first compound are identical to each other, certain charge mobility characteristics may be satisfied. For example, the first compound may have a charge mobility of $1\times10^{-6}$ cm$^2$/Vs or more. As a result, a driving voltage of a light-emitting device including the first compound may be reduced.

Because $R_x$ and $R_y$ in the first compound each include $R_{21}$ which is a substituent having a large steric hindrance, the charge mobility of the first compound may be relatively low. Accordingly, current loss in the lateral direction of a light-emitting device including the first compound may be reduced, thereby reducing mixing of colors between sub-pixels emitting different colors. According to embodiments of the present disclosure, because a change in luminance according to a current amount is large in a low gradation region of a light-emitting device, it is important or useful to reduce current loss in the lateral direction.

In an embodiment, $L_{11}$ in Formula 1 may be a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, or an imidazopyrimidine group, each unsubstituted or substituted with -D, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, —Si($Q_{31}$)($Q_{32}$)($Q_{33}$), —C($Q_{31}$)($Q_{32}$)($Q_{33}$), —B($Q_{31}$)($Q_{32}$), —N($Q_{31}$)($Q_{32}$), —P($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), —P(=S)($Q_{31}$)($Q_{32}$), or any combination thereof.

In one or more embodiments, $L_{11}$ in Formula 1 may be a group represented by one selected from Formulae 3-1 to 3-38:

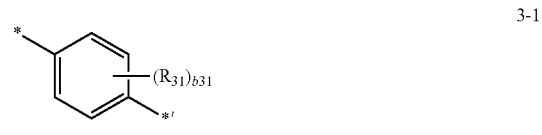

3-1

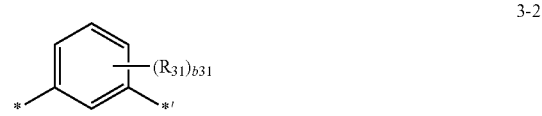

3-2

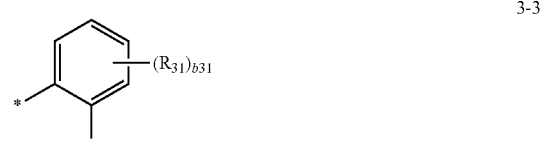

3-3

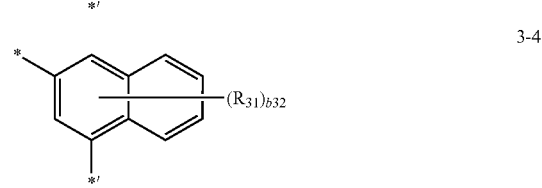

3-4

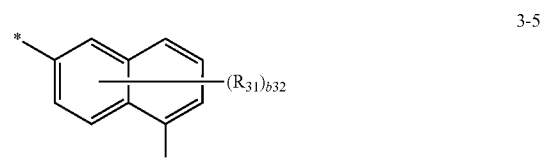

3-5

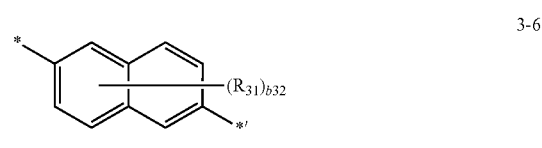

3-6

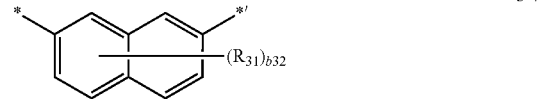

3-7

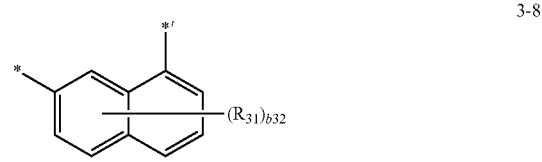

3-8

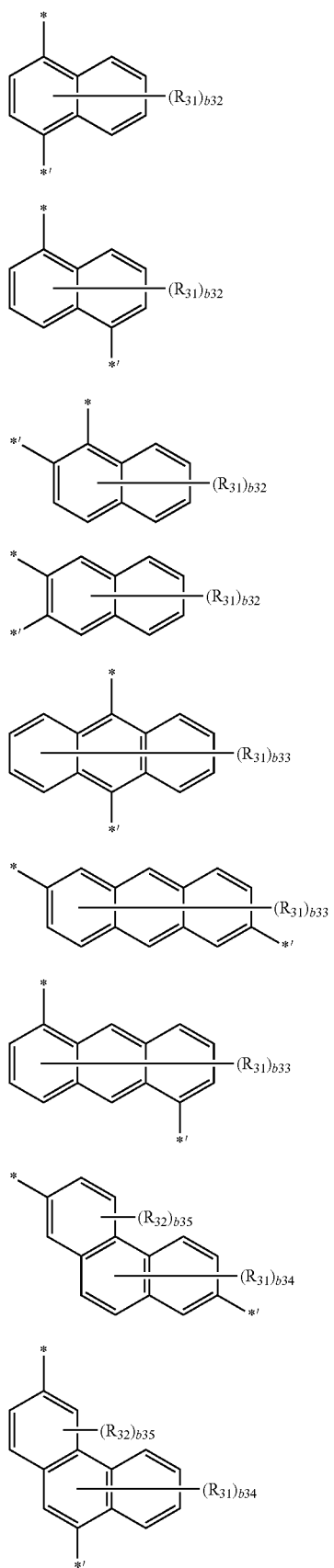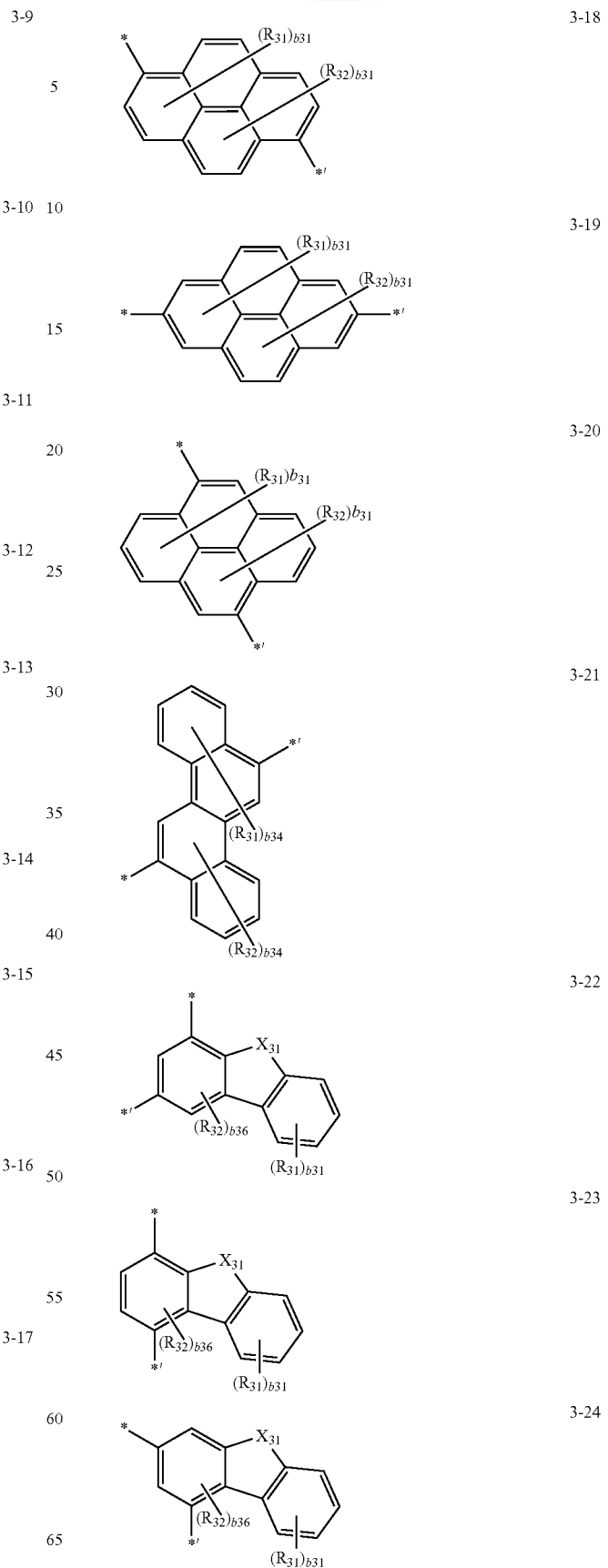

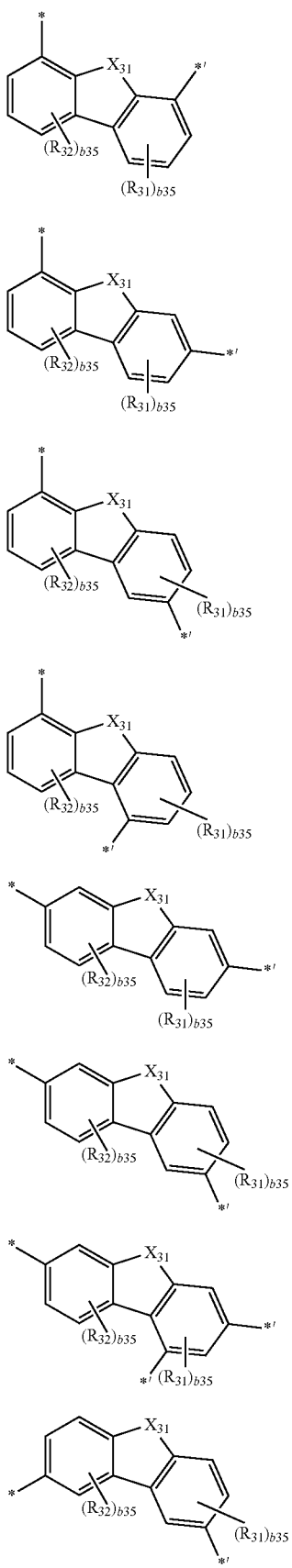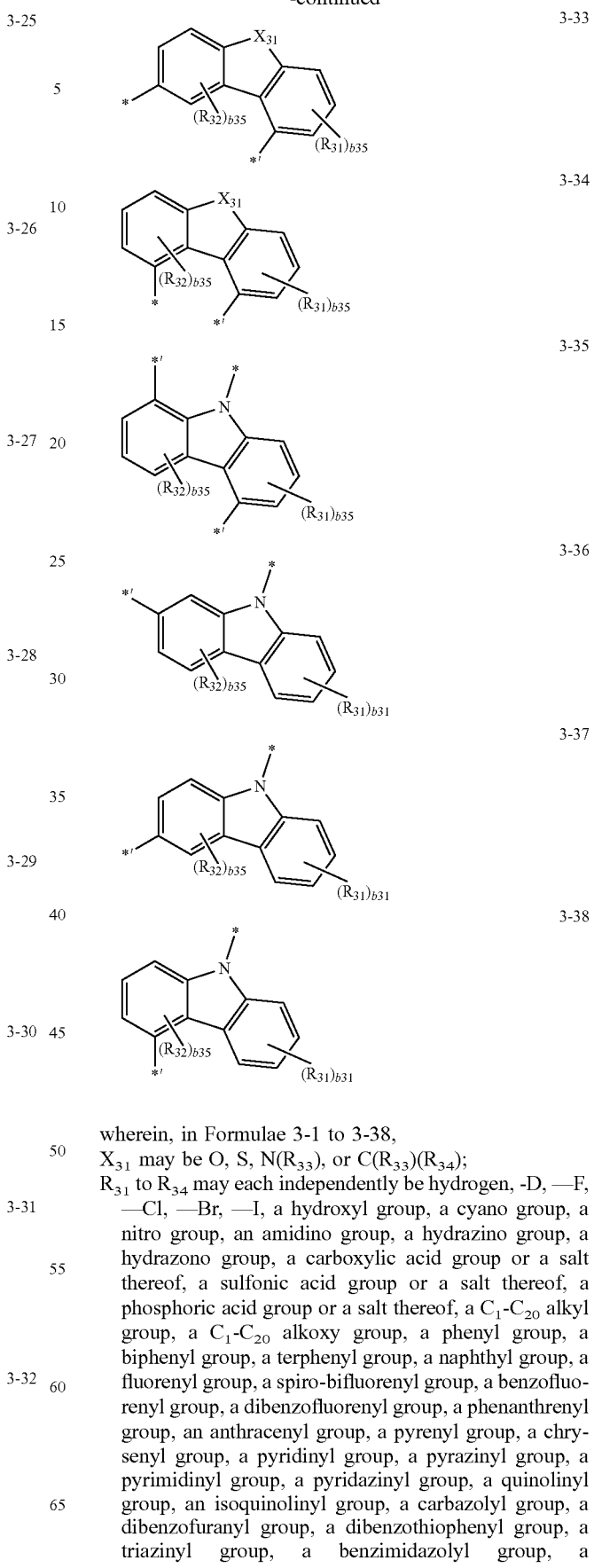

wherein, in Formulae 3-1 to 3-38, $X_{31}$ may be O, S, $N(R_{33})$, or $C(R_{33})(R_{34})$;

$R_{31}$ to $R_{34}$ may each independently be hydrogen, -D, —F, —Cl, —Br, —I, a hydroxyl group, a cyano group, a nitro group, an amidino group, a hydrazino group, a hydrazono group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, a dibenzofuranyl group, a dibenzothiophenyl group, a triazinyl group, a benzimidazolyl group, a phenanthrolinyl group, —Si(Q₃₁)(Q₃₂)(Q₃₃), —C(Q₃₁)(Q₃₂)(Q₃₃), —N(Q₃₁)(Q₃₂), or —B(Q₃₁)(Q₃₂), Q$_{31}$ to Q$_{33}$ may each independently be a C$_1$-C$_{10}$ alkyl group, a C$_1$-C$_{10}$ alkoxy group, a phenyl group, a phenyl group substituted with a cyano group, a biphenyl group, a terphenyl group, or a naphthyl group, b31 may be an integer from 0 to 4,
b32 may be an integer from 0 to 6,
b33 may be an integer from 0 to 8,
b34 may be an integer from 0 to 5,
b35 may be an integer from 0 to 3,
b36 may be an integer from 0 to 2, and
* and *' each indicate a binding site to a neighboring atom.

In an embodiment, R$_{11}$ in Formula 1 may be: a cyclopentenyl group, a cyclohexenyl group, a phenyl group, a biphenyl group, a terphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, an indolyl group, an isoindolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, an azafluorenyl group, an azaspiro-bifluorenyl group, an azacarbazolyl group, a diazacarbazolyl group, an azadibenzofuranyl group, an azadibenzothiophenyl group, an azadibenzosilolyl group, an imidazopyridinyl group, or an imidazopyrimidinyl group, each unsubstituted or substituted with -D, —F, —Cl, —Br, —I, a hydroxyl group, a cyano group, a nitro group, an amidino group, a hydrazino group, a hydrazono group, a C$_1$—C$_{20}$ alkyl group, a C$_1$-C$_{20}$ alkyl group substituted with at least one phenyl group, a C$_1$-C$_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, an indolyl group, an isoindolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, an azafluorenyl group, an azaspiro-bifluorenyl group, an azacarbazolyl group, a diazacarbazolyl group, an azadibenzofuranyl group, an azadibenzothiophenyl group, an azadibenzosilolyl group, an imidazopyridinyl group, an imidazopyrimidinyl group, —Si(Q₃₁)(Q₃₂)(Q₃₃), —C(Q₃₁)(Q₃₂)(Q₃₃), —N(Q₃₁)(Q₃₂), —B(Q₃₁)(Q₃₂), or any combination thereof; or —Si(Q₁)(Q₂)(Q₃), —C(Q₁)(Q₂)(Q₃), —N(Q₁)(Q₂), or —B(Q₁)(Q₂), wherein Q$_1$ to Q$_3$ and Q$_{31}$ to Q$_{33}$ may each independently be a C$_1$-C$_{10}$ alkyl group, a C$_1$-C$_{10}$ alkoxy group, a phenyl group, a phenyl group substituted with a cyano group, a biphenyl group, a terphenyl group, or a naphthyl group.

In one or more embodiments, R$_{11}$ in Formula 1 may be a group represented by one selected from Formulae 5-1 to 5-18:

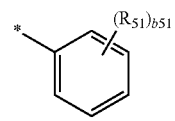

5-1

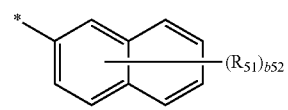

5-2

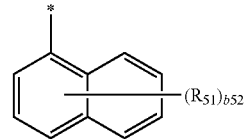

5-3

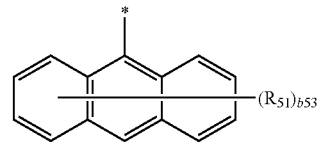

5-4

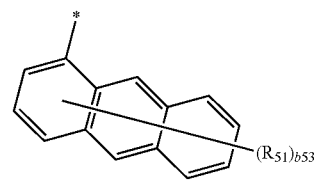

5-5

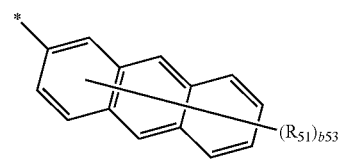

5-6

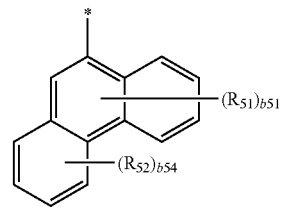

5-7

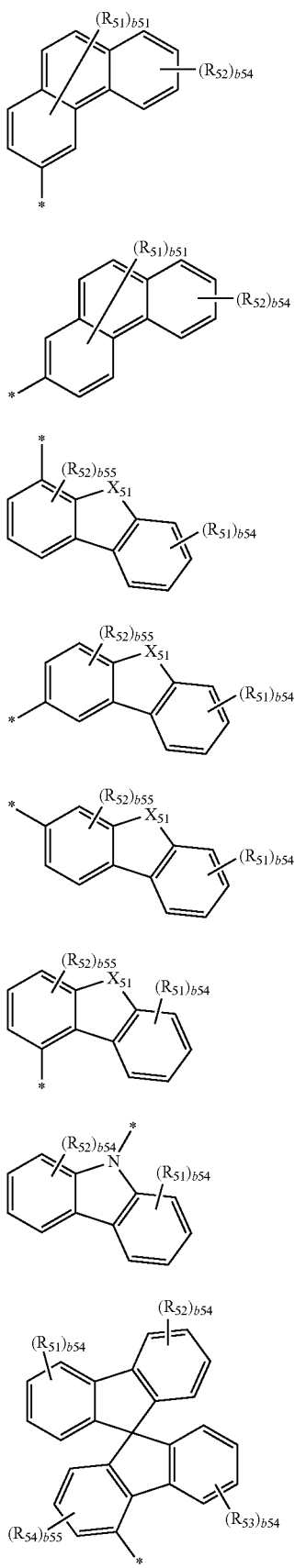
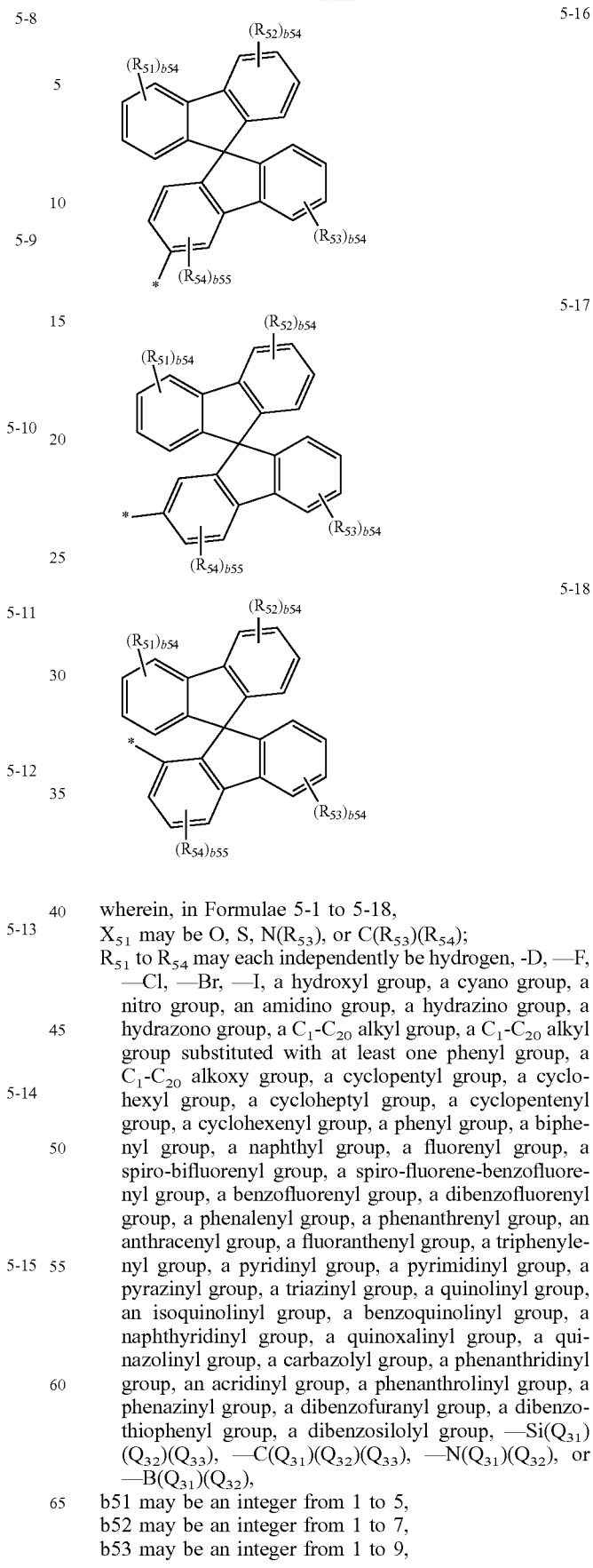

wherein, in Formulae 5-1 to 5-18, $X_{51}$ may be O, S, $N(R_{53})$, or $C(R_{53})(R_{54})$;

$R_{51}$ to $R_{54}$ may each independently be hydrogen, -D, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one phenyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrimidinyl group, a pyrazinyl group, a triazinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a dibenzofuranyl group, a dibenzothiophenyl group, a dibenzosilolyl group, —Si($Q_{31}$)($Q_{32}$)($Q_{33}$), —C($Q_{31}$)($Q_{32}$)($Q_{33}$), —N($Q_{31}$)($Q_{32}$), or —B($Q_{31}$)($Q_{32}$), b51 may be an integer from 1 to 5,
b52 may be an integer from 1 to 7,
b53 may be an integer from 1 to 9, b54 may be an integer from 1 to 4, b55 may be an integer from 1 to 3, $Q_{31}$ to $Q_{33}$ may each independently be a $C_1$-$C_{10}$ alkyl group, a $C_1$-$C_{10}$ alkoxy group, a phenyl group, a phenyl group substituted with a cyano group, a biphenyl group, a terphenyl group, or a naphthyl group, and

* indicates a binding site to a neighboring atom.

In one or more embodiments, $R_{11}$ in Formula 1 may be a group represented by one selected from Formulae 6-1 to 6-173:

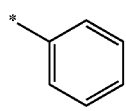
6-1

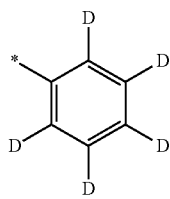
6-2

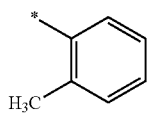
6-3

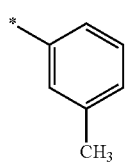
6-4

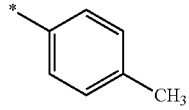
6-5

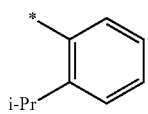
6-6

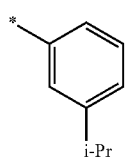
6-7

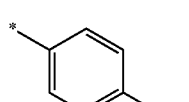
6-8

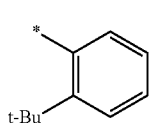
6-9

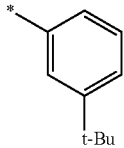
6-10

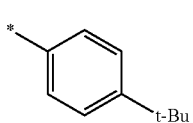
6-11

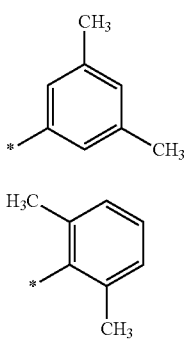
6-12

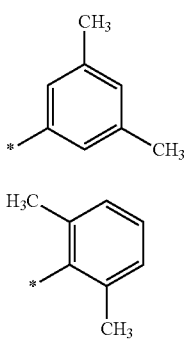
6-13

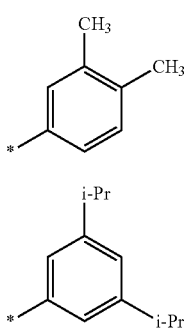
6-14

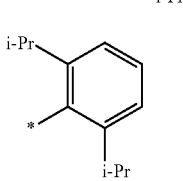
6-15

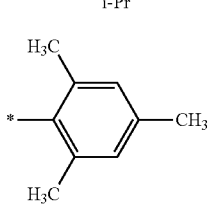
6-16

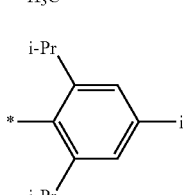
6-17

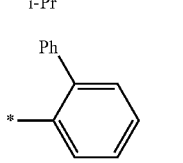
6-18

6-19

-continued
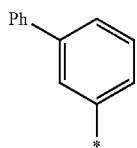
6-20
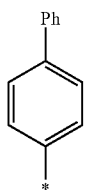
6-21
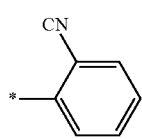
6-22
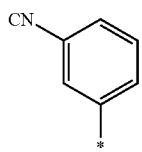
6-23
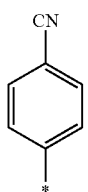
6-24
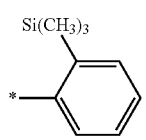
6-25
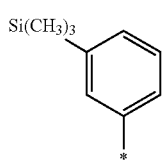
6-26
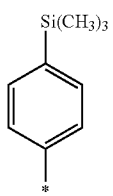
6-27
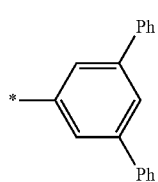
6-28
-continued
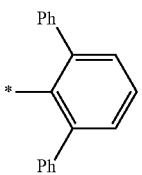
6-29
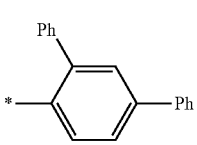
6-30
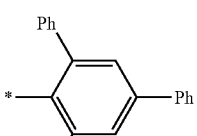
6-31
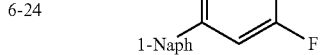
6-32
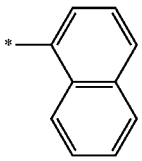
6-33
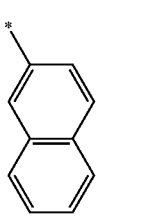
6-34
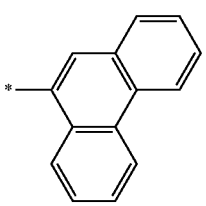
6-35
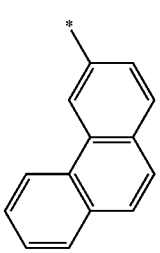
6-36

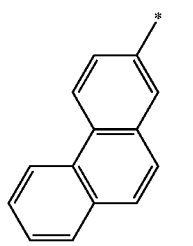
6-37
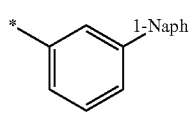 6-38
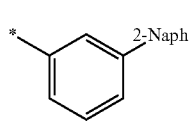 6-39
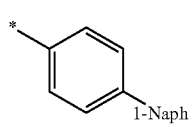 6-40
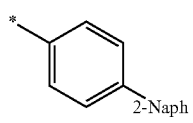 6-41
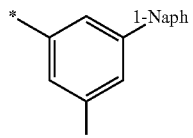 6-42
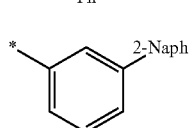 6-43
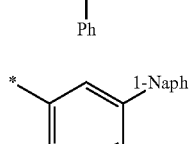 6-44
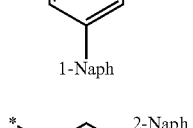 6-45
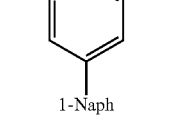 6-46
6-47
6-48
6-49
6-50
6-51
6-52
6-53
6-54
6-55
6-56
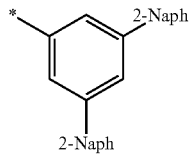

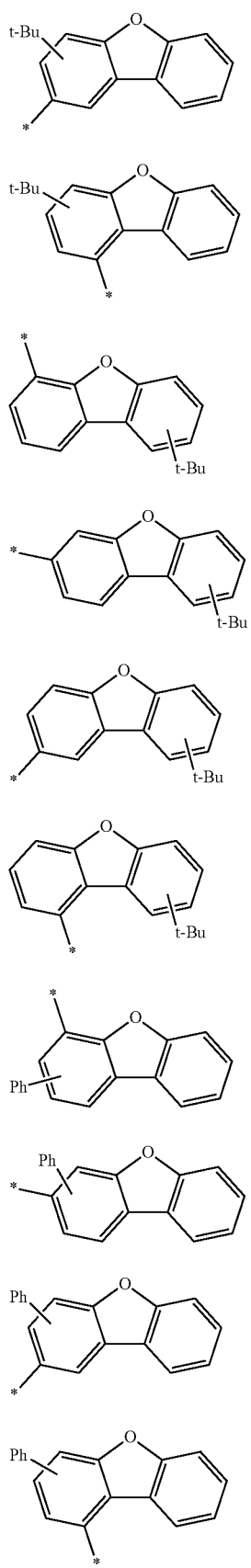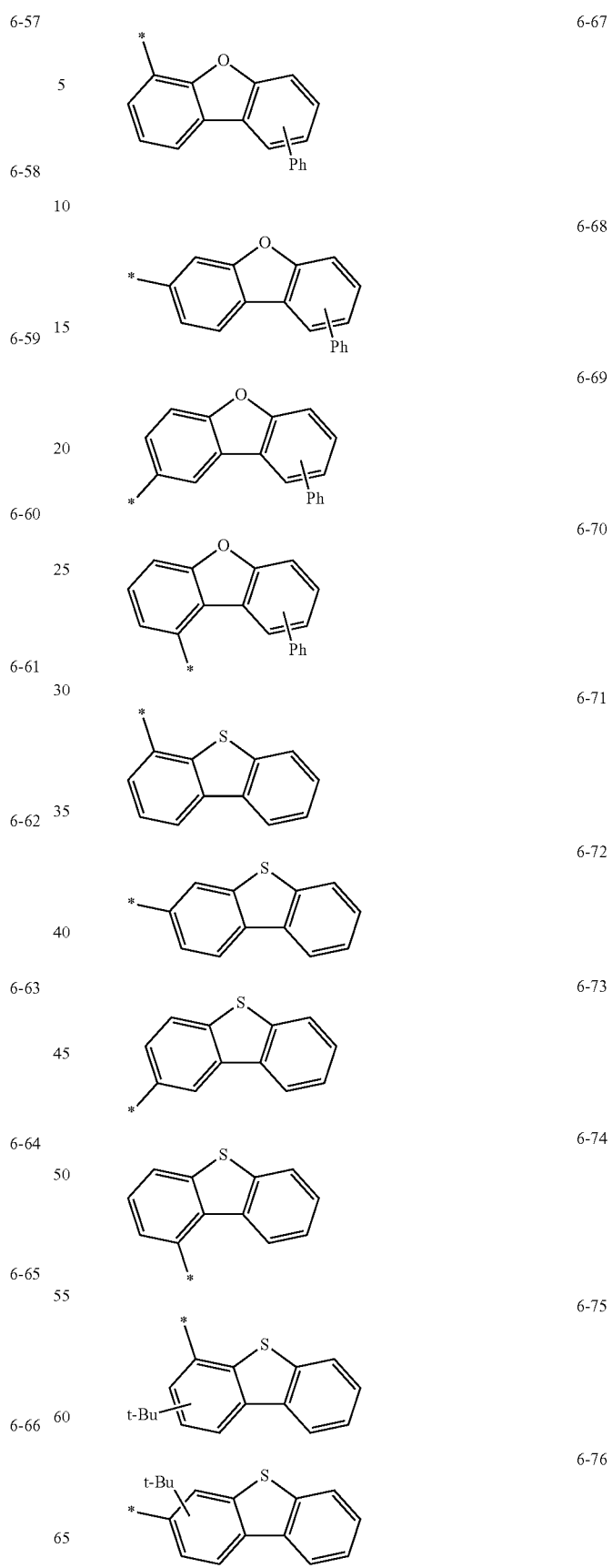

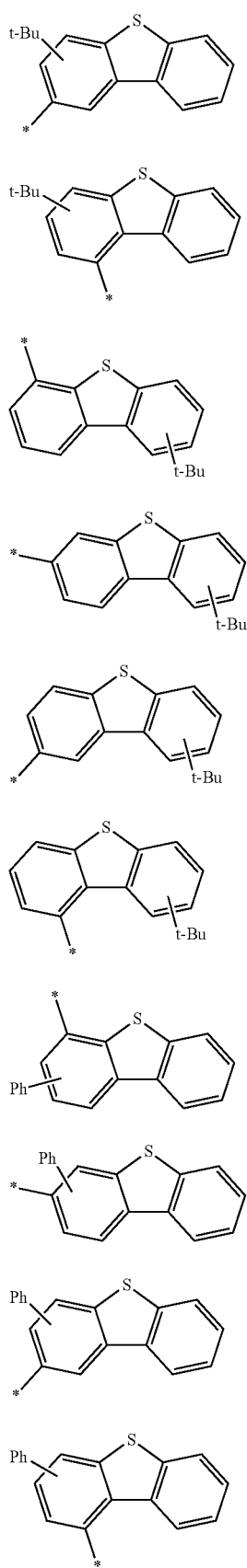
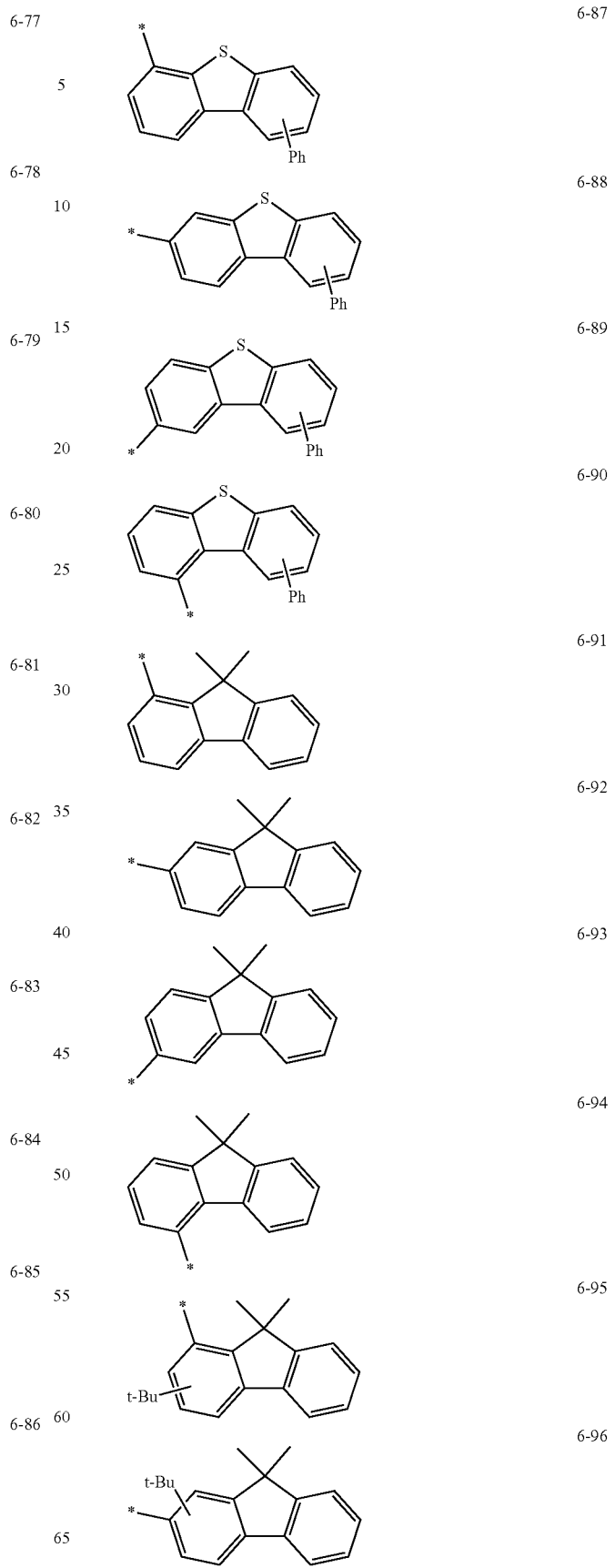

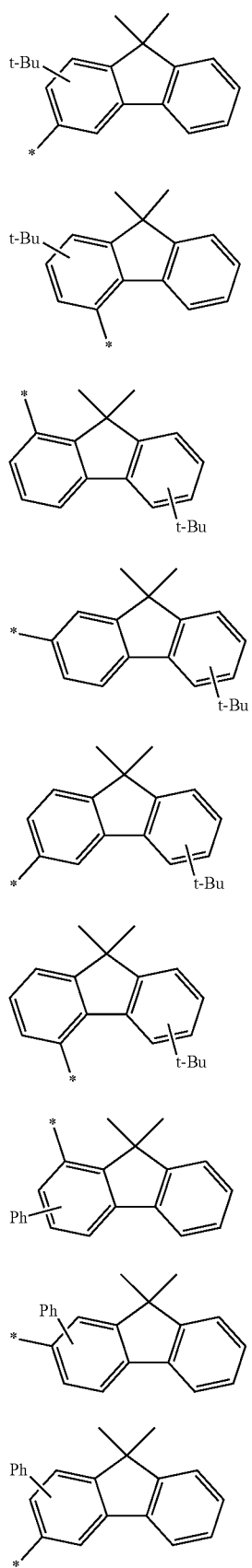
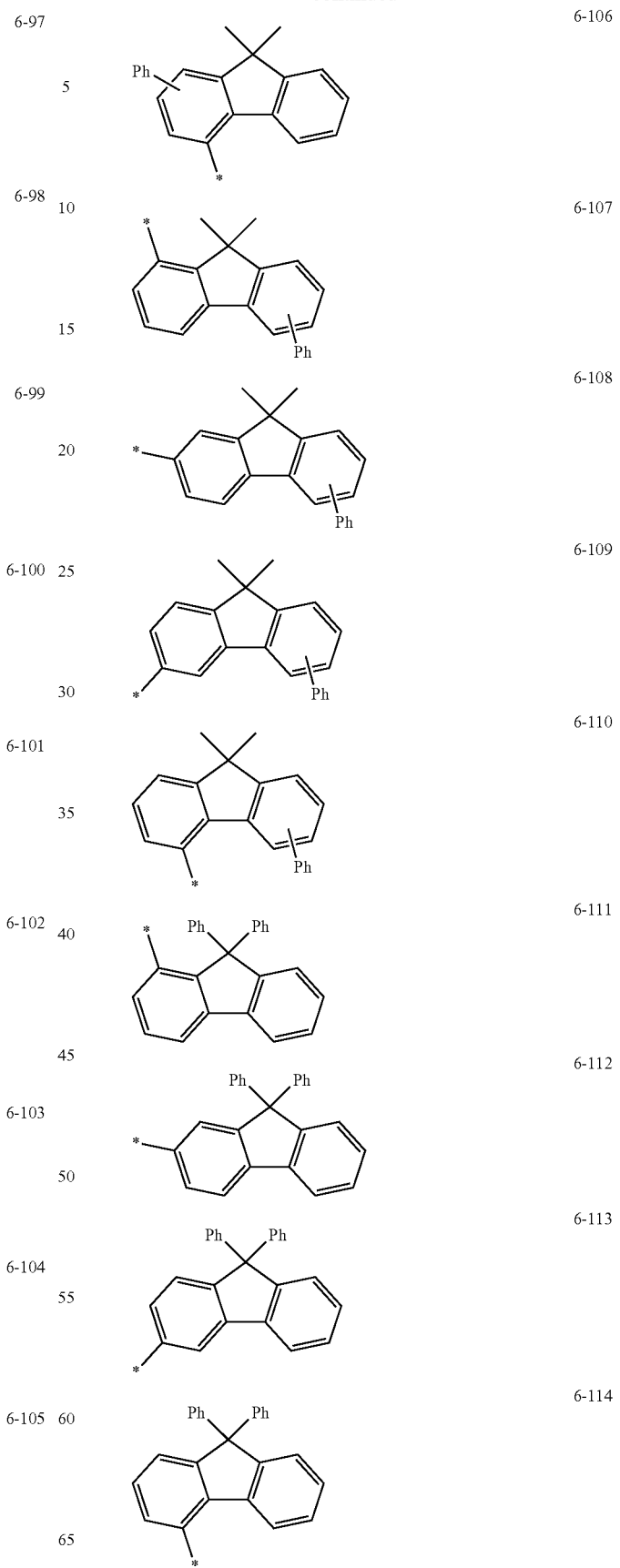

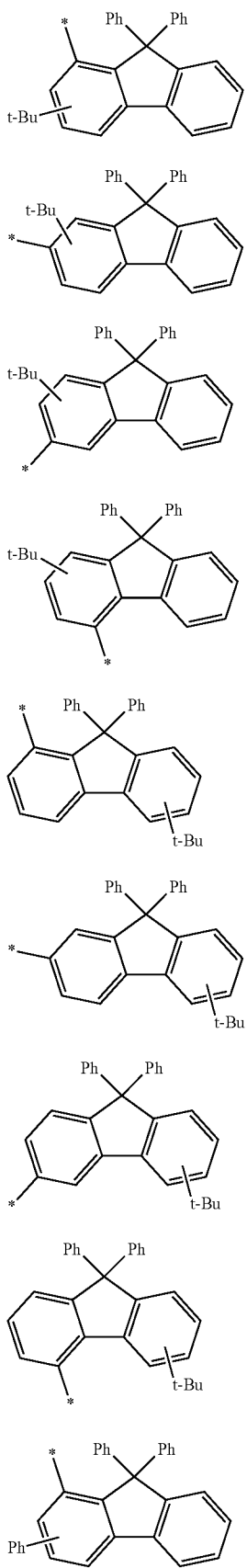
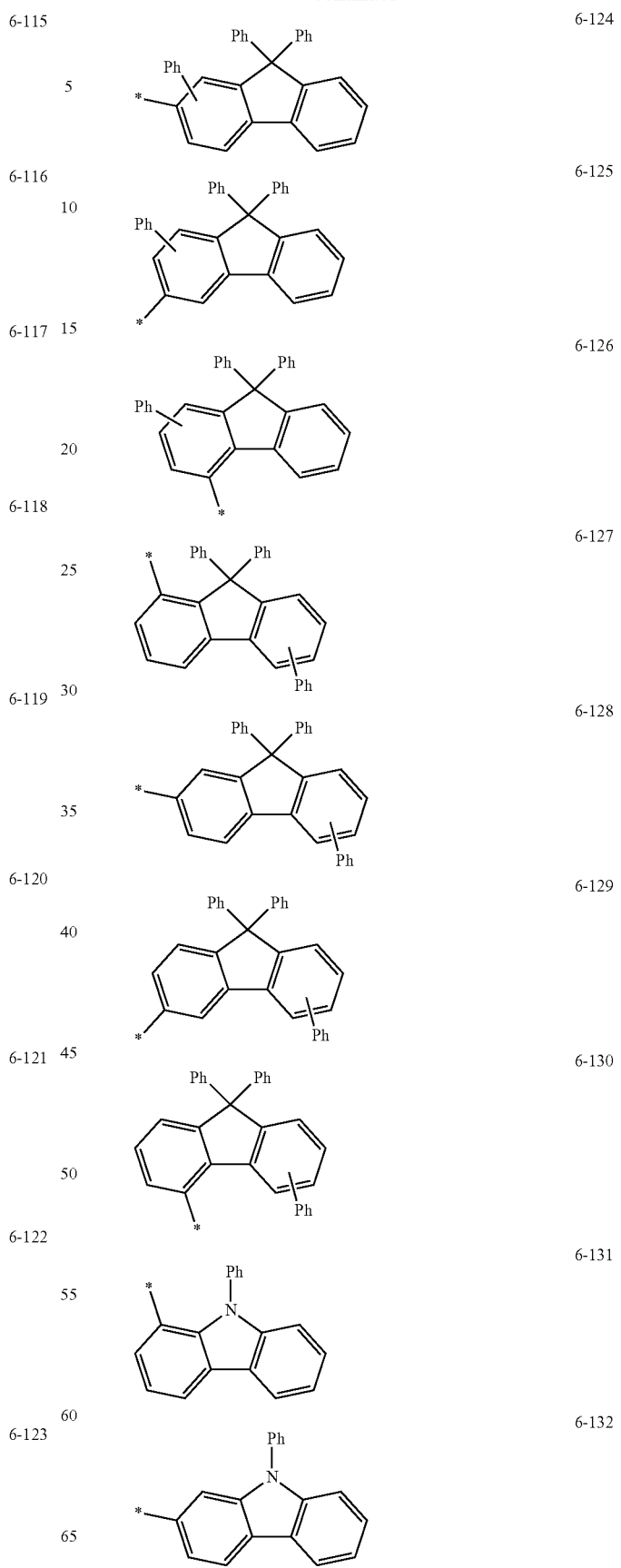

6-133 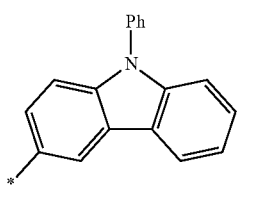
6-134 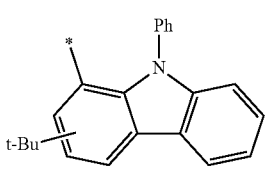
6-135 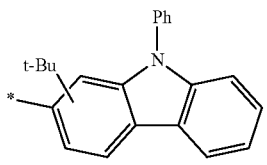
6-136 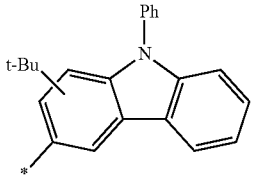
6-137 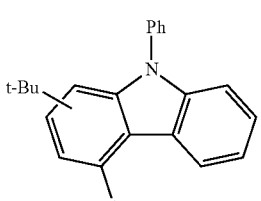
6-138 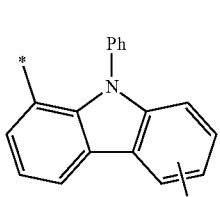
6-139 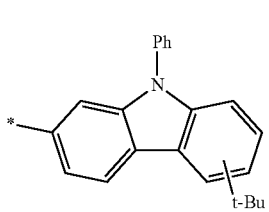
6-140 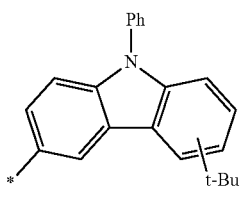
6-141 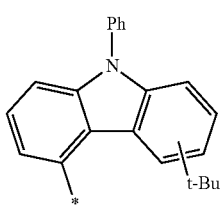
6-142 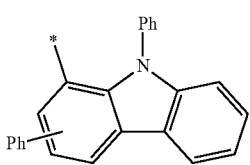
6-143 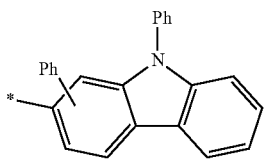
6-144 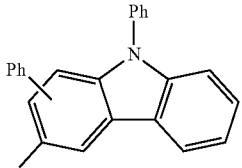
6-145 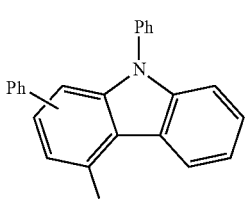
6-146 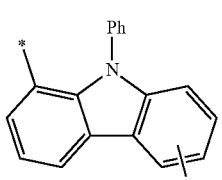
6-147 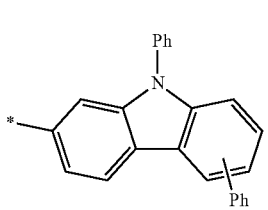
6-148

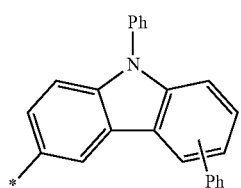 6-149
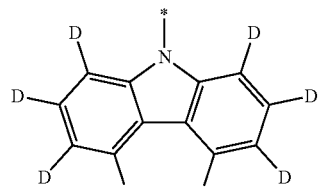 6-157
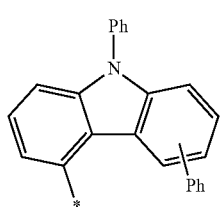 6-150
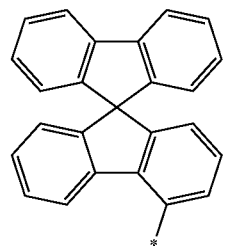 6-158
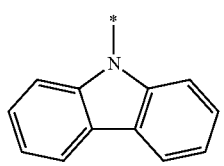 6-151
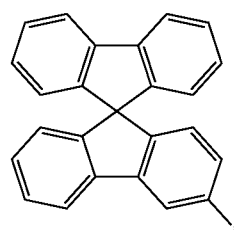 6-159
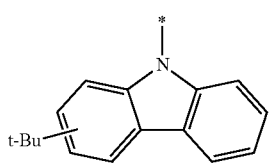 6-152
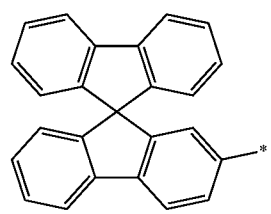 6-160
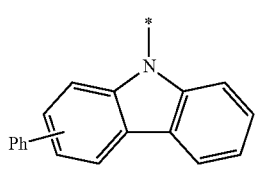 6-153
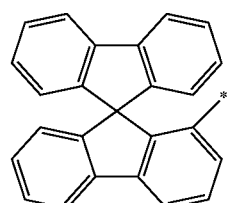 6-161
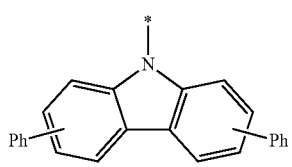 6-154
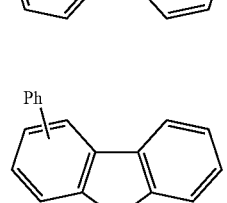 6-155
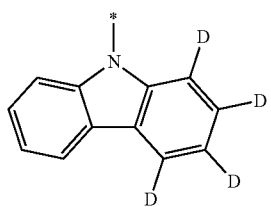 6-156
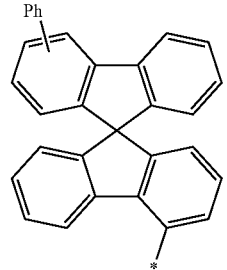 6-162

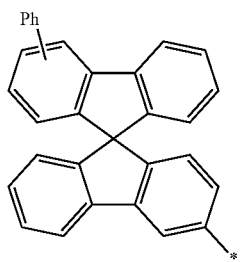
6-163

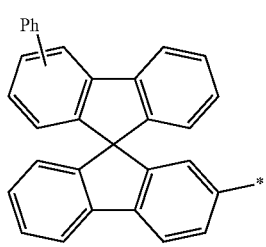
6-164

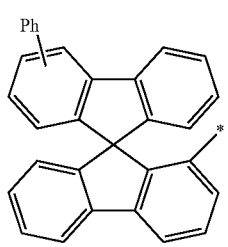
6-165

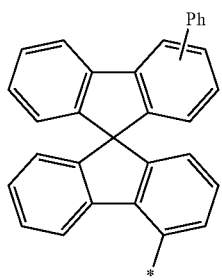
6-166

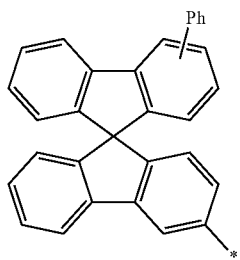
6-167

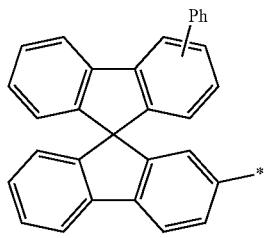
6-168

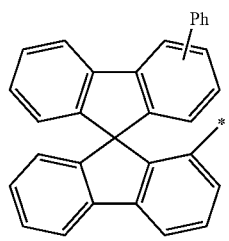
6-169

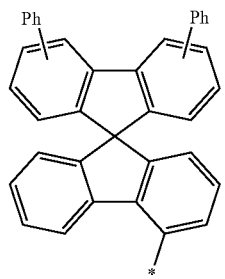
6-170

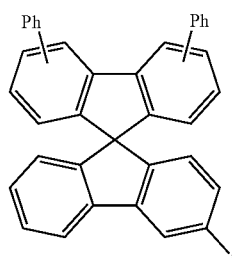
6-171

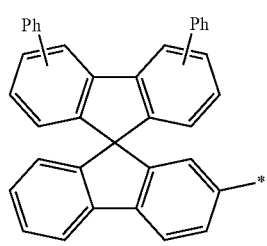
6-172

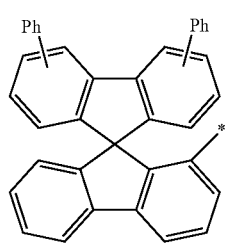
6-173 wherein, in Formulae 6-1 to 6-173, i-Pr may be an isopropyl group;

t-Bu may be a tert-butyl group;

Ph may be a phenyl group;

1-Naph may be an 1-naphthyl group;

2-Naph may be a 2-naphthyl group; and

* indicates a binding site to a neighboring atom.

In an embodiment, $R_x$ and $R_y$ in Formula 1 may each be a group represented by one selected from Formulae 2-1 to 2-3, and $R_x$ and $R_y$ may be identical to each other:

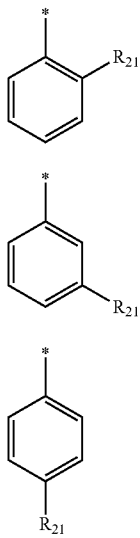

2-1

2-2

2-3 wherein, in Formulae 2-1 to 2-3, $R_{21}$ may be a cyclohexyl group, a tert-butyl group, or an n-hexyl group, and

* indicates a binding site to a neighboring atom.

In more detail, $R_x$ and $R_y$ in Formula 1 may each be a group represented by Formula 2-3, and $R_x$ and $R_y$ may be identical to each other. When $R_x$ and $R_y$ are represented by Formula 2-3, a substituent having a large steric hindrance may be substituted at a para position, and thus, the effect of reducing the charge mobility of the corresponding compound may be relatively large.

In more detail, $R_x$ and $R_y$ in Formula 1 may each be a group represented by Formula 2-11, or $R_x$ and $R_y$ may each be a group represented by Formula 2-12:

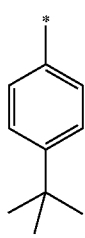

2-11

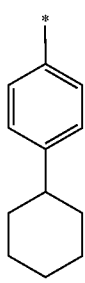

2-12 wherein, in Formulae 2-11 and 2-12,

* indicates a binding site to a neighboring atom.

In an embodiment, the first compound may be selected from compounds of Group I:

Group I

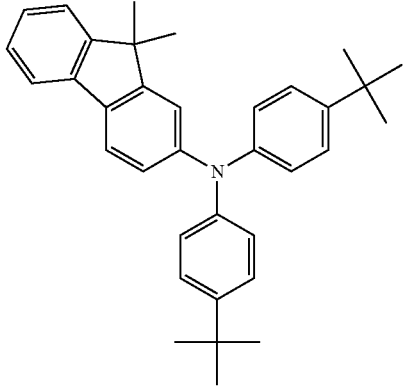

1

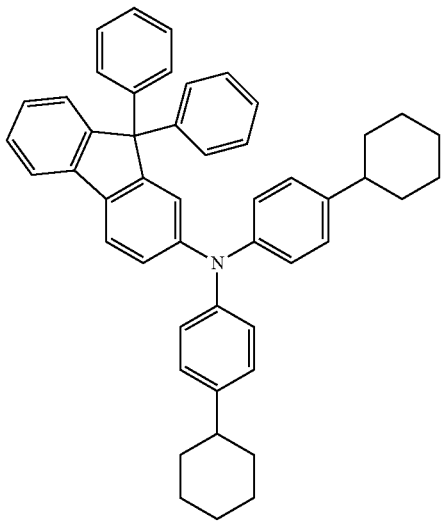

2

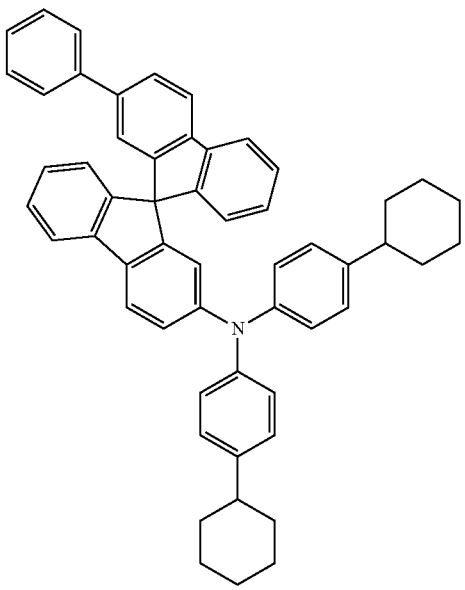

3

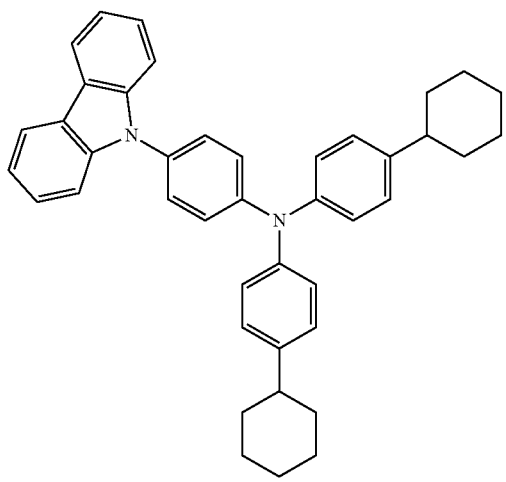
4
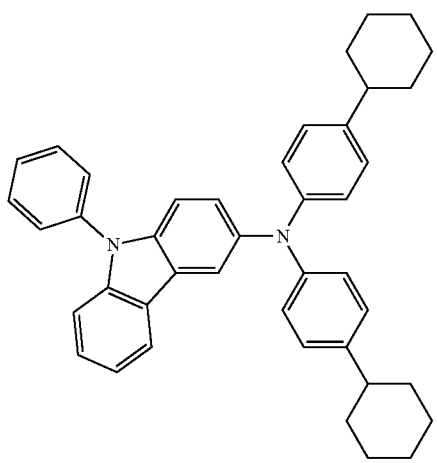
7
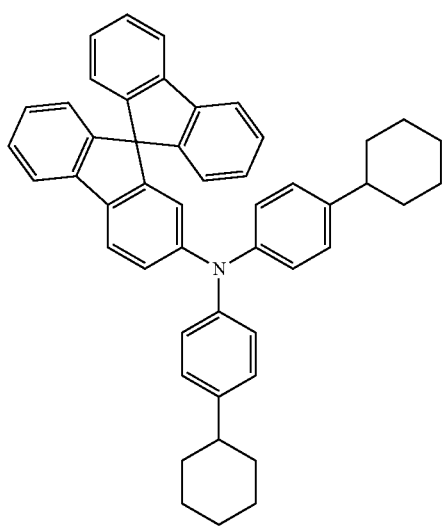
5
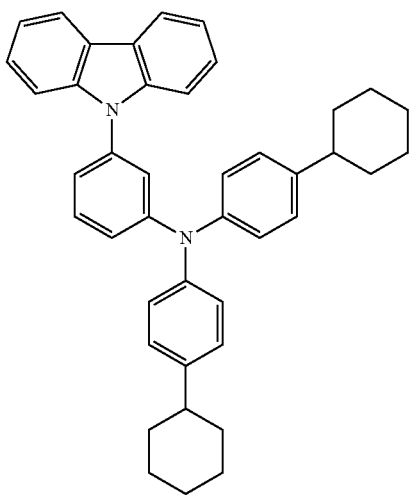
8
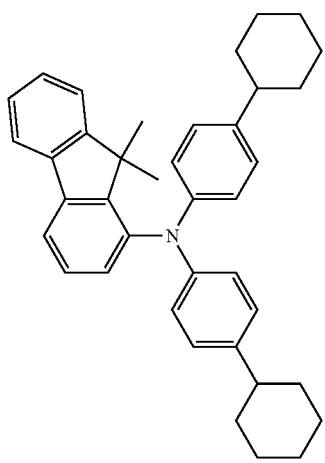
6
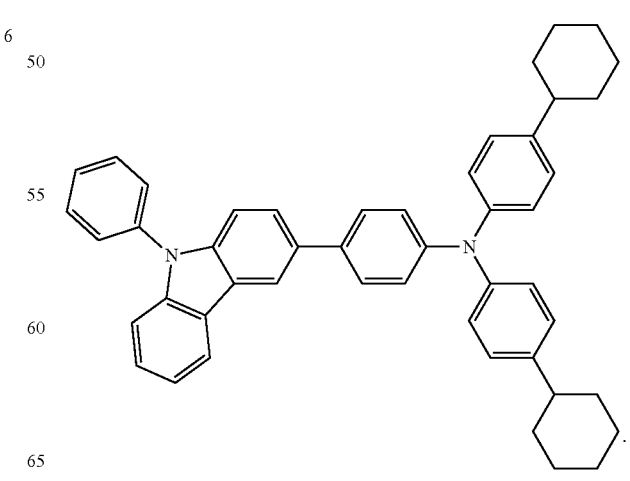
9

In an embodiment, the second compound may be represented by Formula 201:
wherein, in Formula 201,

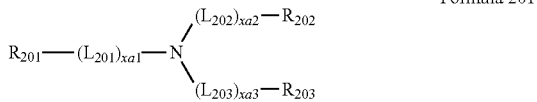

Formula 201

$L_{201}$ to $L_{203}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xa1 to xa3 may each independently be an integer from 0 to 5, $R_{201}$ to $R_{203}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$.

Formula 201 will be described in more detail herein below.

In more detail, the second compound may include NPB, NPB(NPD), β-NPB, TPD, or any combination thereof, but embodiments of the present disclosure are not limited thereto.

Another aspect of one or more embodiments provides a light-emitting device including: a substrate partitioned into a first subpixel area, a second subpixel area, and a third subpixel area; a plurality of anodes respectively in the first subpixel area, the second subpixel area, and the third subpixel area of the substrate; a cathode facing the plurality of anodes; an interlayer including an emission layer between the plurality of anodes and the cathode; and a hole transport region between the plurality of anodes and the emission layer, wherein the hole transport region includes a first layer and a second layer, the first layer includes a first compound represented by Formula 1, the second layer includes a second compound, and the first compound and the second compound are different from each other.

Formula 1

In Formula 1, $L_{11}$ may be a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$, a11 may be an integer from 0 to 5, $R_{11}$ may be a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_1$-$C_{60}$ heteroaryl group unsubstituted or substituted with at least one $R_{10a}$, a monovalent non-aromatic condensed polycyclic group unsubstituted or substituted with at least one $R_{10a}$, or a monovalent non-aromatic condensed heteropolycyclic group unsubstituted or substituted with at least one $R_{10a}$, $R_x$ and $R_y$ may each be a group represented by Formula 2, and $R_x$ and $R_y$ may be identical to each other,

Formula 2 wherein, in Formula 2, $R_{21}$ may be a cyclopentyl group, a cyclohexyl group, a tert-butyl group, or a $C_5$-$C_{10}$ alkyl group, and

* indicates a binding site to a neighboring atom.

Another aspect of one or more embodiments provides an electronic apparatus including the light-emitting device. The electronic apparatus may further include a thin-film transistor. In an embodiment, the electronic apparatus may further include a thin-film transistor including a source electrode and a drain electrode, and the anode of the light-emitting device may be electrically coupled to the source electrode or the drain electrode. In one or more embodiments, the electronic apparatus may further include a color filter, a color conversion layer, a touch screen layer, a polarizing layer, or any combination thereof. Further details of the electronic apparatus are the same as described elsewhere in the present specification.

Description of FIG. 1

Figure 1:
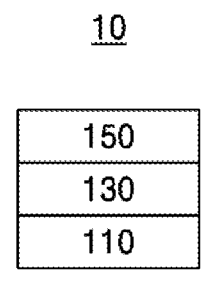

FIG. 1 is a schematic cross-sectional view of a light-emitting device 10 according to an embodiment. The light-emitting device 10 includes an anode 110, an interlayer 130, and a cathode 150.

Hereinafter, the structure of the light-emitting device 10 according to an embodiment and a method of manufacturing the light-emitting device 10 will be described in connection with FIG. 1.

Anode 110

In FIG. 1, a substrate may be additionally under the anode 110 or above the cathode 150. As the substrate, a glass substrate and/or a plastic substrate may be used. In one or more embodiments, the substrate may be a flexible substrate, and may include plastics (e.g., polymers) having excellent heat resistance and/or durability, such as polyimide, polyethylene terephthalate (PET), polycarbonate, polyethylene naphthalate, polyarylate (PAR), polyetherimide, or any combination thereof.

The anode 110 may be formed by, for example, depositing and/or sputtering a material for forming the anode 110 on the substrate. As the material for forming the anode 110, a material having a high work function that facilitates injection of holes may be used.

The anode 110 may be a reflective electrode, a semi-transmissive electrode, or a transmissive electrode. In an embodiment, the anode 110 may include indium tin oxide (ITO), indium zinc oxide (IZO), tin oxide (SnO₂), zinc oxide (ZnO), magnesium (Mg), silver (Ag), aluminum (Al), aluminum-lithium (Al—Li), calcium (Ca), magnesium-indium (Mg—In), magnesium-silver (Mg—Ag), or any combination thereof.

In more detail, when the anode 110 is a transmissive electrode, indium tin oxide (ITO), indium zinc oxide (IZO), tin oxide ($SnO_2$), zinc oxide (ZnO), or any combinations thereof may be used as a material for forming the anode 110. In one or more embodiments, when the anode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as a material for forming the anode 110.

The anode 110 may have a single-layered structure including (e.g., consisting of) a single layer or a multi-layered structure including a plurality of layers. In an embodiment, the anode 110 may have a three-layered structure of ITO/Ag/ITO.

Interlayer 130

The interlayer 130 may be on the anode 110. The interlayer 130 may include an emission layer.

The interlayer 130 may further include a hole transport region between the anode 110 and the emission layer and an electron transport region between the emission layer and the cathode 150.

The interlayer 130 may further include, in addition to various suitable organic materials, metal-containing compounds such as organometallic compounds, inorganic materials such as quantum dots, and/or the like.

In one or more embodiments, the interlayer 130 may include, i) two or more light-emitting units sequentially stacked between the anode 110 and the cathode 150 and ii) a charge generation layer between the two or more emitting units. When the interlayer 130 includes an emitting unit and a charge generation layer as described above, the light-emitting device 10 may be a tandem light-emitting device.

Hole Transport Region in Interlayer 130

The hole transport region may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The hole transport region may include a hole injection layer, a hole transport layer, an emission auxiliary layer, an electron blocking layer, or any combination thereof.

The hole transport region may include a first layer and a second layer, and, for example, may have a first layer and a second layer which are stacked sequentially from the anode 110.

In an embodiment, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers are stacked sequentially from the anode 110. In this regard, the first layer may act as a hole injection layer, and the second layer may act as a hole transport layer.

The hole transport region may further include, in addition to the first compound represented by Formula 1, a compound represented by Formula 201, a compound represented by Formula 202, or any combination thereof:

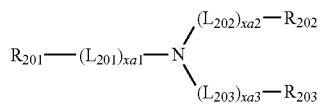

Formula 201

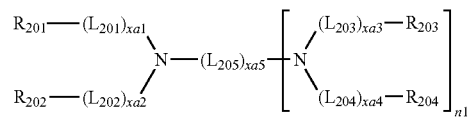

Formula 202 wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, each of Formulae 201 and 202 may include at least one selected from groups represented by Formulae CY201 to CY217 (e.g., as one of groups $R_{201}$ to $R_{204}$):

CY201

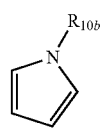

CY202

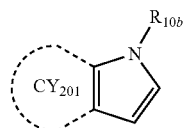

CY203

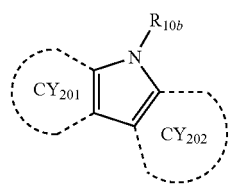

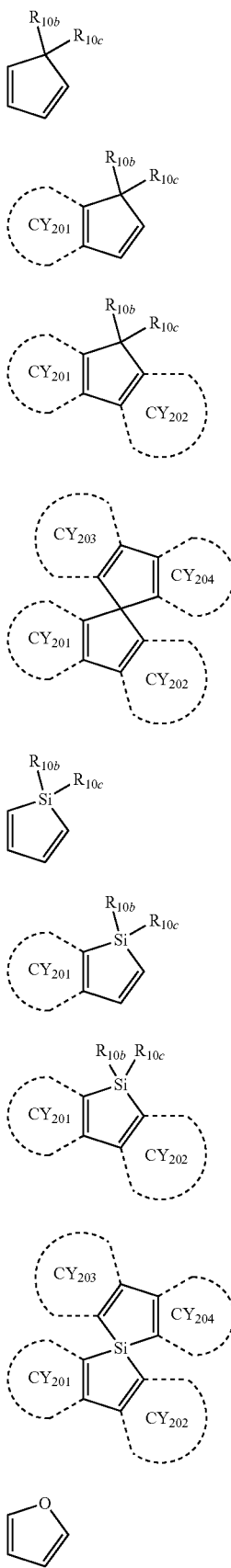

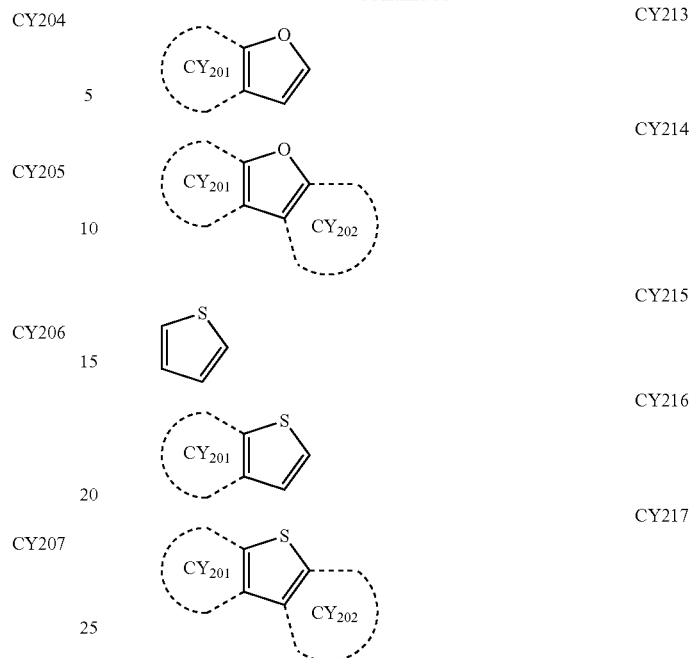

wherein, in Formulae CY201 to CY217, $R_{10b}$ and $R_{10c}$ are each the same as described in connection with $R_{10a}$, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, ring $CY_{201}$ to ring $CY_{204}$ in Formulae CY201 to CY217 may each independently be a benzene group, a naphthalene group, a phenanthrene group, or an anthracene group.

In one or more embodiments, each of Formulae 201 and 202 may include at least one selected from groups represented by Formulae CY201 to CY203.

In one or more embodiments, Formula 201 may include at least one selected from groups represented by Formulae CY201 to CY203 and at least one selected from groups represented by Formulae CY204 to CY217.

In one or more embodiments, in Formula 201, xa1 may be 1, $R_{201}$ may be a group represented by one selected from Formulae CY201 to CY203, xa2 may be 0, and $R_{202}$ may be a group represented by one selected from Formulae CY204 to CY207.

In one or more embodiments, each of Formulae 201 and 202 may not include a group represented by one selected from Formulae CY201 to CY203.

In one or more embodiments, each of Formulae 201 and 202 may not include a group represented by one selected from Formulae CY201 to CY203, and may include at least one selected from groups represented by Formulae CY204 to CY217.

In one or more embodiments, each of Formulae 201 and 202 may not include a group represented by one selected from Formulae CY201 to CY217.

In an embodiment, the hole transport region may include one or more selected from Compounds HT1 to HT46, m-MTDATA, TDATA, 2-TNATA, NPB(NPD), β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:
HT1
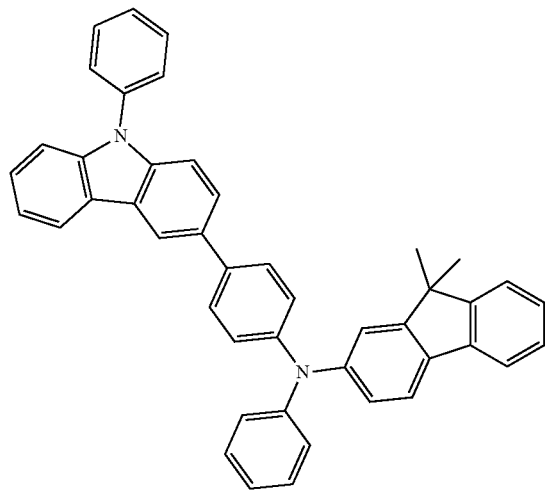
HT2
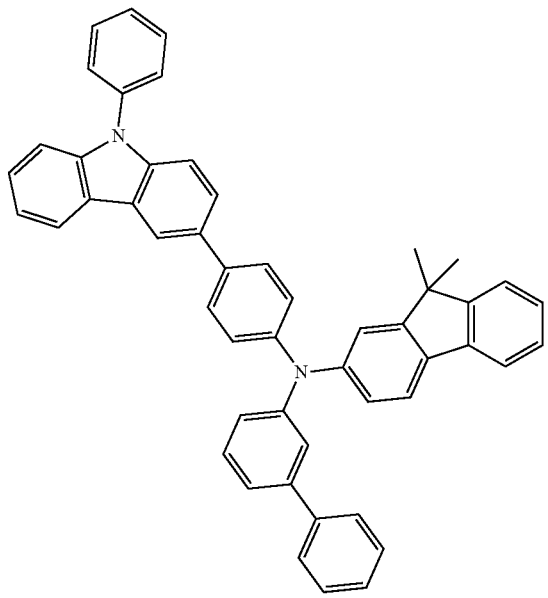
HT3
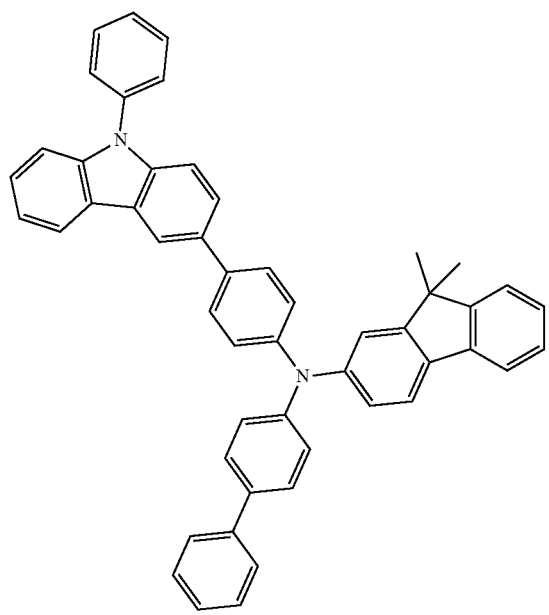
HT4
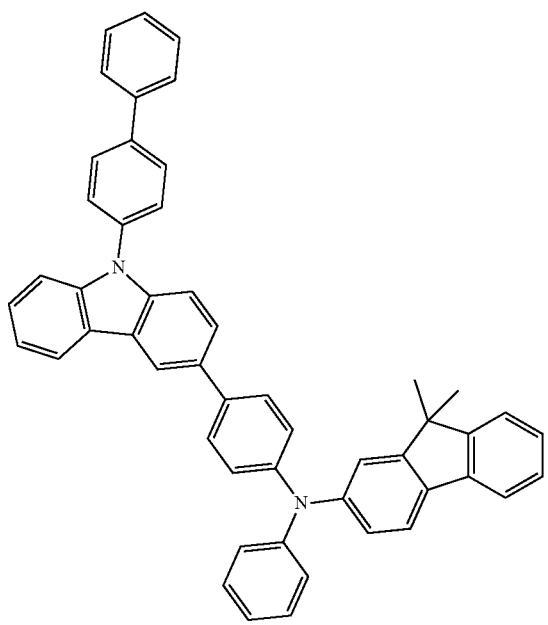

-continued
HT5
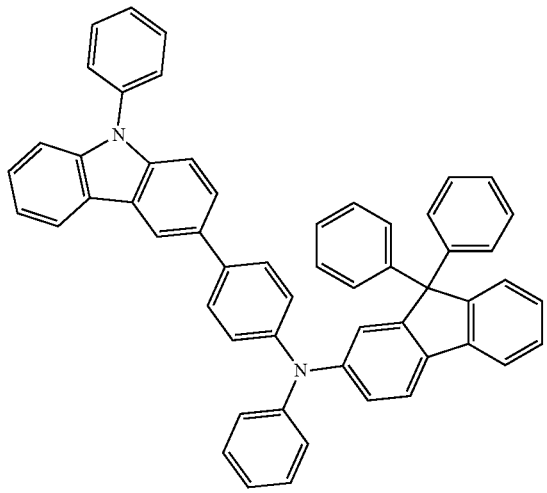
HT6
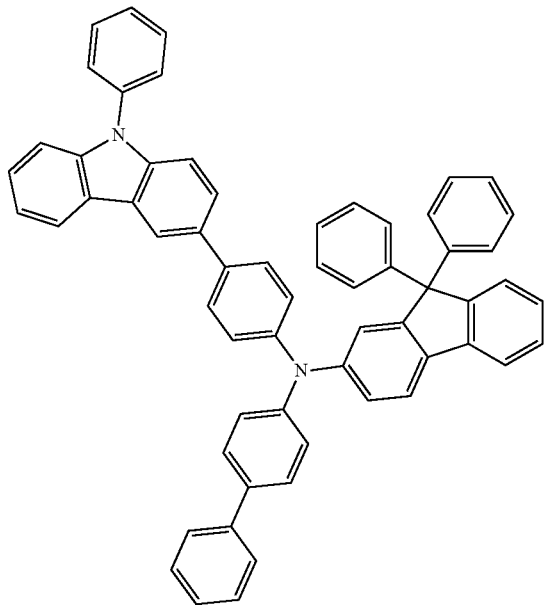
HT7
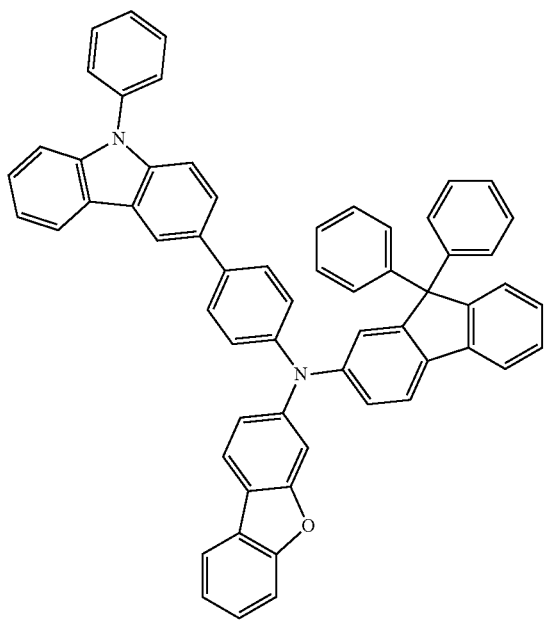
HT8
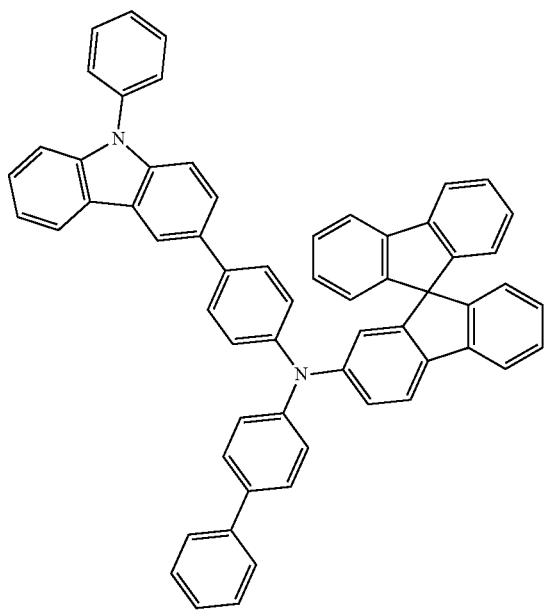

-continued
HT9
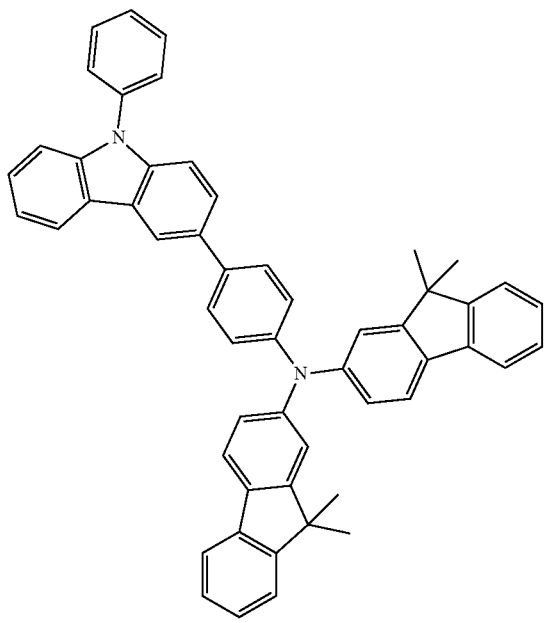
HT10
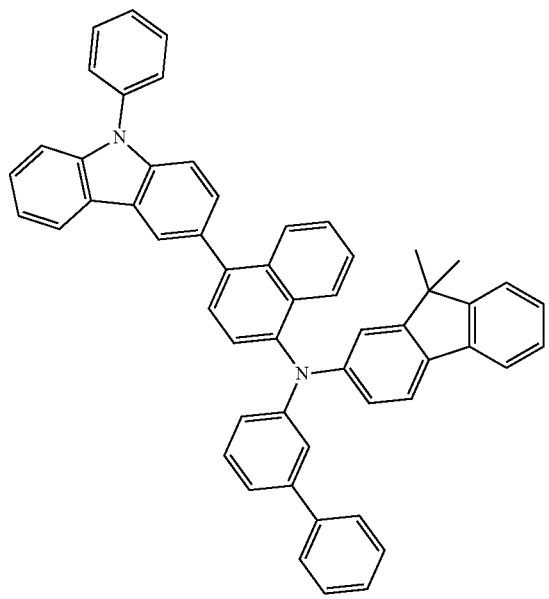
HT11
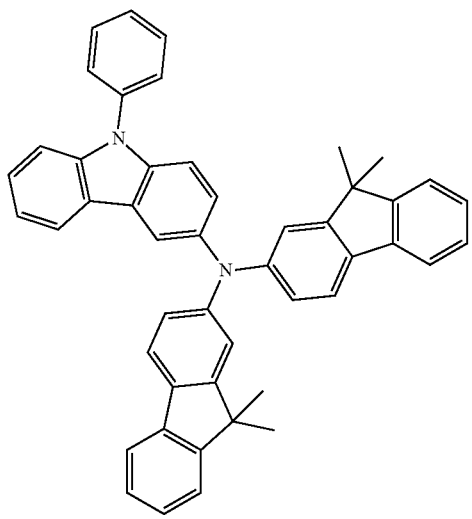
HT12
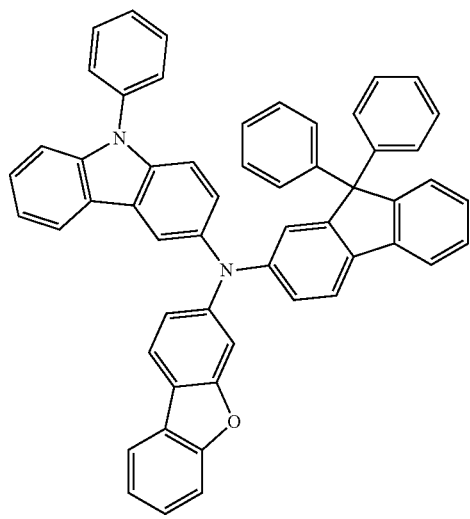

-continued
HT13
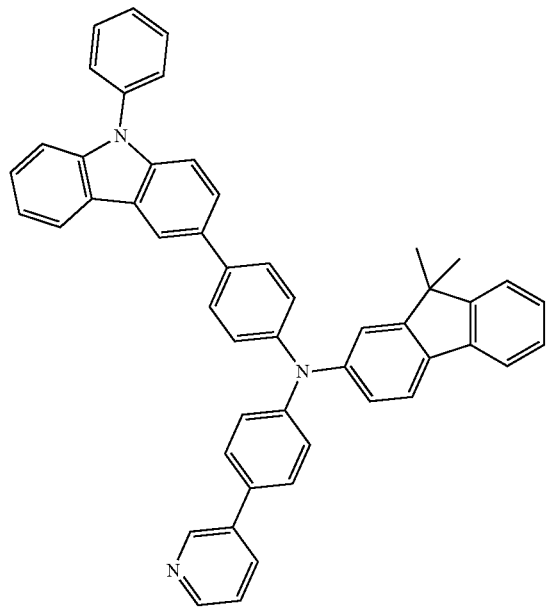
HT14
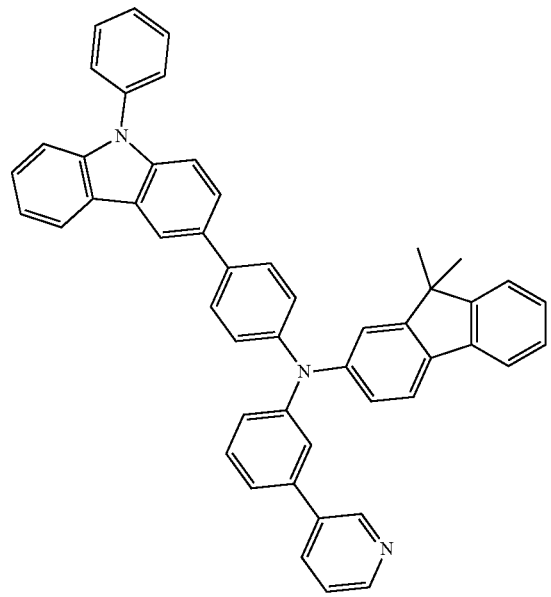
HT15
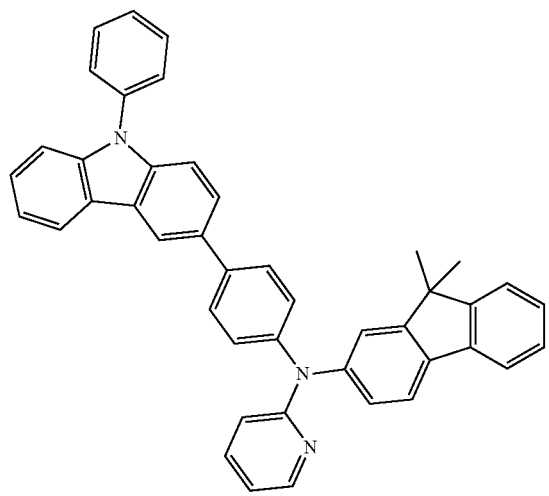
HT16
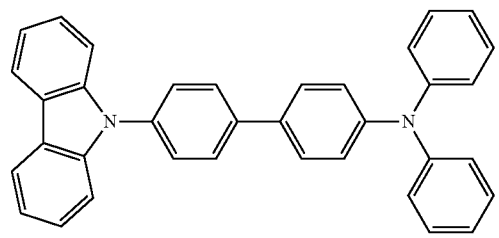
HT17
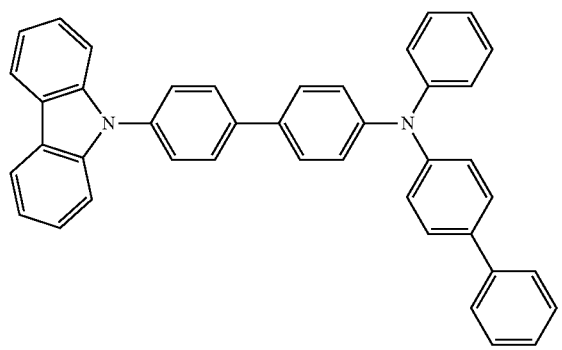
HT18
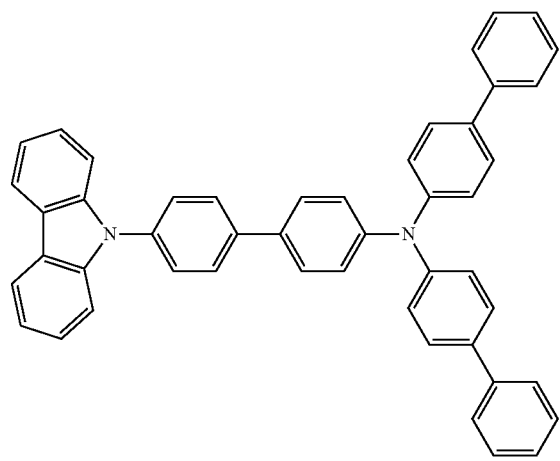

-continued
HT19
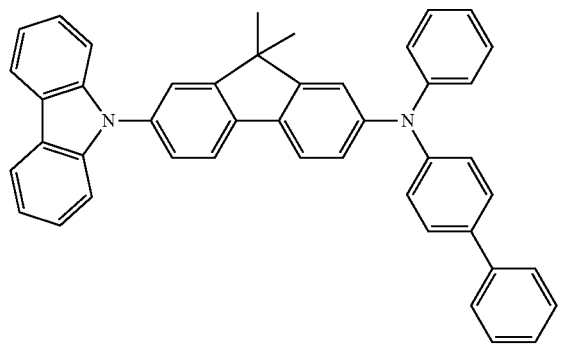
HT20
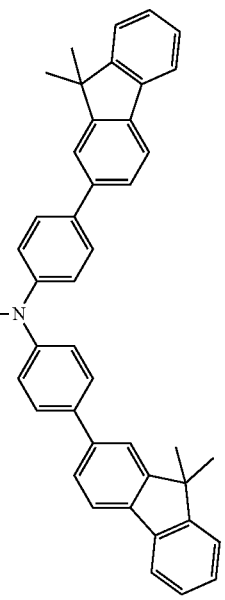
HT21
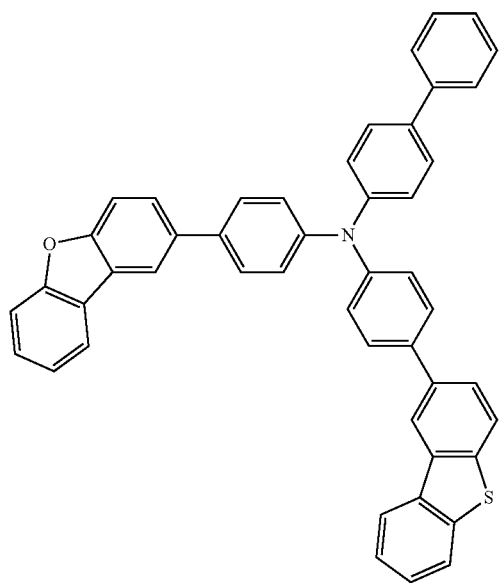
HT22
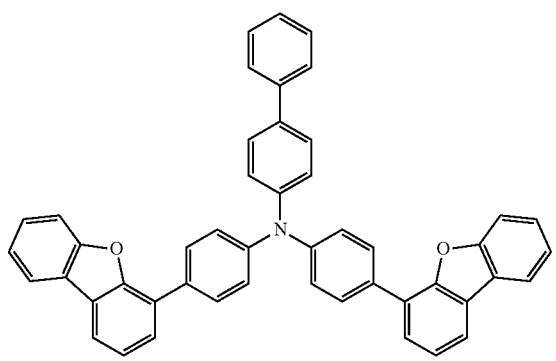

-continued
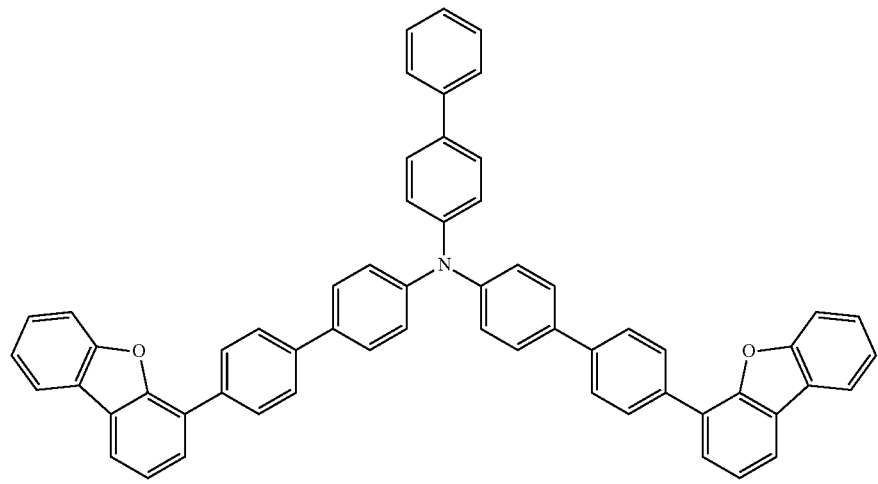
HT23
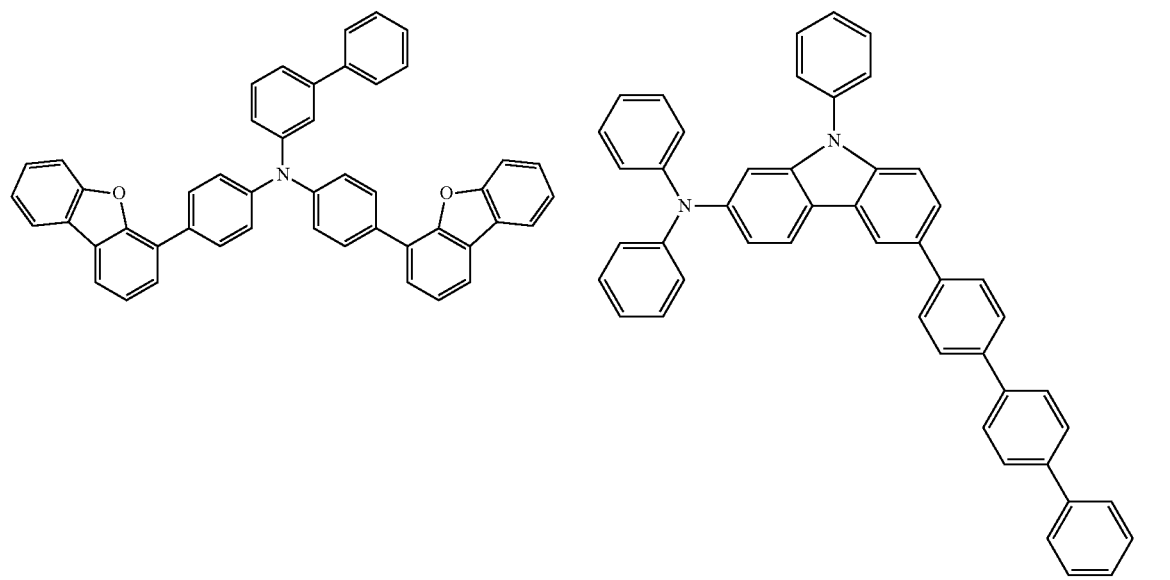
HT24  HT25
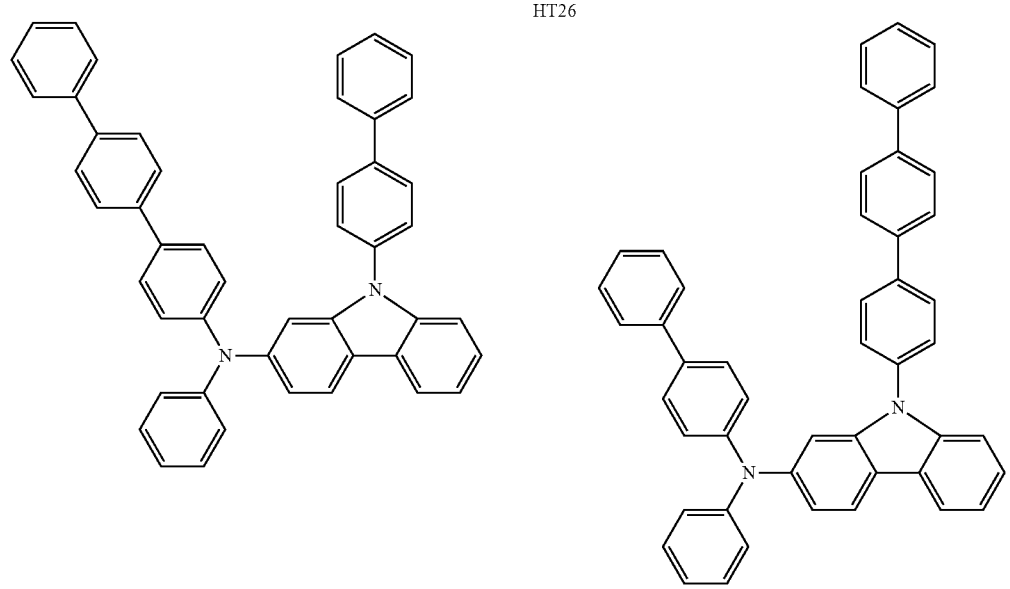
HT26  HT27

-continued
HT28
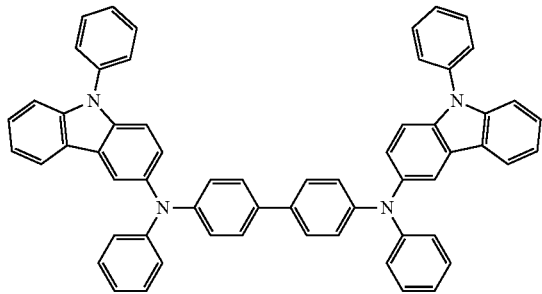
HT29
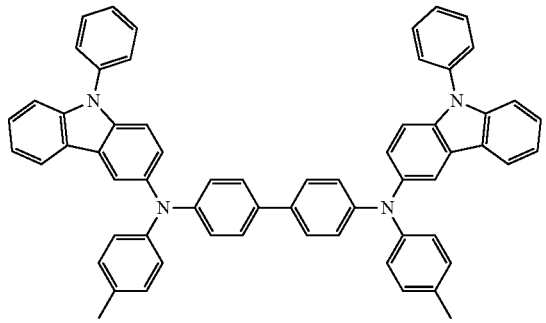
HT30
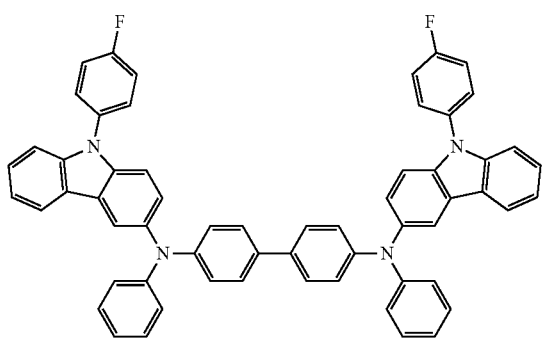
HT31
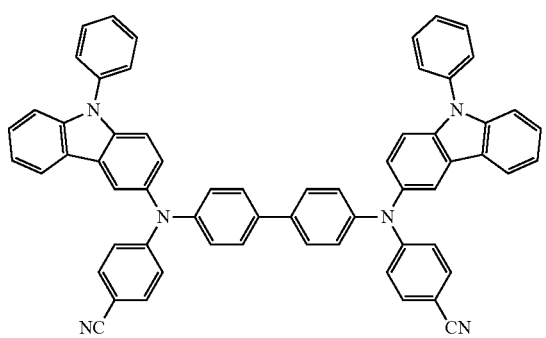
HT32
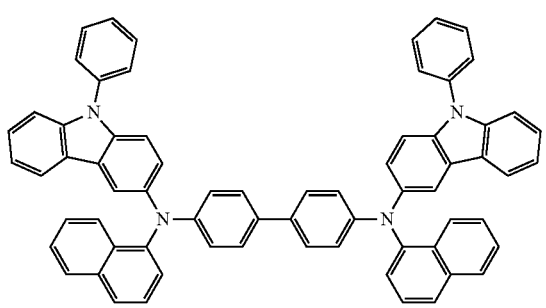
HT33
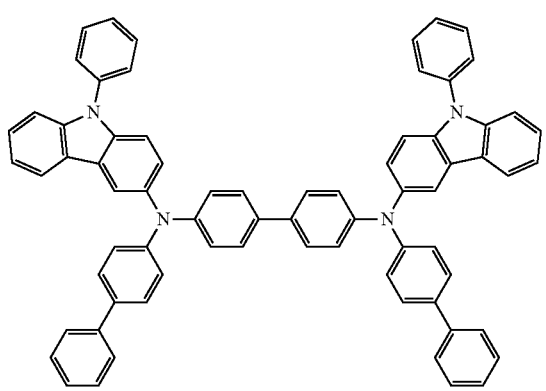
HT34
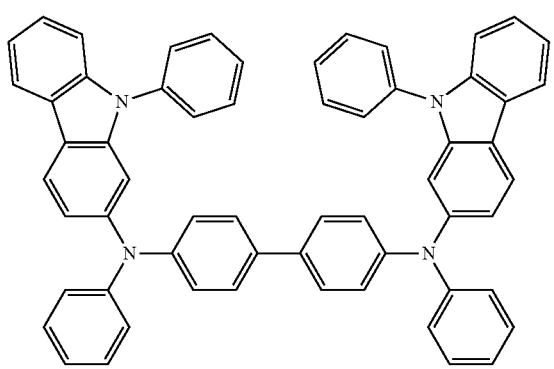
HT35
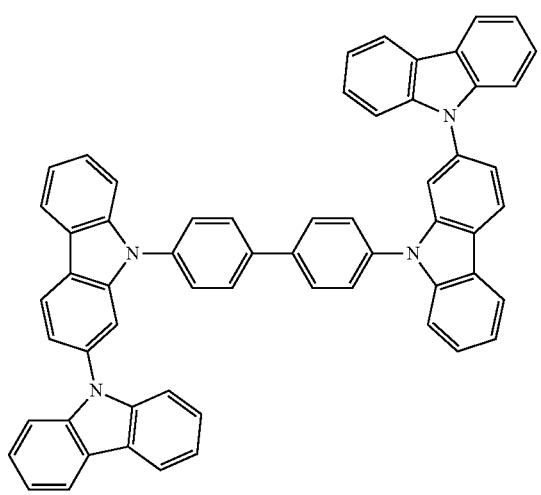

-continued
HT36
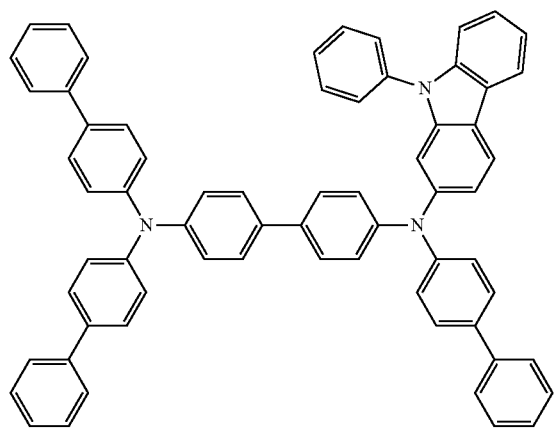
HT37
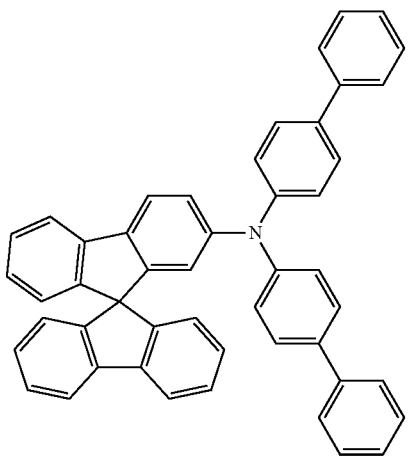
HT38
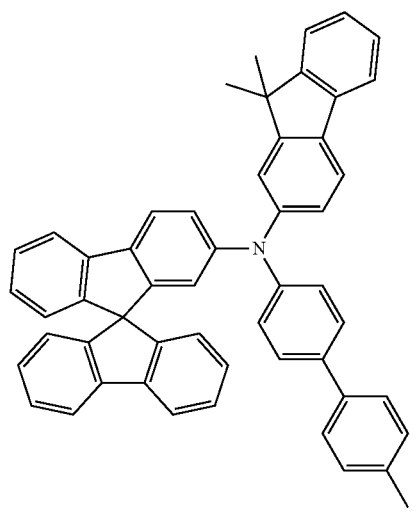
HT39
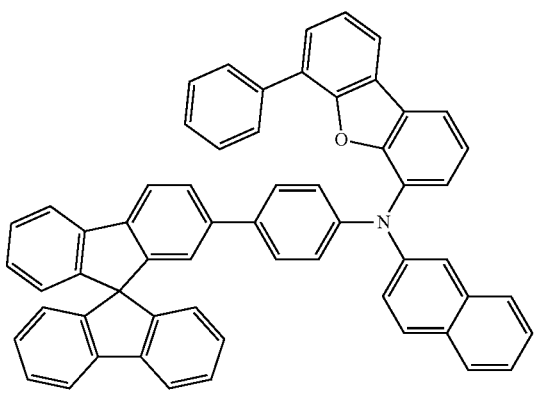
HT40
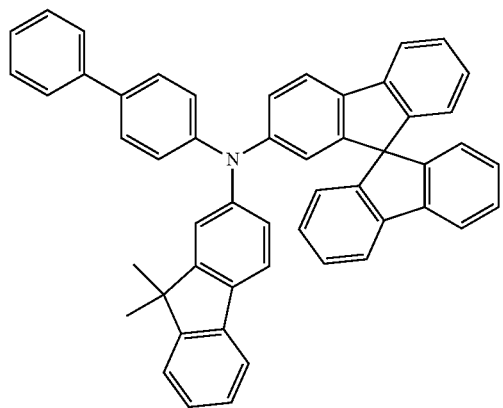
HT41
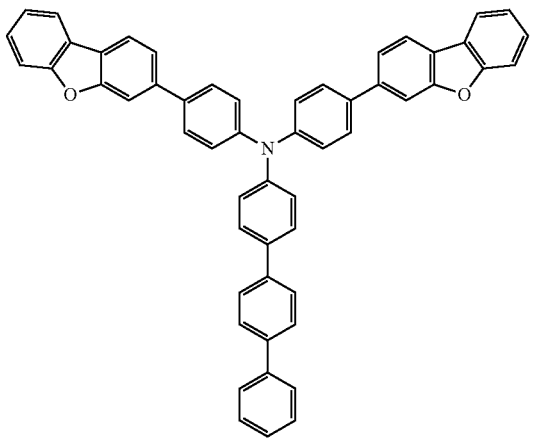

HT42
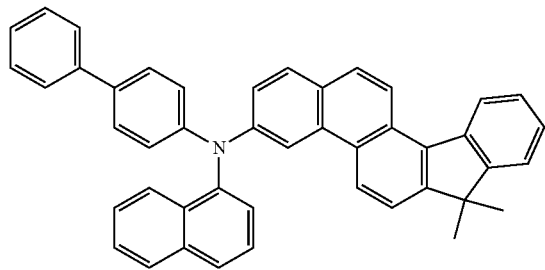
HT43
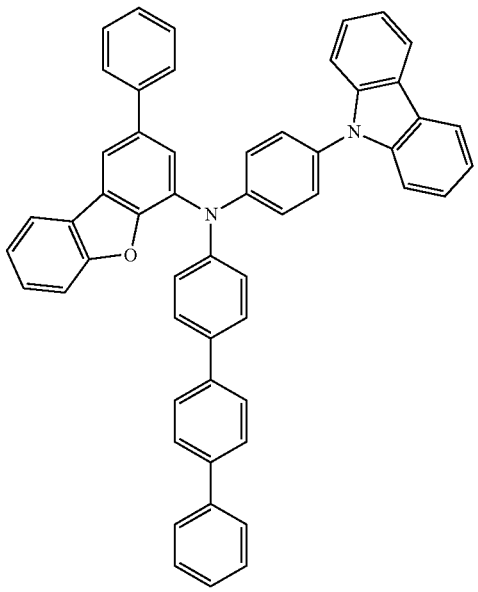
HT44
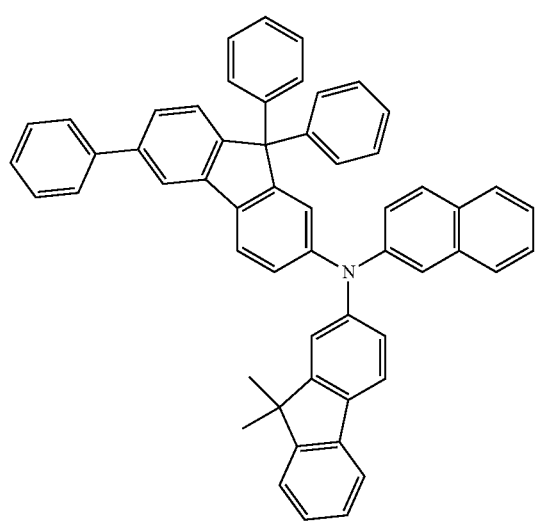
HT45
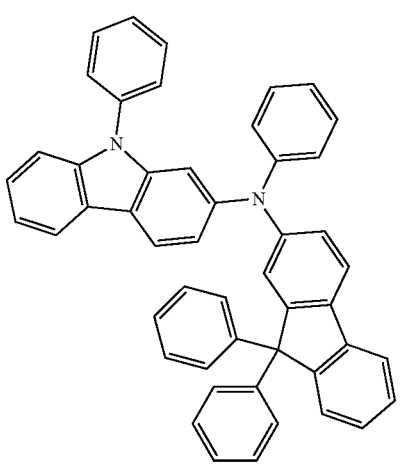

-continued
HT46
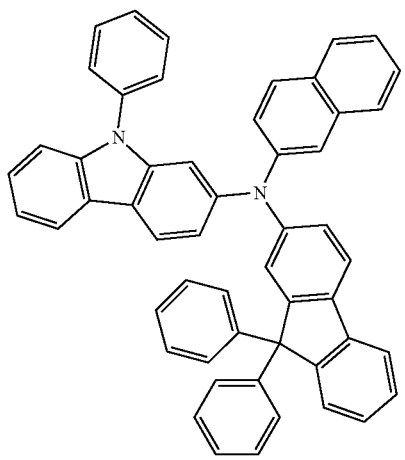
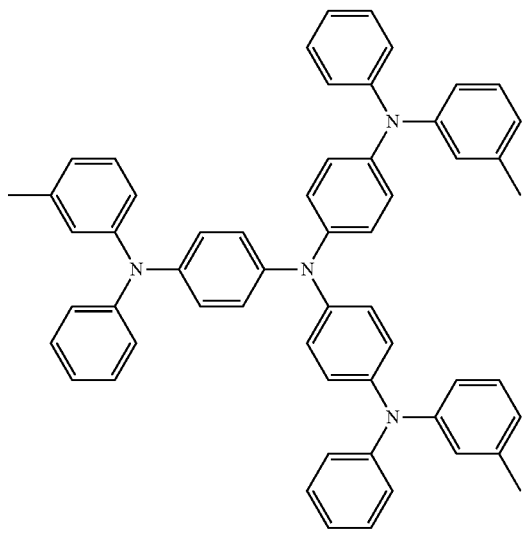
m-MTDATA
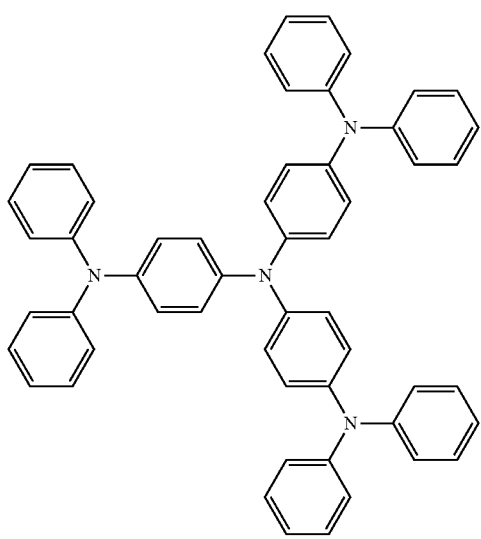
TDATA
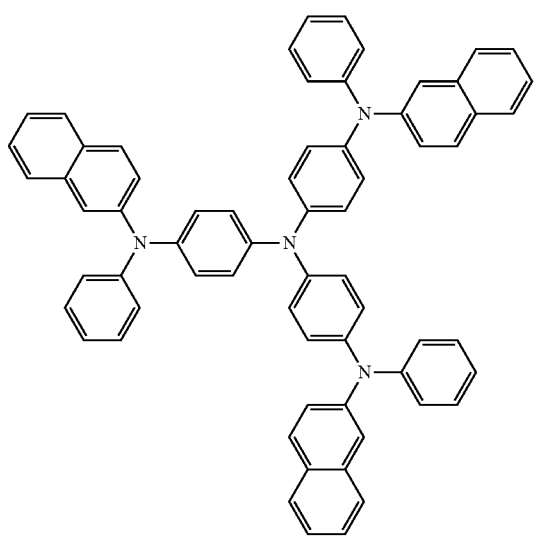
2-TNATA
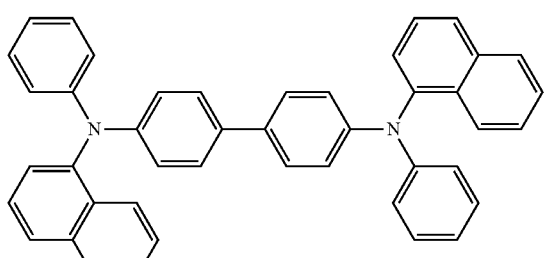
NPB
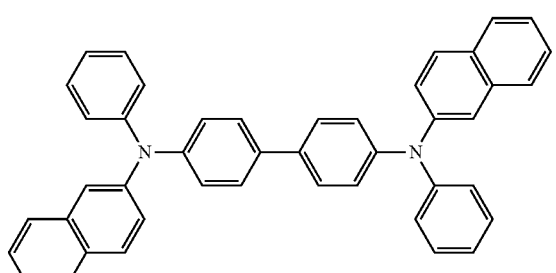
β-NPB -continued

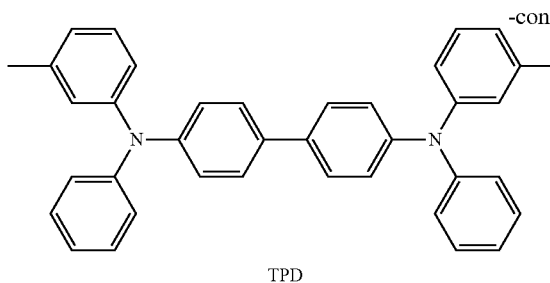
TPD

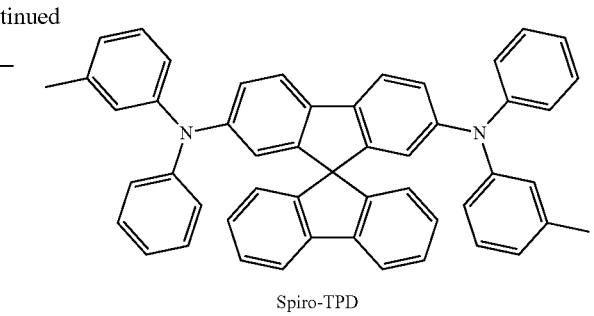
Spiro-TPD

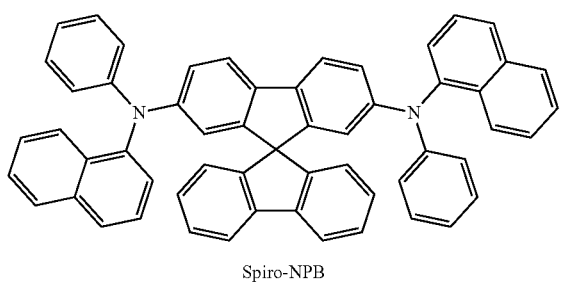
Spiro-NPB

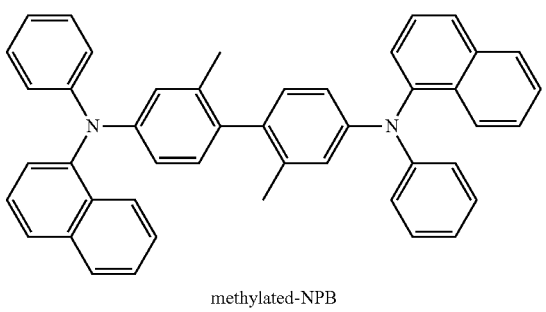
methylated-NPB

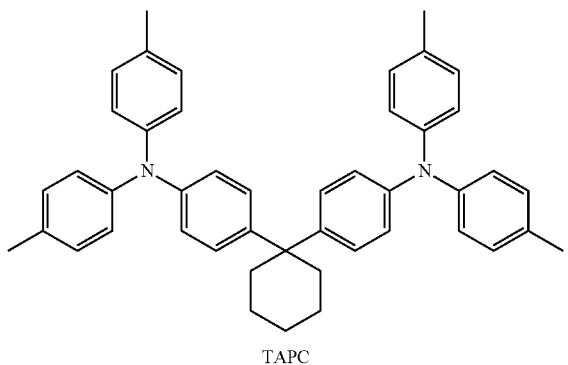
TAPC

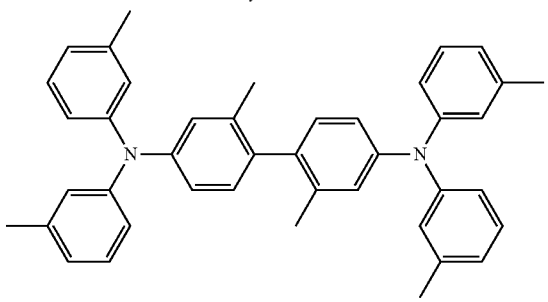
HMTPD

A thickness of the hole transport region may be in a range of about 50 Å to about 10,000 Å, for example, about 100 Å to about 4,000 Å. When the hole transport region includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within the ranges described above, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block or reduce the leakage of electrons from an emission layer to a hole transport region. Materials that may be included in the hole transport region may be included in the emission auxiliary layer and the electron blocking layer.

p-Dopant

The hole transport region may further include, in addition to materials described above, a charge-generation material for the improvement of conductive properties (e.g., electrically conductive properties). The charge-generation material may be uniformly or non-uniformly dispersed in the hole transport region (for example, in the form of a single layer including (e.g., consisting of) a charge-generation material).

The charge-generation material may be, for example, a p-dopant.

In an embodiment, a lowest unoccupied molecular orbital (LUMO) energy level of the p-dopant may be −3.5 eV or less.

In an embodiment, the p-dopant may include a quinone derivative, a cyano group-containing compound, a compound containing element EL1 and element EL2, or any combination thereof.

Examples of the quinone derivative may include TCNQ, F4-TCNQ, and the like.

Examples of the cyano group-containing compound may include HAT-CN, 4-[[2,3-bis[cyano-(4-cyano-2,3,5,6-tetrafluorophenyl)methylidene]cyclopropylidene]-cyanomethyl]-2,3,5,6-tetrafluorobenzonitrile (NDP9), a compound represented by Formula 221, and the like.

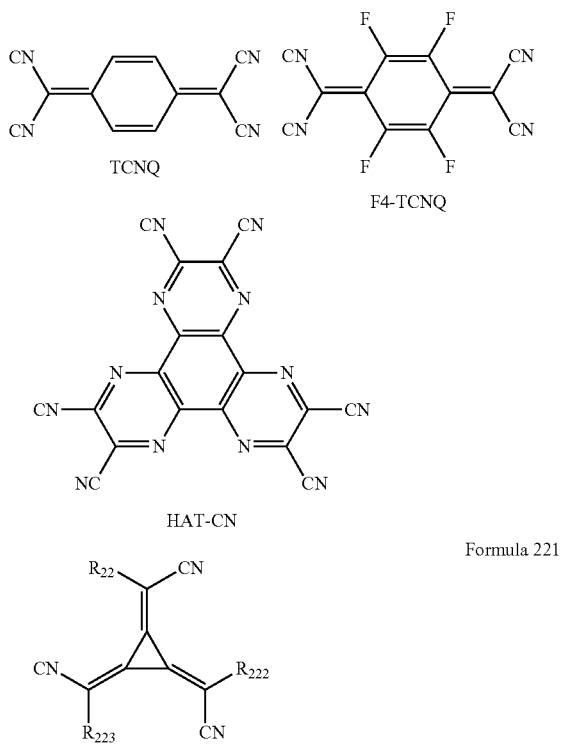

TCNQ

F4-TCNQ

HAT-CN

Formula 221

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one selected from $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; –I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or any combination thereof, and element EL2 may be a non-metal, a metalloid, or any combination thereof.

Examples of the metal include an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid include silicon (Si), antimony (Sb), and tellurium (Te).

Examples of the non-metal include oxygen (O) and halogen (for example, F, Cl, Br, I, etc.).

In one or more embodiments, examples of the compound containing element EL1 and element EL2 include metal oxide, metal halide (for example, metal fluoride, metal chloride, metal bromide, or metal iodide), metalloid halide (for example, metalloid fluoride, metalloid chloride, metalloid bromide, or metalloid iodide), metal telluride, or any combination thereof.

Examples of the metal oxide include tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), and rhenium oxide (for example, $ReO_3$, etc.).

Examples of the metal halide are alkali metal halide, alkaline earth metal halide, transition metal halide, post-transition metal halide, and lanthanide metal halide.

Examples of the alkali metal halide include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide are titanium halide (for example, $TiF_4$, $TiCl_4$, $TiBr_4$, $TiI_4$, etc.), zirconium halide (for example, $ZrF_4$, $ZrCl_4$, $ZrBr_4$, $ZrI_4$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, Re $I_2$, etc.), iron halide (for example, $FeF_2$, $FeCl_2$, $FeBr_2$, $FeI_2$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtCl_2$, $PtBr_2$, $PtI_2$, etc.), copper halide (for example, CuF, CuCl, CuBr, CuI, etc.), silver halide (for example, AgF, AgCl, AgBr, AgI, etc.), and gold halide (for example, AuF, AuCl, AuBr, AuI, etc.).

Examples of the post-transition metal halide include zinc halide (for example, $ZnF_2$, $ZnCl_2$, $ZnBr_2$, $ZnI_2$, etc.), indium halide (for example, $InI_3$, etc.), and tin halide (for example, $SnI_2$, etc.).

Examples of the lanthanide metal halide include YbF, $YbF_2$, $YbF_3$, $SmF_3$, YbCl, $YbCl_2$, $YbCl_3$ $SmCl_3$, YbBr, $YbBr_2$, $YbBr_3$ $SmBr_3$, YbI, $YbI_2$, $YbI_3$, and $SmI_3$.

An example of the metalloid halide includes antimony halide (for example, $SbCl_5$, etc.).

Examples of the metal telluride include alkali metal telluride (for example, $Li_2Te$, $Na_2Te$, $K_2Te$, $Rb_2Te$, $Cs_2Te$, etc.), alkaline earth metal telluride (for example, BeTe, MgTe, CaTe, SrTe, BaTe, etc.), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), post-transition metal telluride (for example, ZnTe, etc.), and lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer in Interlayer 130

When the light-emitting device 10 is a full-color light-emitting device, the emission layer may be patterned into a red emission layer, a green emission layer, and/or a blue emission layer, according to a subpixel. In one or more embodiments, the emission layer may have a stacked structure of two or more layers of a red emission layer, a green emission layer, and a blue emission layer, in which the two or more layers contact (e.g., physically contact) each other or are separated from each other. In one or more embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

The amount of the dopant in the emission layer may be from about 0.01 to about 15 parts by weight based on 100 parts by weight of the host.

In one or more embodiments, the emission layer may include a quantum dot.

In one or more embodiments, the emission layer may include a delayed fluorescence material. The delayed fluorescence material may act as a host or a dopant in the emission layer.

A thickness of the emission layer may be in a range of about 100 Å to about 1,000 Å, for example, about 200 Å to about 600 Å. When the thickness of the emission layer is within the range described above, excellent light-emission characteristics may be obtained without a substantial increase in driving voltage.

Host

The host may include a compound represented by Formula 301:

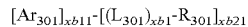

Formula 301 wherein, in Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, -D, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), xb21 may be an integer from 1 to 5, and $Q_{301}$ to $Q_{303}$ are each the same as described in connection with $Q_1$.

In an embodiment, when xb11 in Formula 301 is 2 or more, two or more of $Ar_{301}$(s) may be linked to each other via a single bond.

In one or more embodiments, the host may include a compound represented by Formula 301-1, a compound represented by Formula 301-2, or any combination thereof:

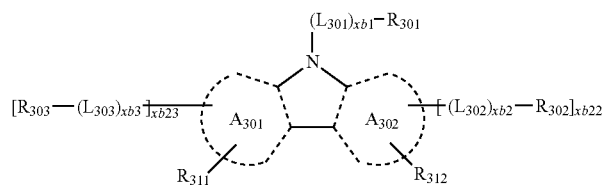

Formula 301-1

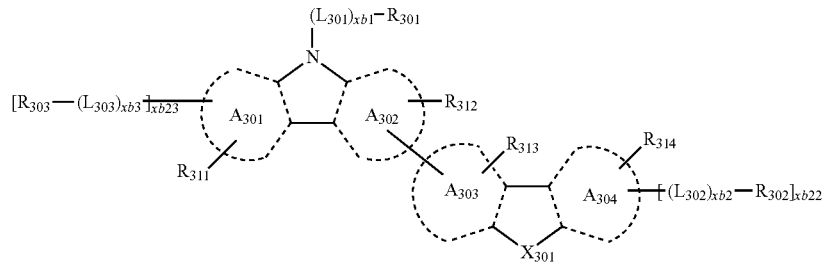

Formula 301-2 wherein, in Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-[($L_{304}$)$_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ are each the same as described in the present specification, $L_{302}$ to $L_{304}$ are each independently the same as described in connection with $L_{301}$, xb2 to xb4 are each independently the same as described in connection with xb1, and $R_{302}$ to $R_{305}$ and $R_{311}$ to $R_{314}$ are each the same as described in connection with $R_{301}$.

In one or more embodiments, the host may include an alkali earth metal complex, a post-transition metal complex, or any combination thereof. In an embodiment, the host may include a Be complex (for example, Compound H55), an Mg complex, a Zn complex, or any combination thereof.

In one or more embodiments, the host may include one selected from Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or any combination thereof:

H1
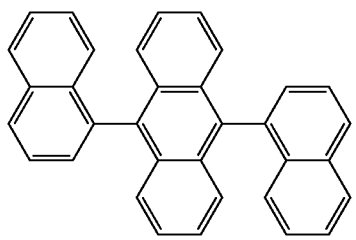

H2
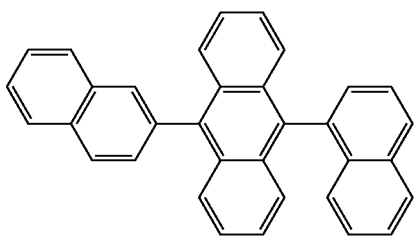

H3
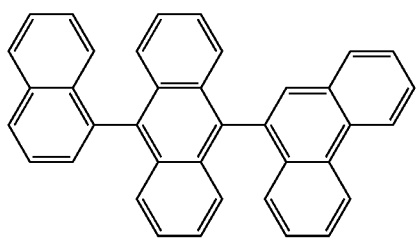

H4
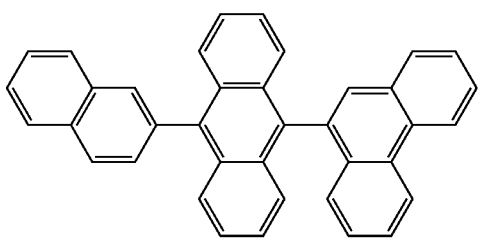

H5
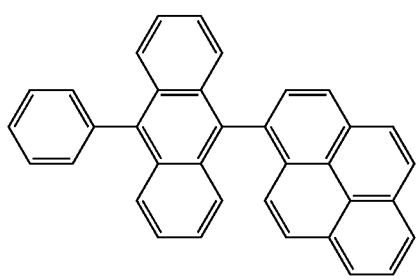

H6
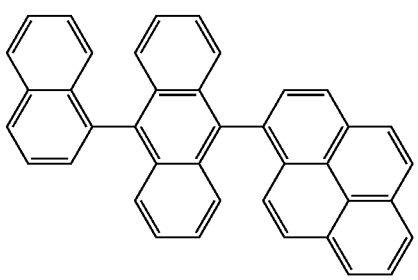

H7
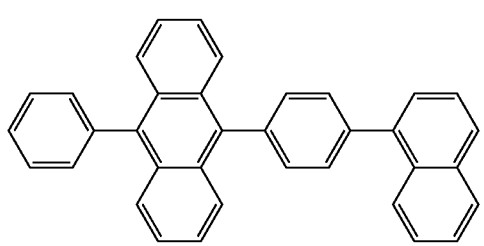

H8
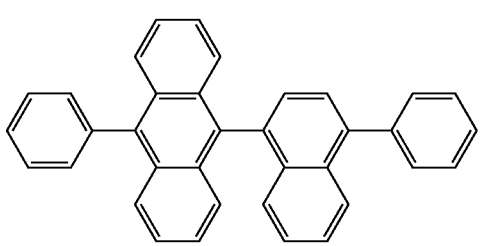

H9
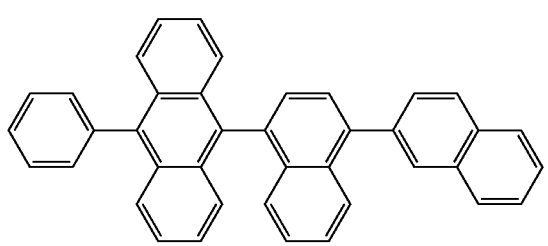

H10
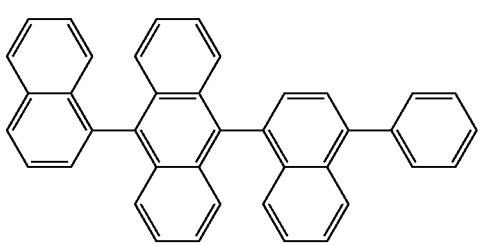

-continued
H11
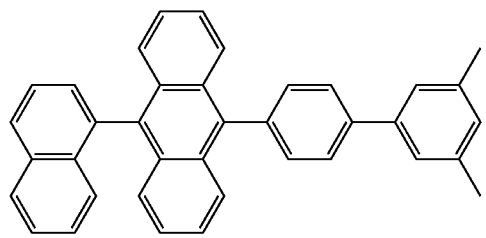
H12
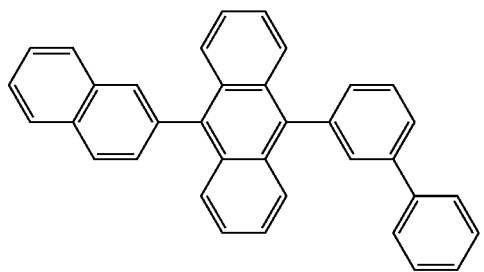
H13
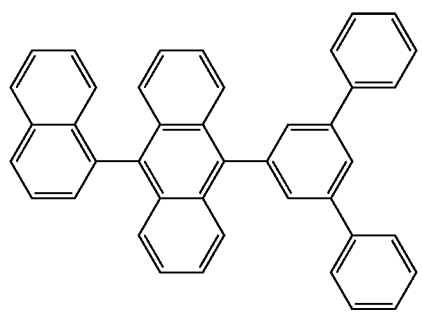
H14
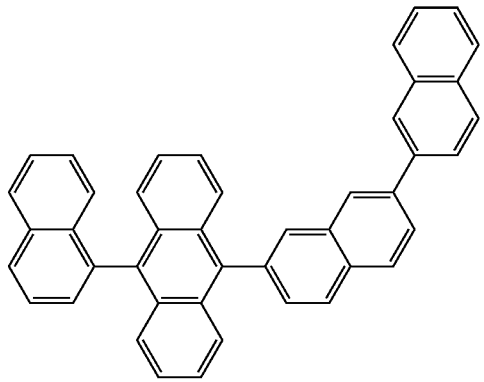
H15
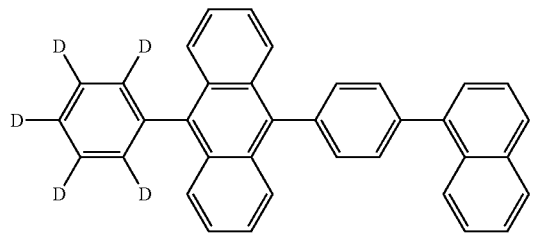
H16
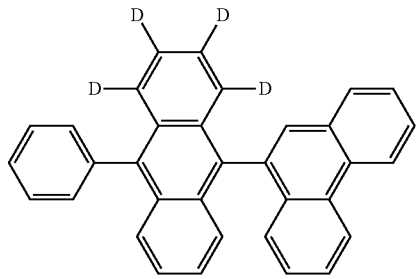
H17
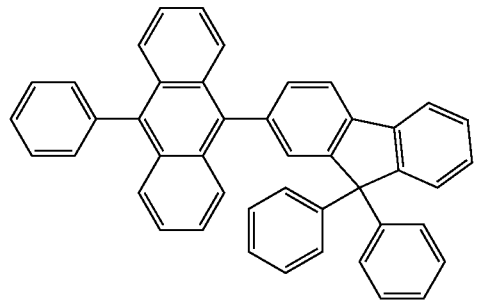
H18
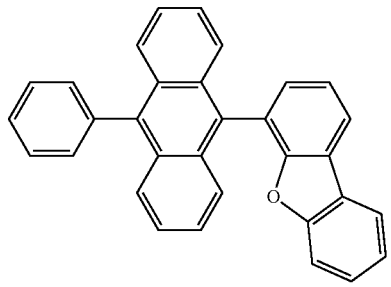
H19
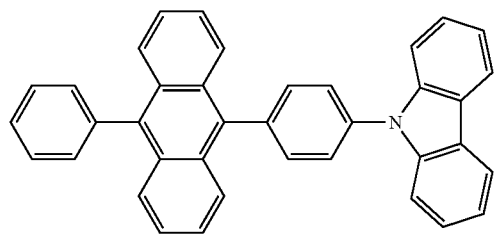
H20
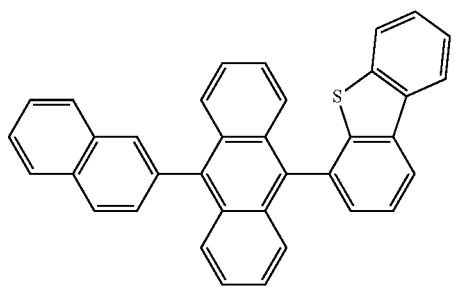

-continued
H21
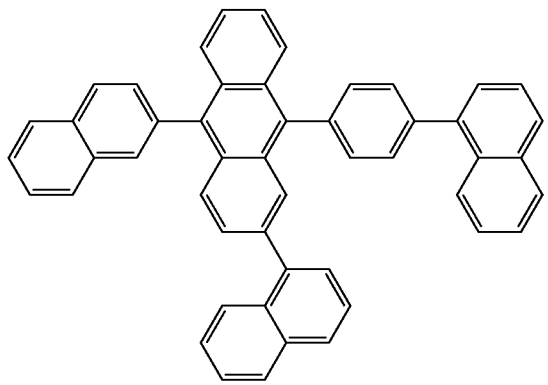
H22
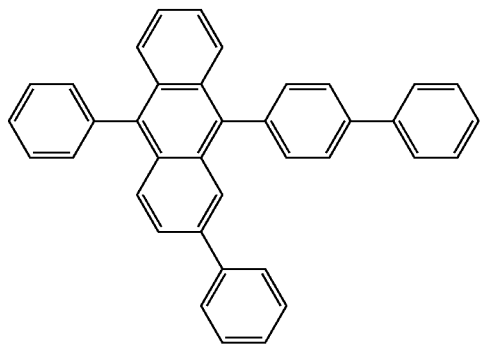
H23
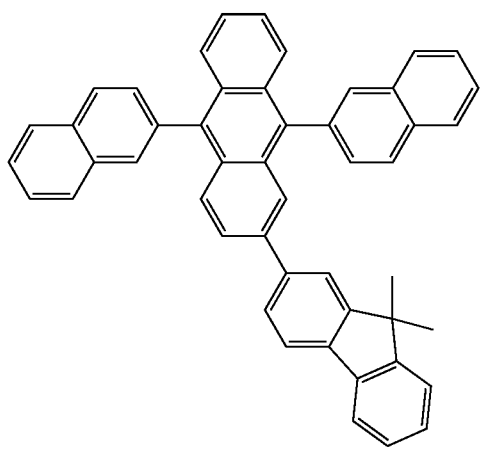
H24
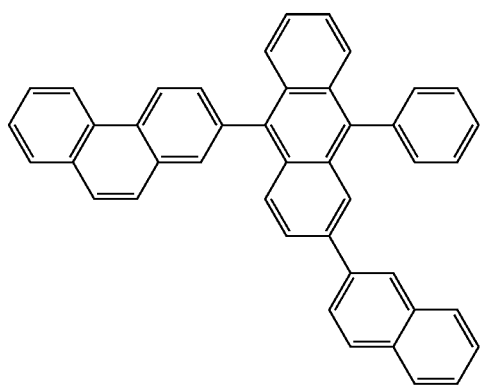
H25
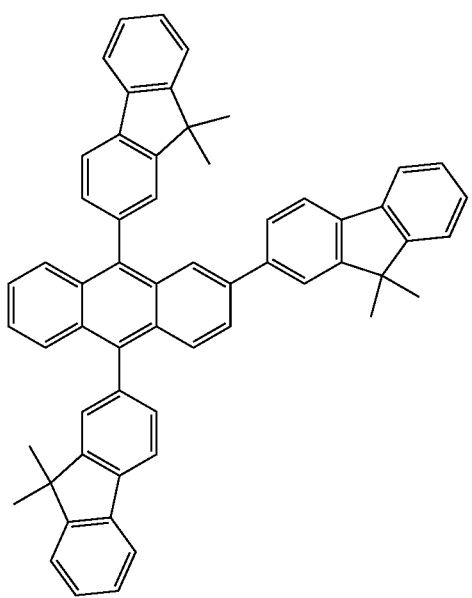
H26
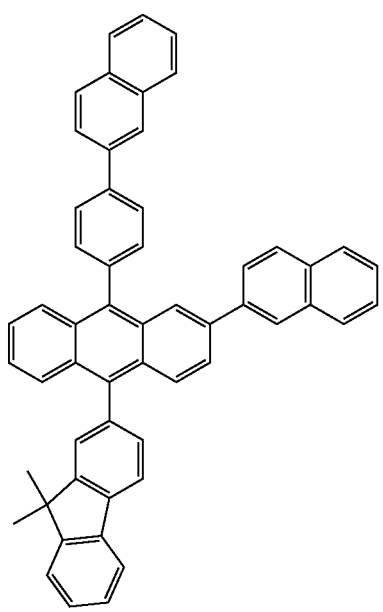

-continued
H27
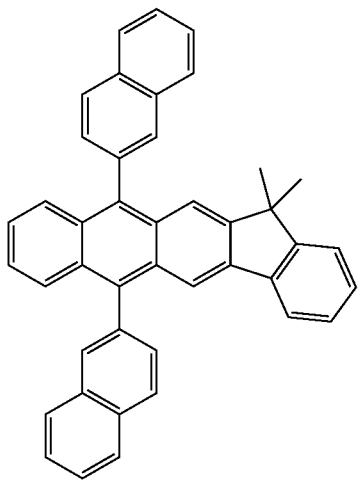
H28
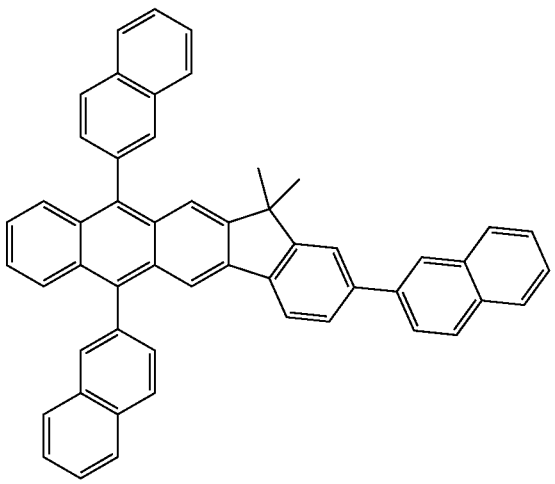
H29
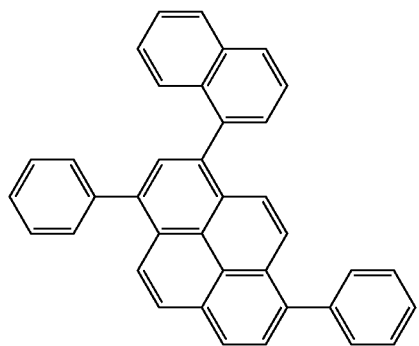
H30
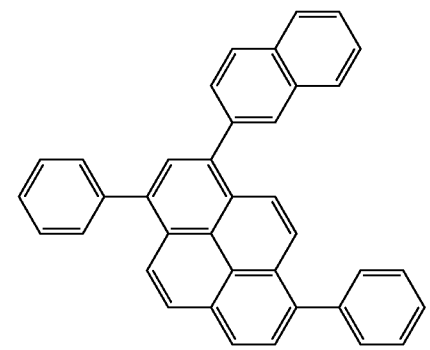
H31
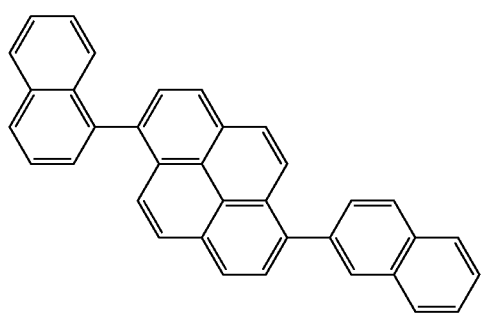
H32
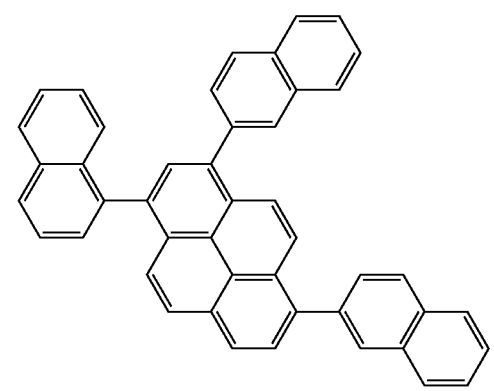
H33
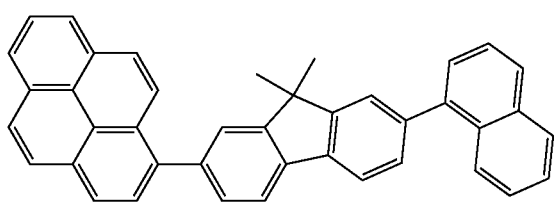
H34
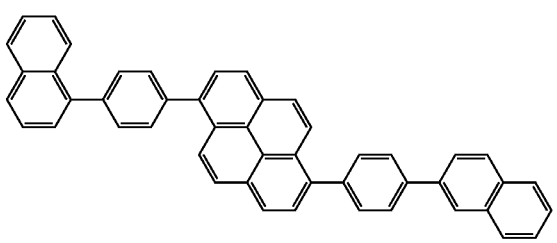

-continued
H35
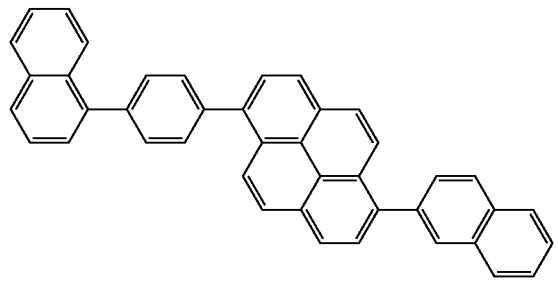
H36
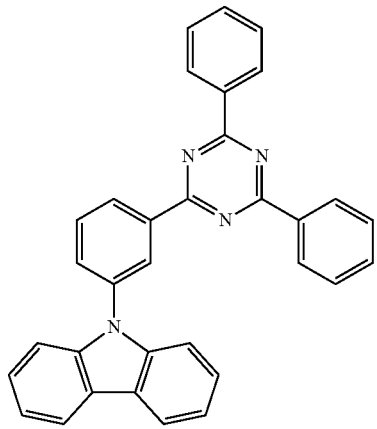
H37
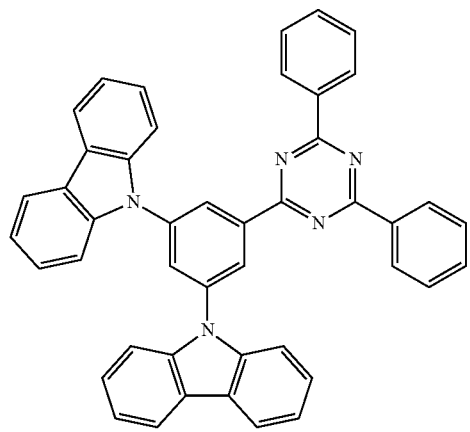
H38
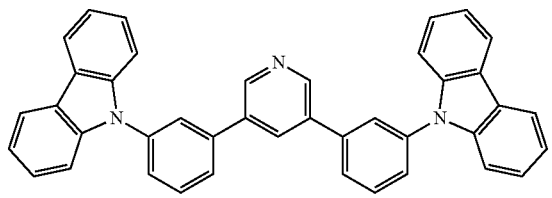
H39
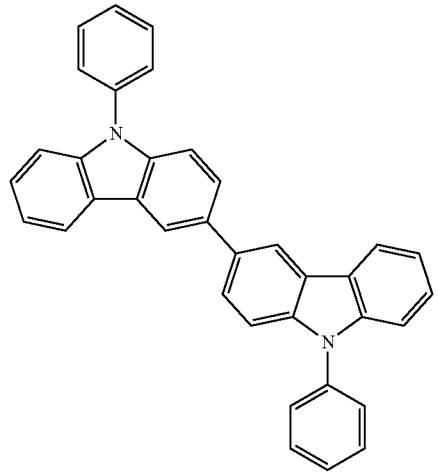
H40
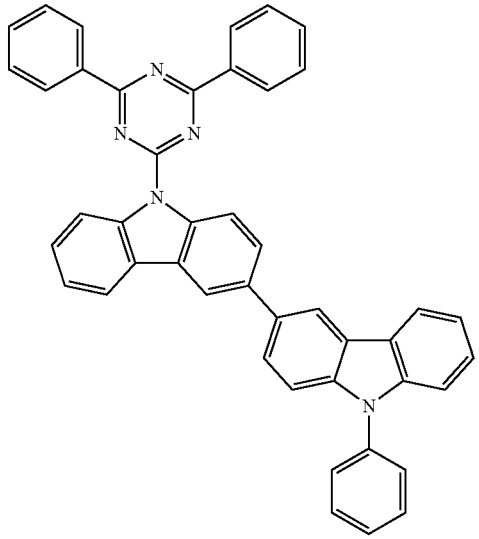

-continued
H41
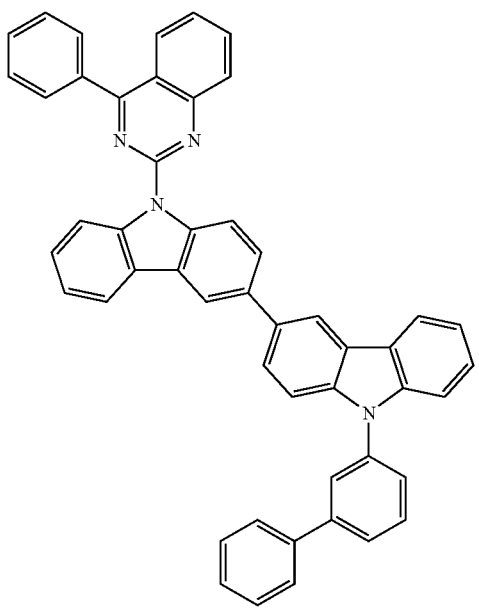
H42
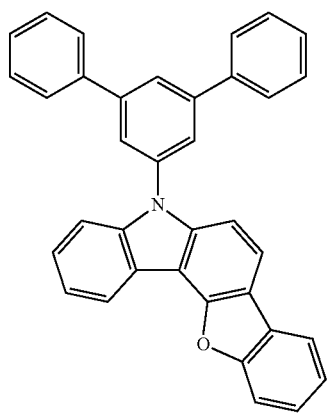
H43
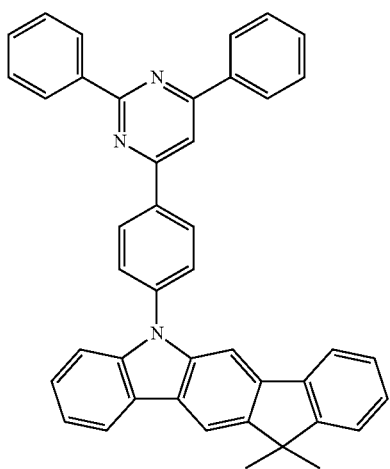
H44
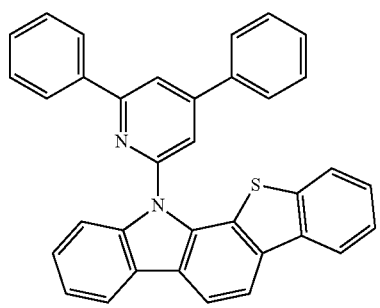
H45
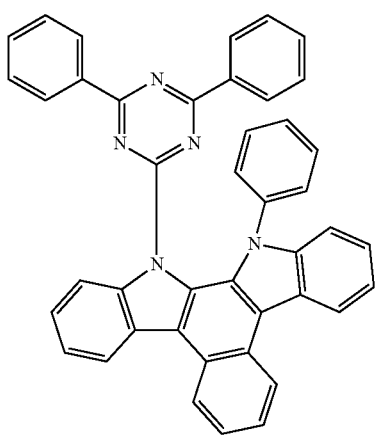
H46
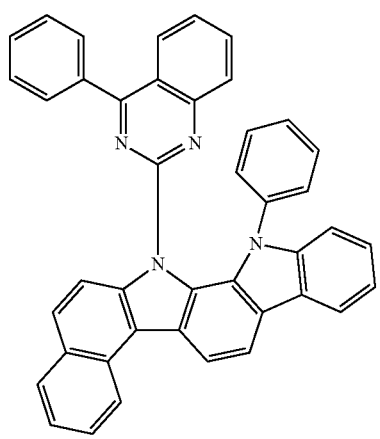

-continued
H47
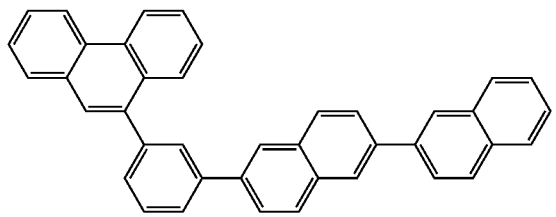
H48
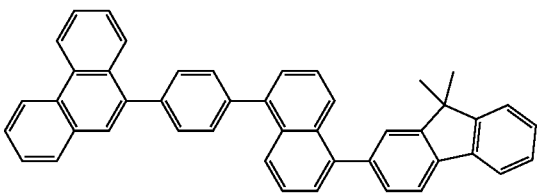
H49
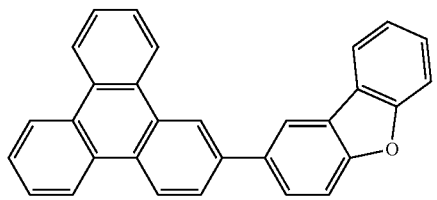
H50
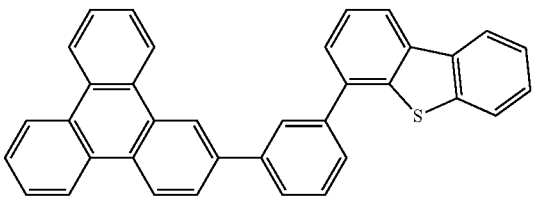
H51
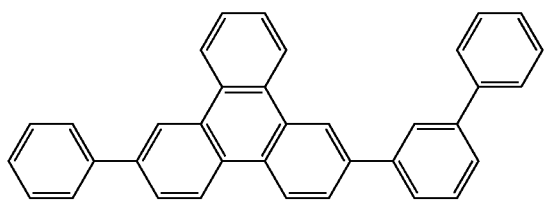
H52
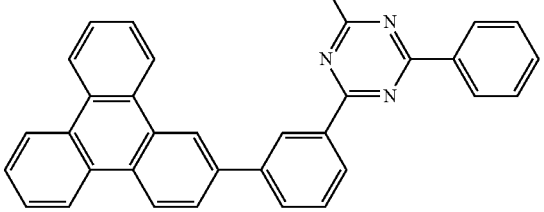
H53
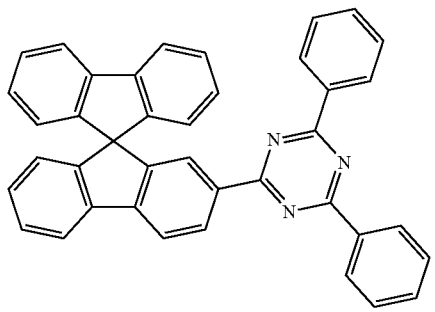
H54
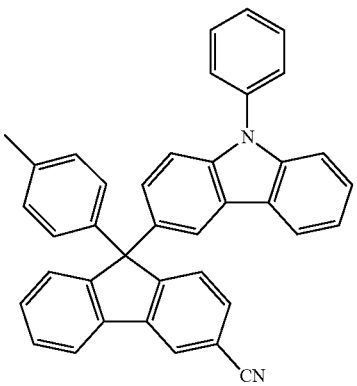
H55
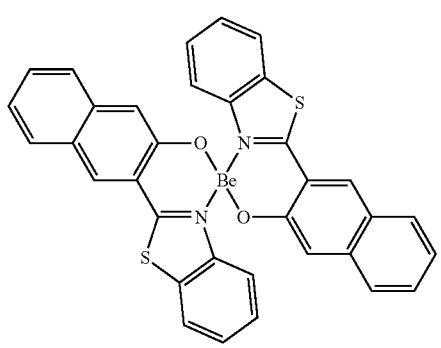
H56
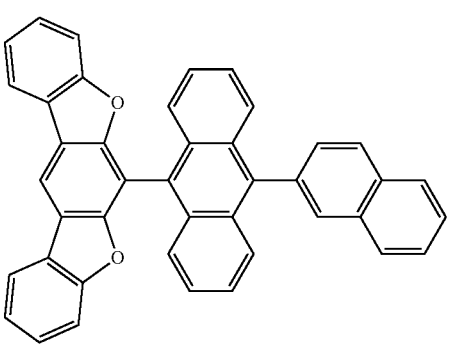

-continued
H57
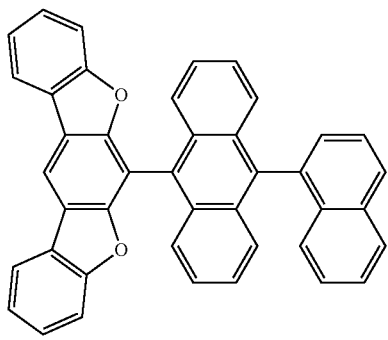
H58
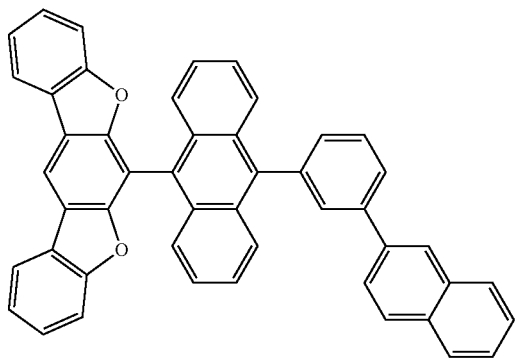
H59
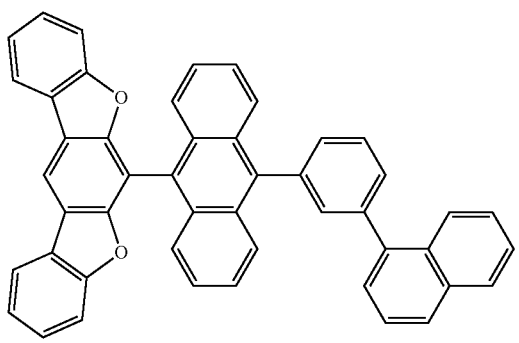
H60
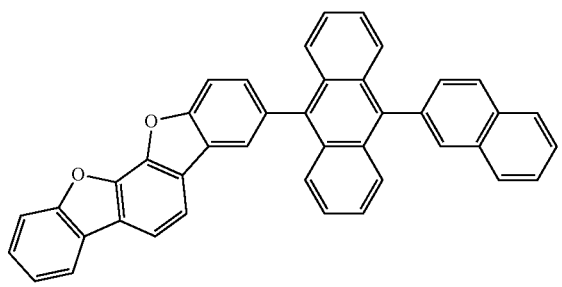
H61
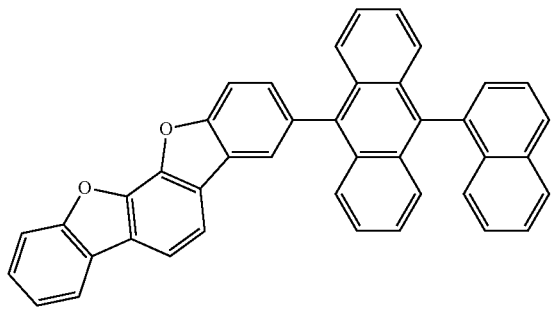
H62
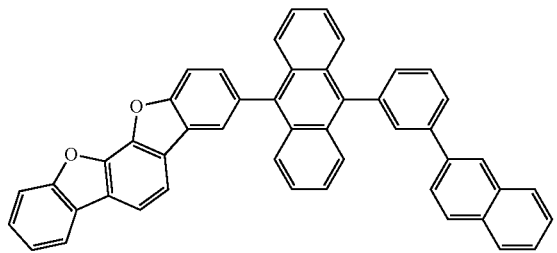
H63
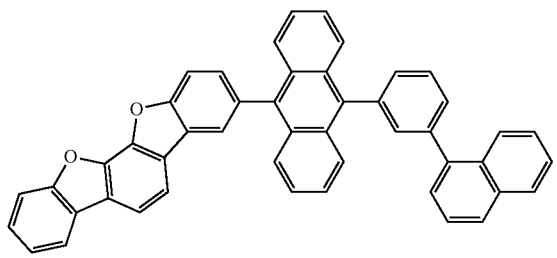
H64
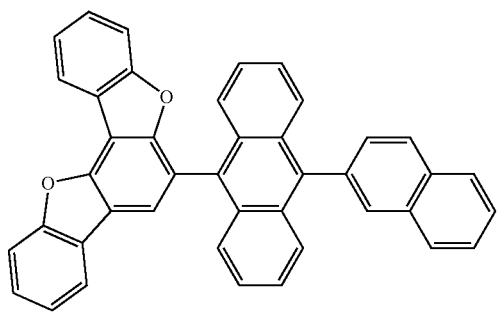

-continued
H65
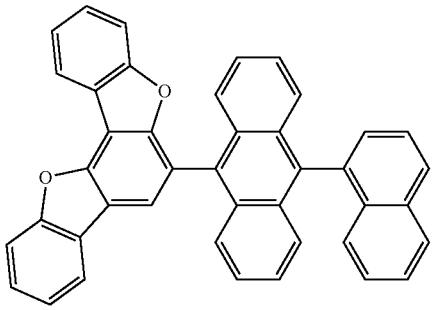
H66
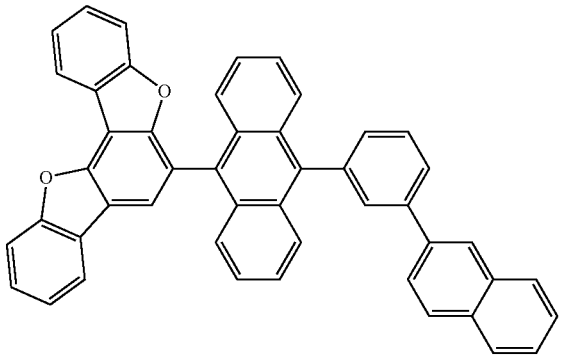
H67
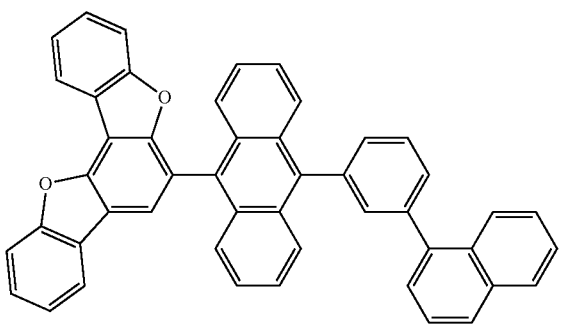
H68
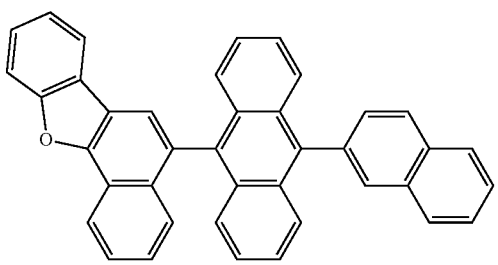
H69
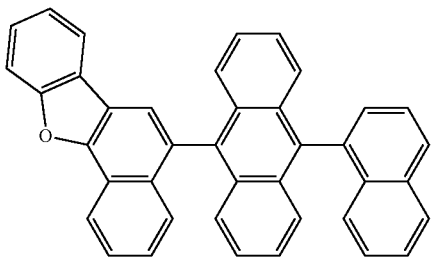
H70
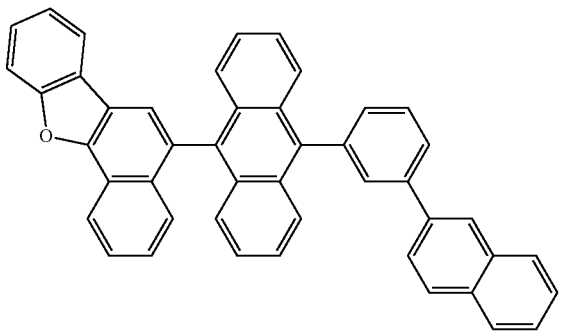
H71
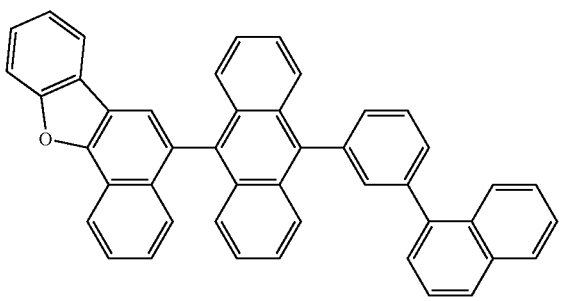
H72
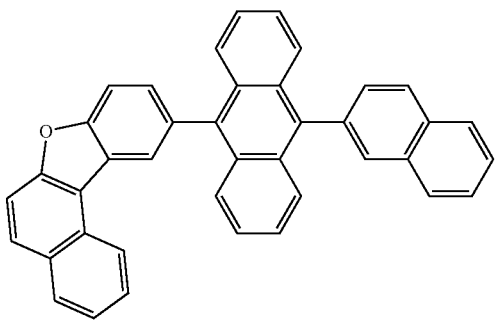

-continued
H73
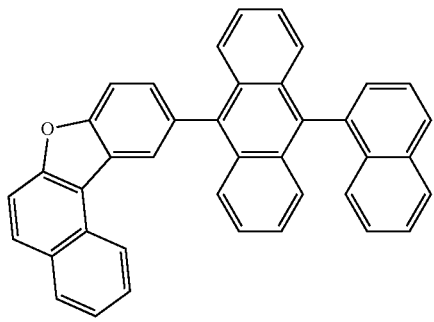
H74
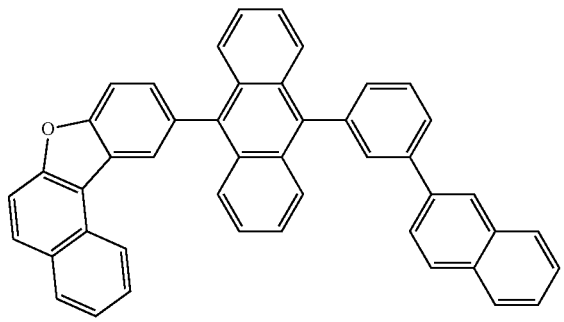
H75
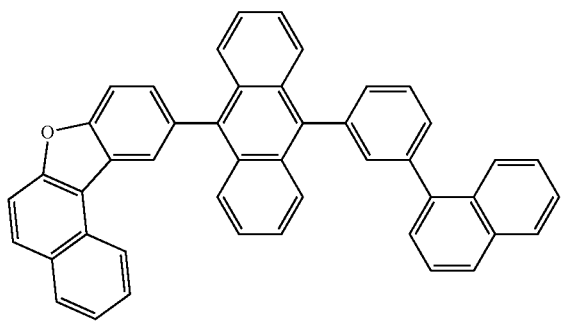
H76
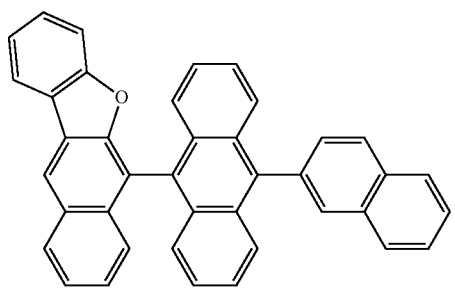
H77
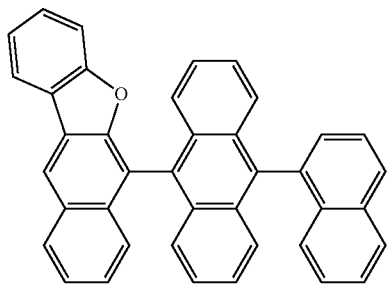
H78
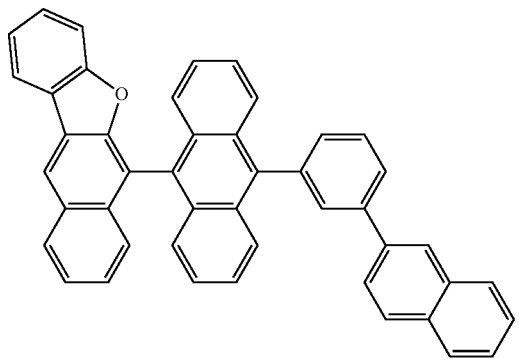
H79
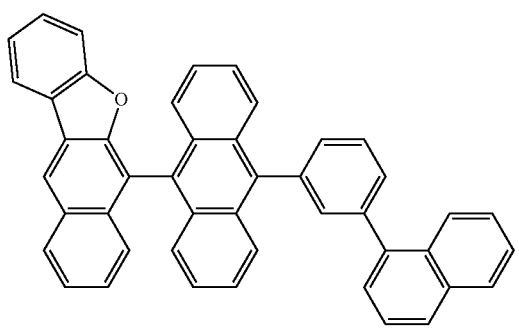
H80
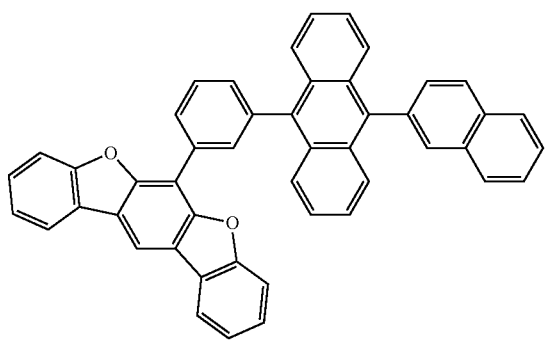

H81
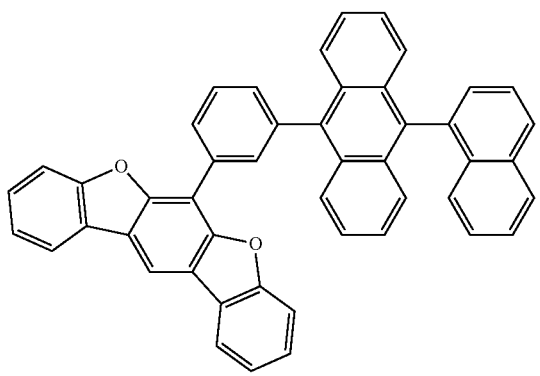
H82
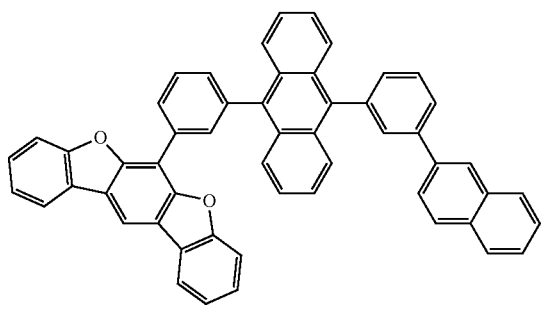
H83
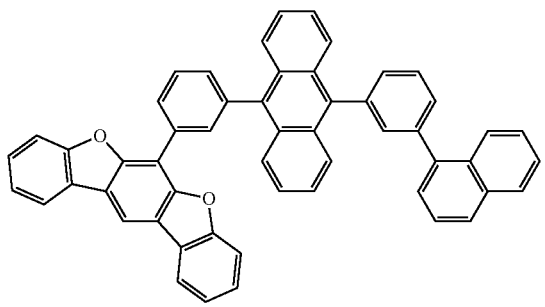
H84
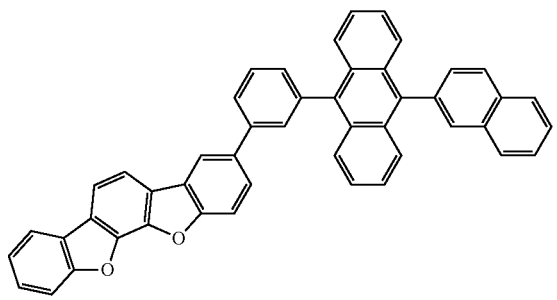
H85
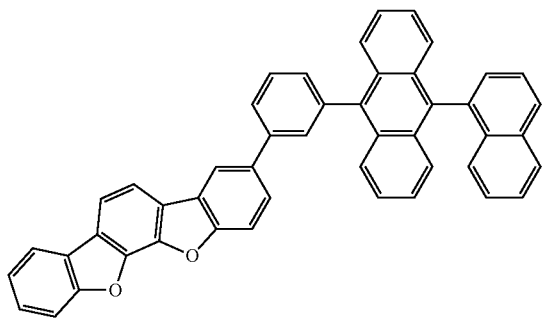
H86
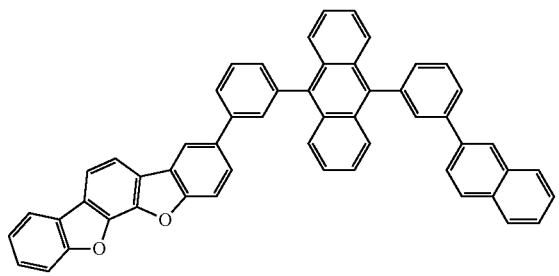
H87
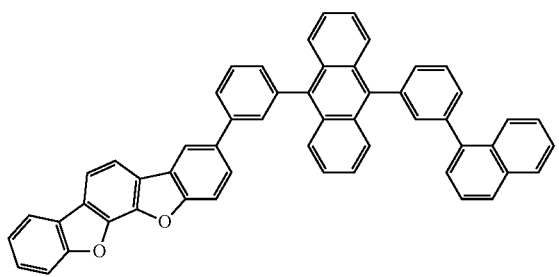
H88
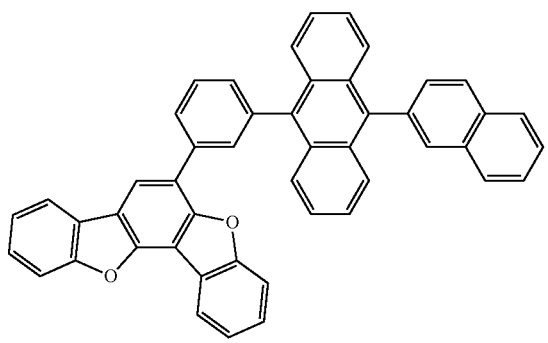

-continued
H89
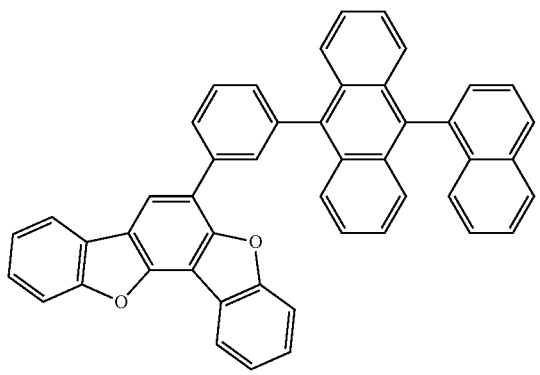
H90
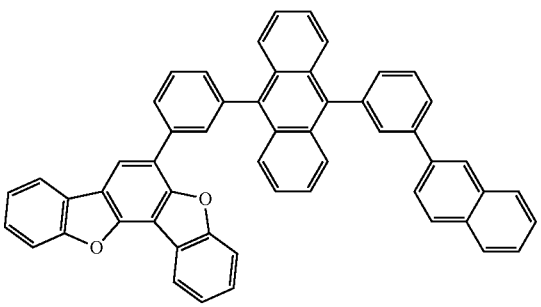
H91
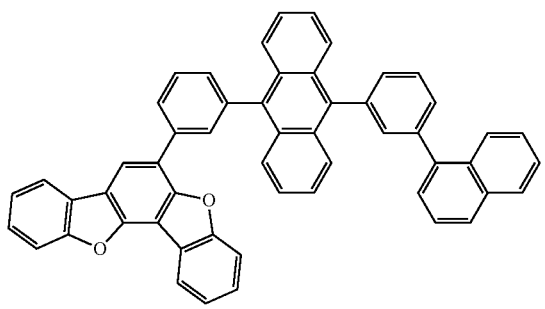
H92
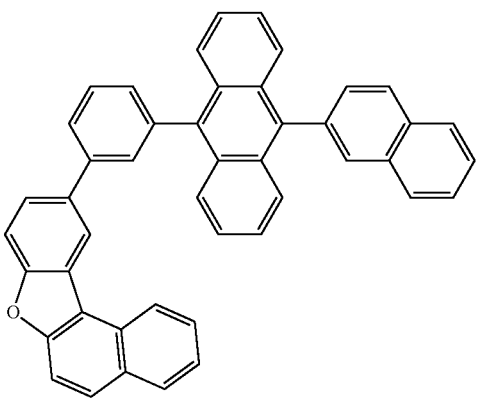
H93
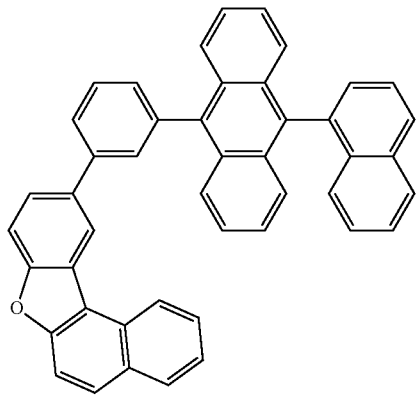
H94
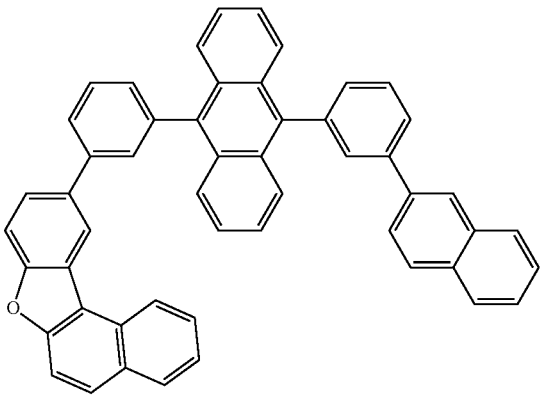
H95
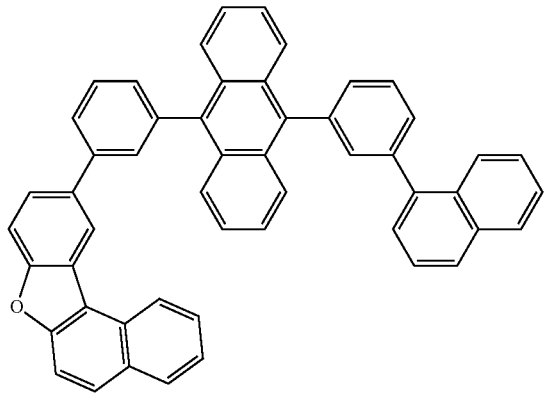
H96
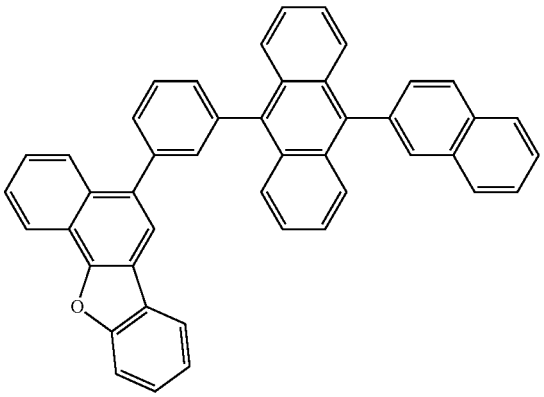

-continued
H97
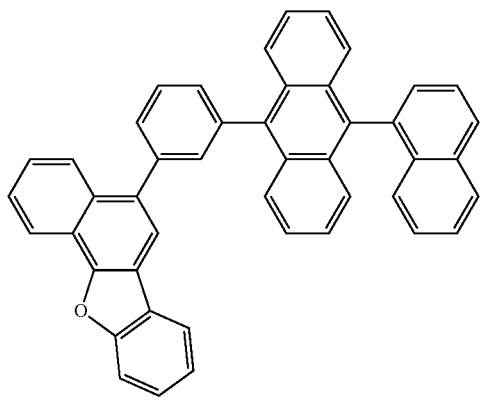
H98
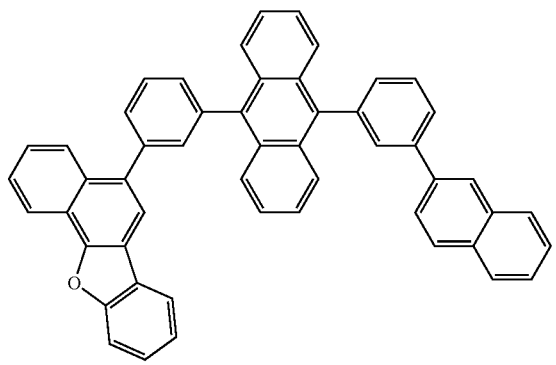
H99
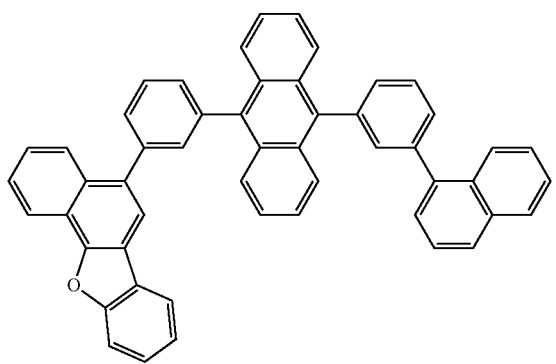
H100
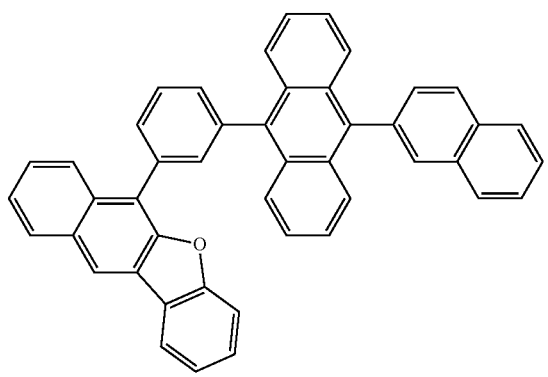
H101
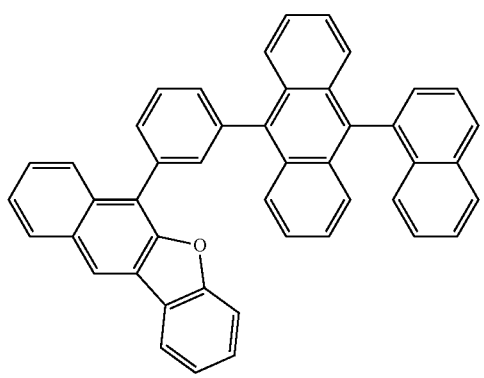
H102
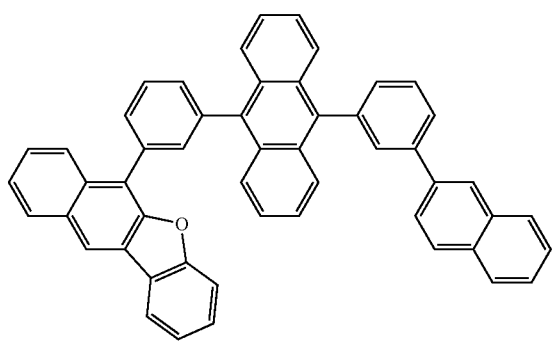

-continued
H103
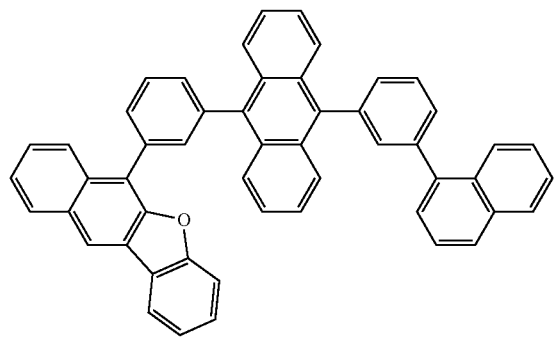
H104
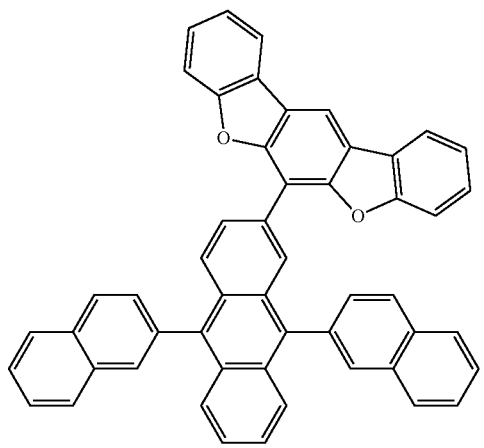
H105
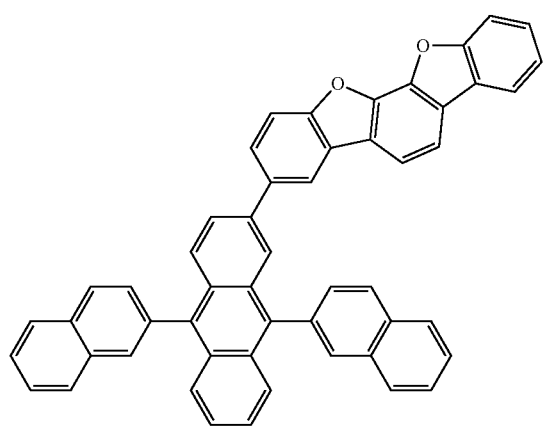
H106
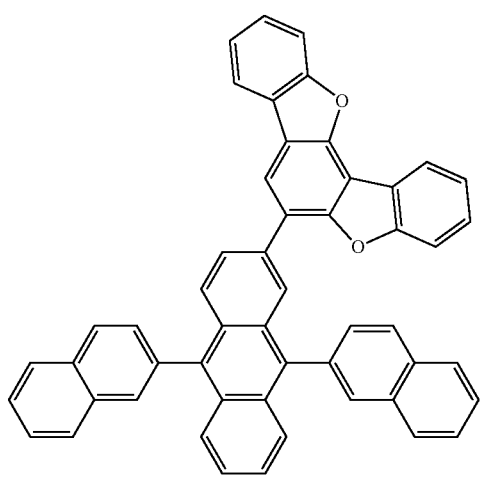
H107
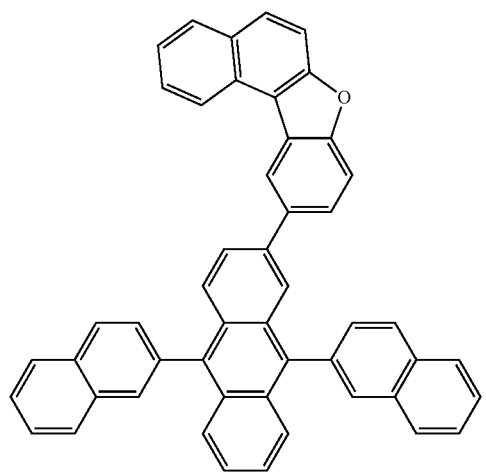
H108
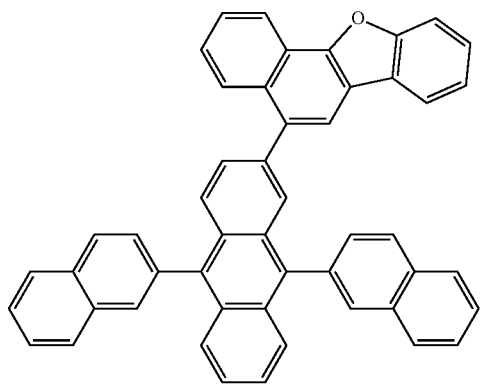

-continued
H109
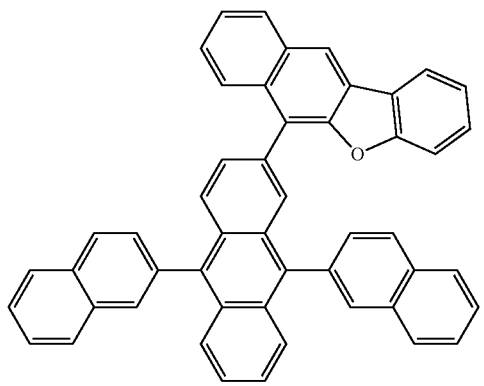
H110
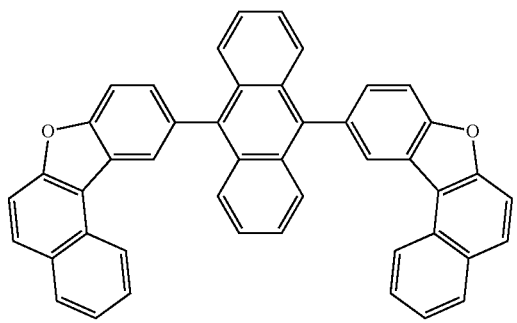
H111
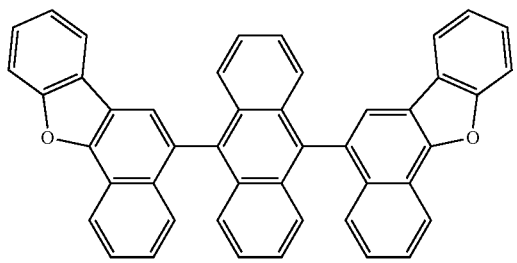
H112
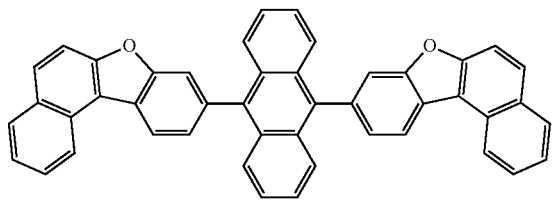
H113
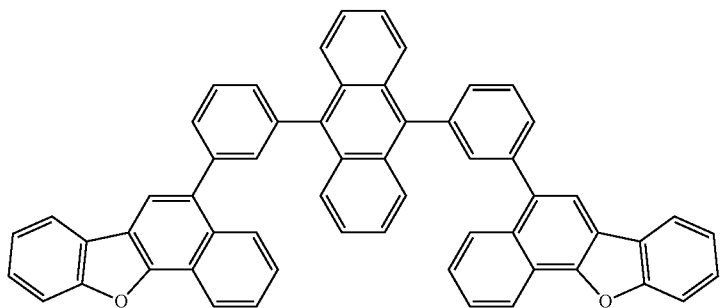
H114
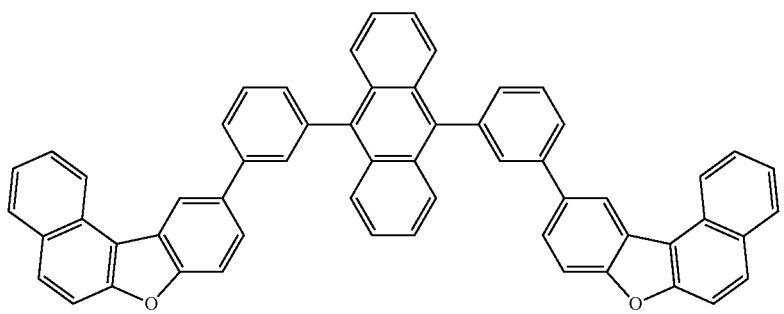

-continued
H115
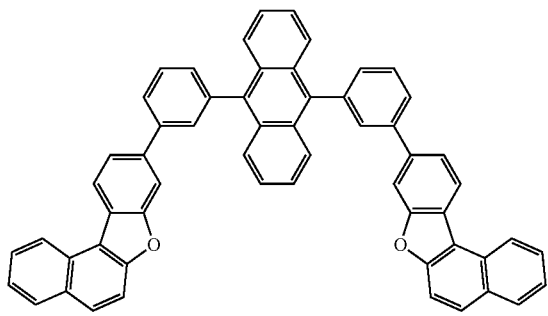
H116
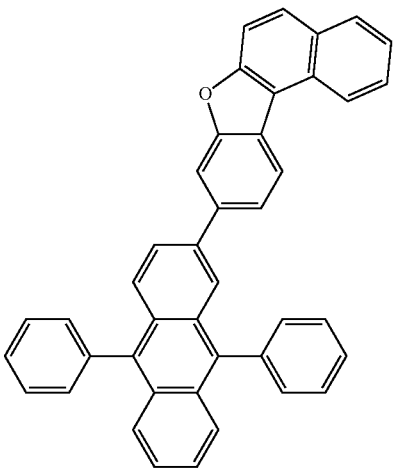
H117
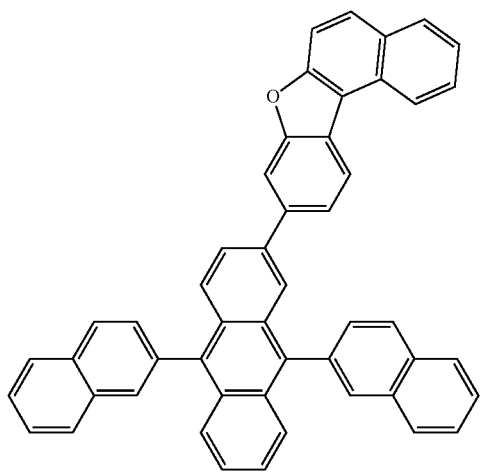
H118
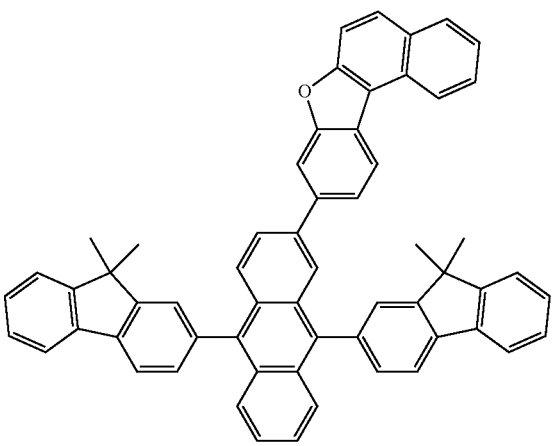
H119
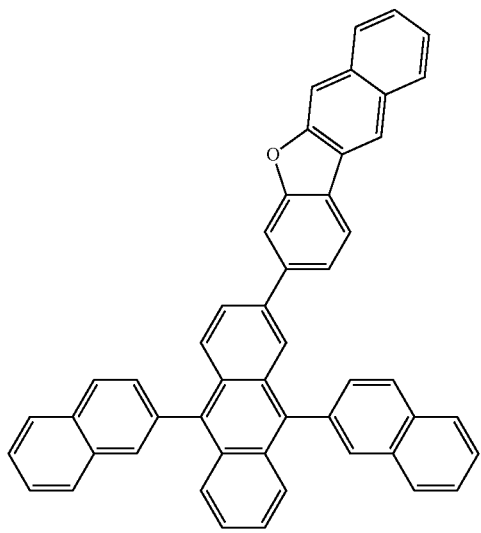
H120
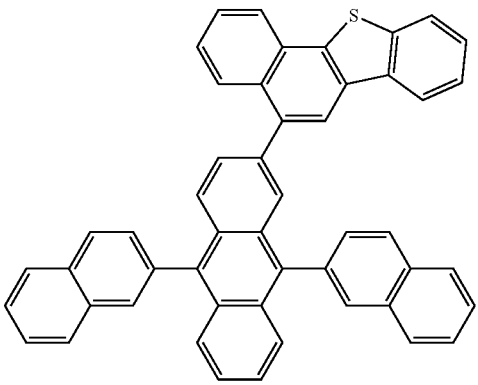

H121

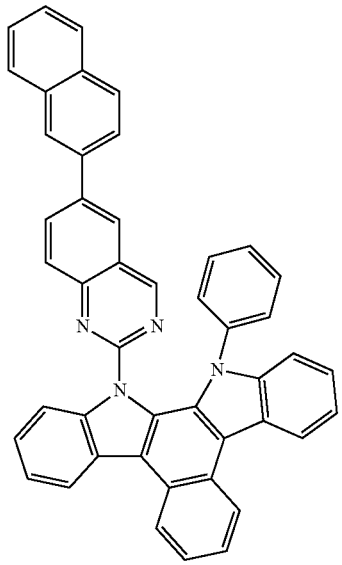

H122

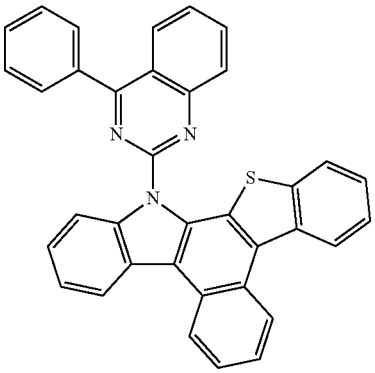

H123

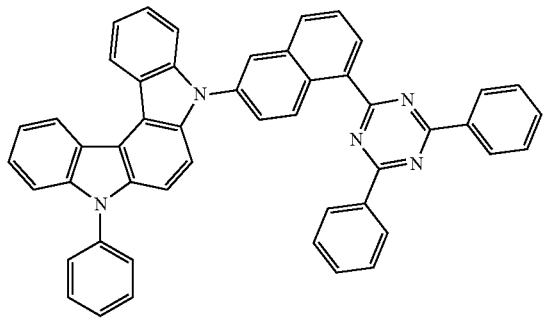

H124

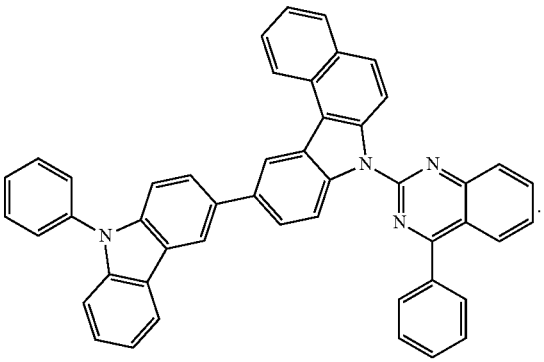

Phosphorescent Dopant

The phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In an embodiment, the phosphorescent dopant may include an organometallic compound represented by Formula 401:

$$M(401)_{xc1}(L_{402})_{xc2}$$ Formula 401

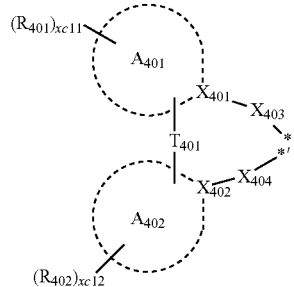

Formula 402 wherein, in Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is 2 or more, two or more of $L_{401}$(s) may be identical to or different from each other, $L_{402}$ may be an organic ligand, and xc2 may be 0, 1, 2, 3, or 4, wherein when xc2 is 2 or more, two or more of $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)*', *—C($Q_{411}$)($Q_{412}$)-*', *—C($Q_{411}$)=C($Q_{412}$)-*', *—C($Q_{411}$)=*', or *=C($Q_{411}$)=*', $X_{403}$ and $X_{404}$ may each independently be a chemical bond (for example, a covalent bond (e.g., a single bond) or a coordination bond (e.g., coordinate covalent bond or a dative bond)), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are each the same as described in connection with $Q_1$, $R_{401}$ and $R_{402}$ may each independently be hydrogen, -D, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ are each the same as described in connection with $Q_1$, xc11 and xc12 may each independently be an integer from 0 to 10, and

* and *' in Formula 402 each indicate a binding site to M in Formula 401.

In an embodiment, in Formula 402, i) $X_{401}$ may be nitrogen, and $X_{402}$ may be carbon, or ii) each of $X_{401}$ and $X_{402}$ may be nitrogen.

In one or more embodiments, when xc1 in Formula 402 is 2 or more, two ring $A_{401}$(s) in two or more of $L_{401}$(s) may be optionally linked to each other via $T_{402}$, which is a linking group, and two ring $A_{402}$(s) may optionally be linked to each other via $T_{403}$, which is a linking group (see Compounds PD1 to PD4 and PD7). $T_{402}$ and $T_{403}$ are each the same as described in connection with $T_{401}$.

$L_{402}$ in Formula 401 may be an organic ligand. In an embodiment, $L_{402}$ may include a halogen group, a diketone group (for example, an acetylacetonate group), a carboxylic acid group (for example, a picolinate group), —C(=O), an isonitrile group, —CN group, a phosphorus group (for example, a phosphine group, a phosphite group, etc.), or any combination thereof.

The phosphorescent dopant may include, for example, one or more selected from Compounds PD1 to PD39, or any combination thereof:

PD1

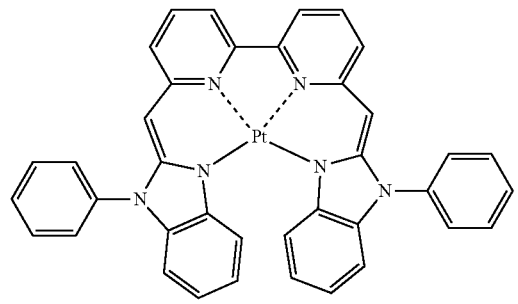

PD2

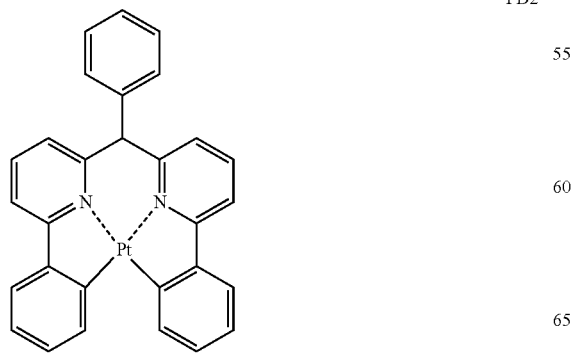

PD3

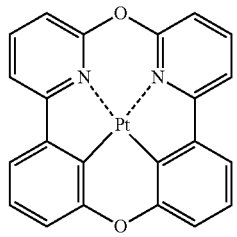

PD4

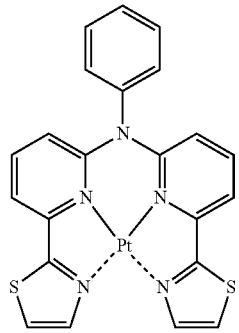

PD5

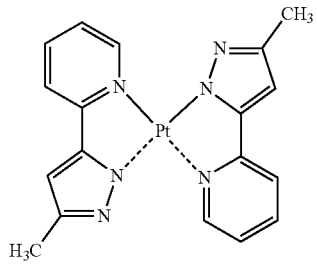

PD6

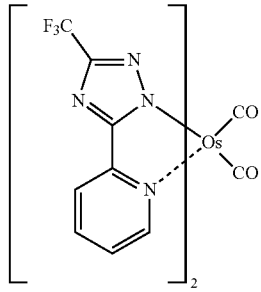

PD7

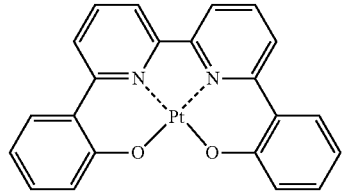

PD8

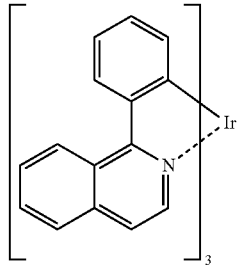

PD9
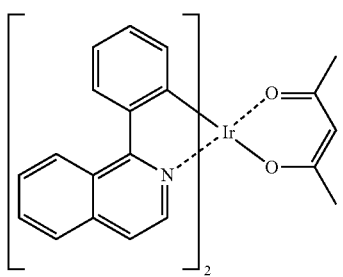
PD10
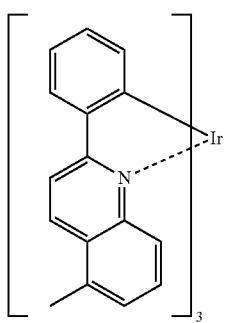
PD11
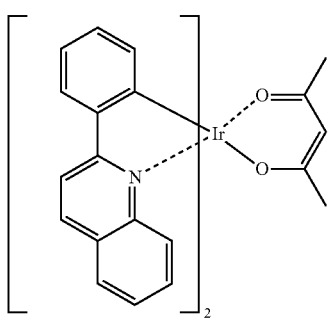
PD12
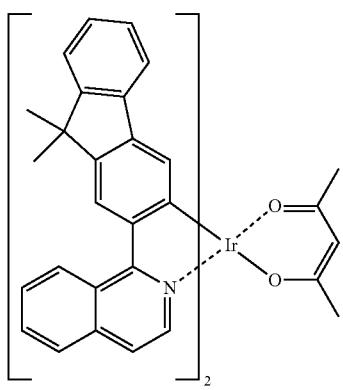
PD13
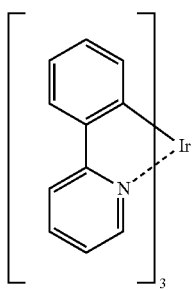
PD14
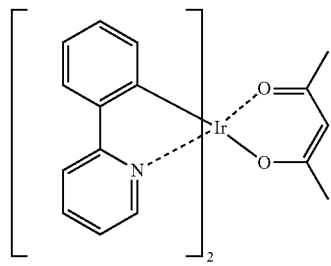
PD15
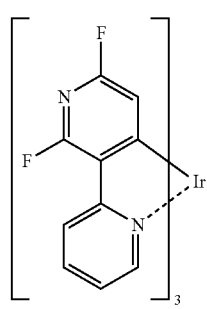
PD16
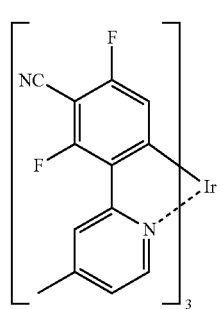
PD17
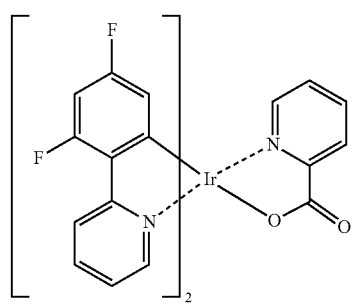
PD18
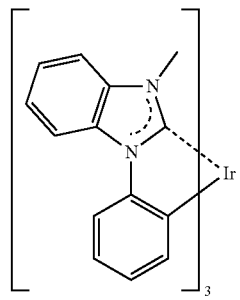

-continued
PD19
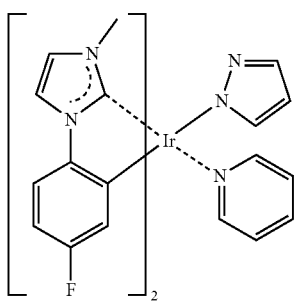
PD20
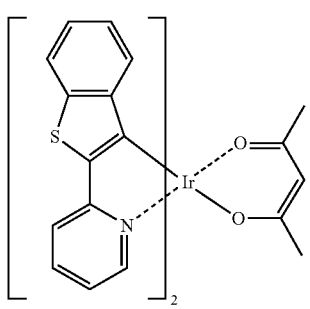
PD21
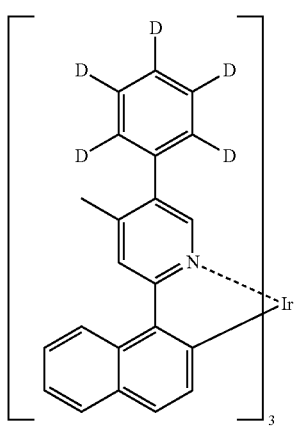
PD22
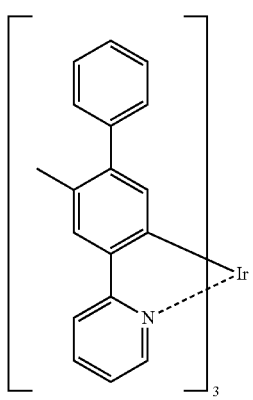
-continued
PD23
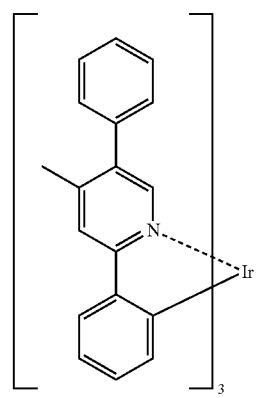
PD24
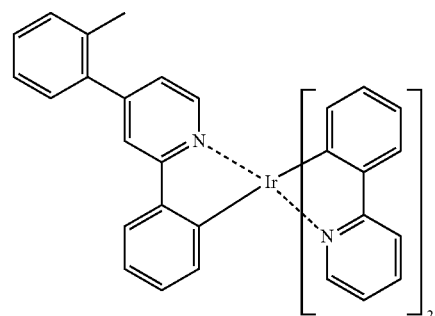
PD25
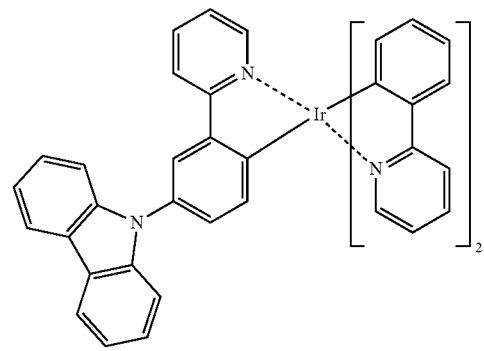
PD26
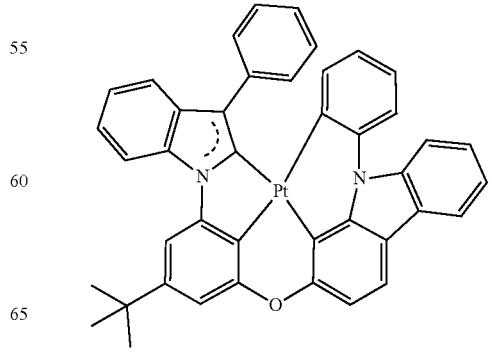

PD27
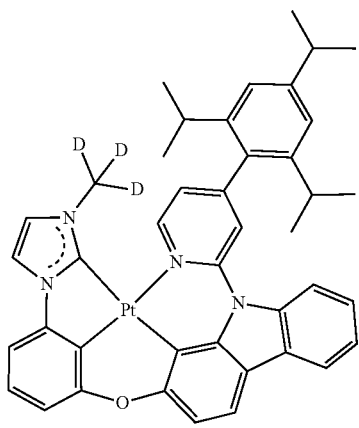
PD28
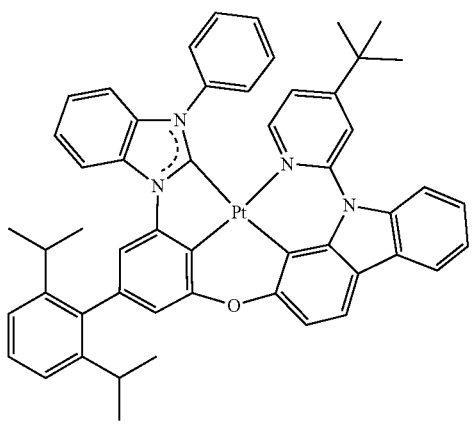
PD29
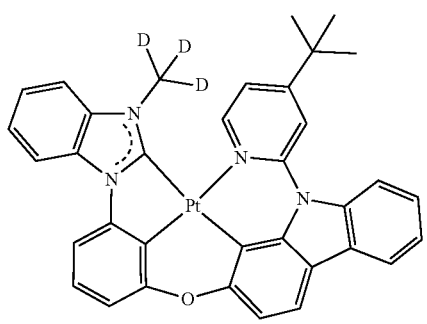
PD30
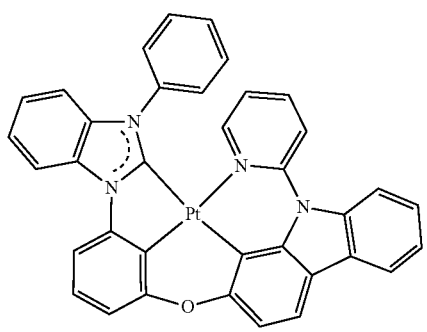
PD31
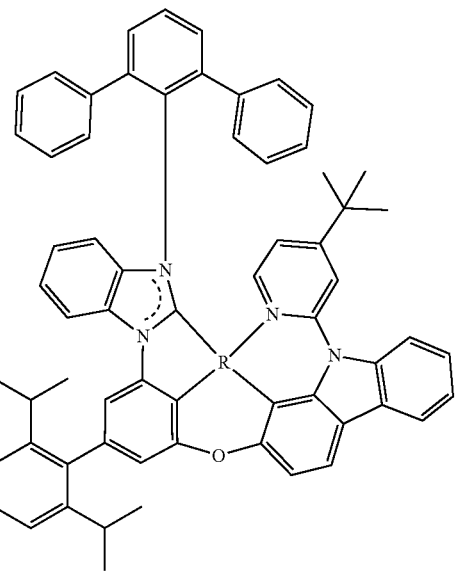
PD32
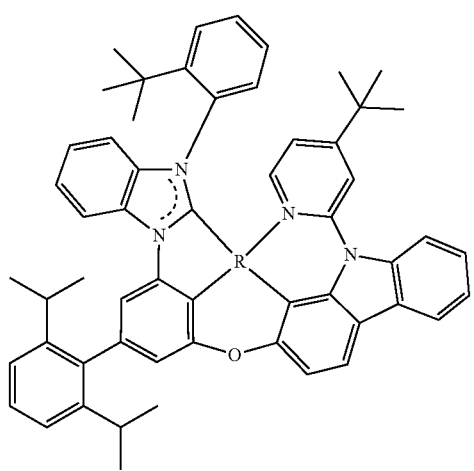
PD33
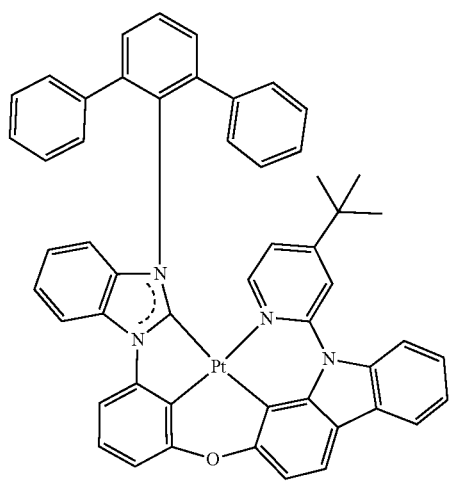

PD34
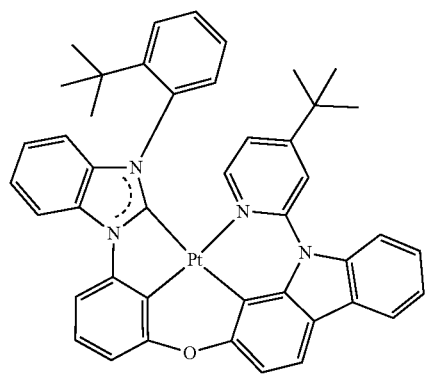
PD35
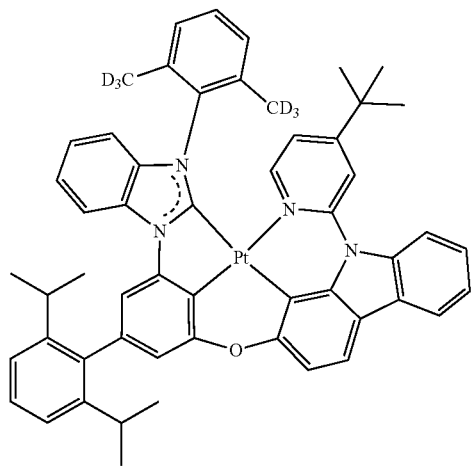
PD36
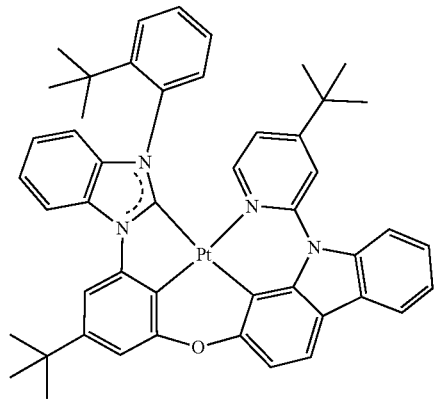
PD37
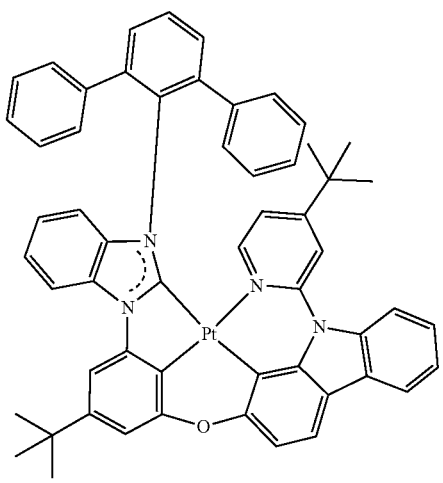
PD38
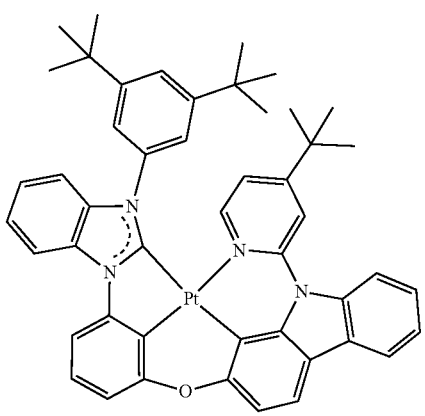
PD39
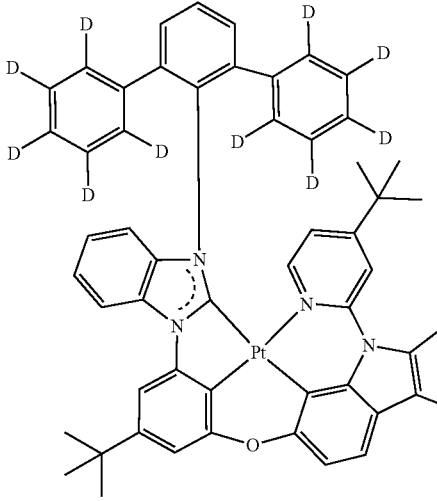
Fluorescent Dopant
The fluorescent dopant may include an amine group-containing compound, a styryl group-containing compound, or any combination thereof.
In an embodiment, the fluorescent dopant may include a compound represented by Formula 501:

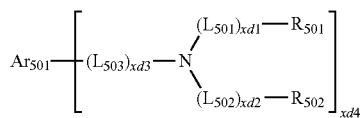

Formula 501 wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, $Ar_{501}$ in Formula 501 may be a condensed cyclic group (for example, an anthracene group, a chrysene group, or a pyrene group) in which three or more monocyclic groups are condensed together (e.g., combined together).

In one or more embodiments, xd4 in Formula 501 may be 2.

In an embodiment, the fluorescent dopant may include: one or more selected from Compounds FD1 to FD36, DPVBi, DPAVBi, or any combination thereof:

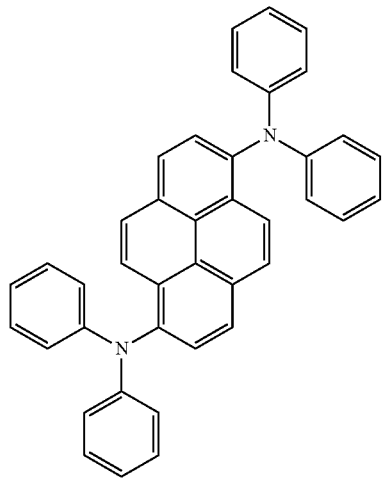

FD1

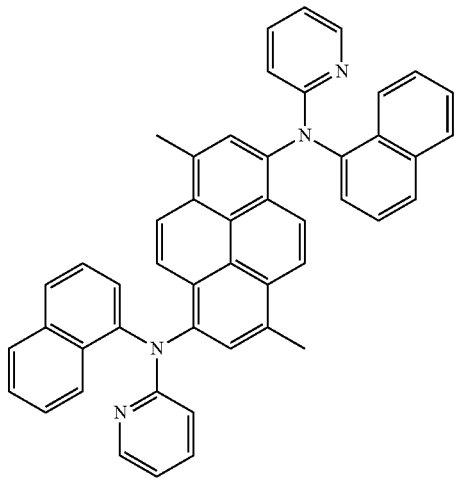

FD2

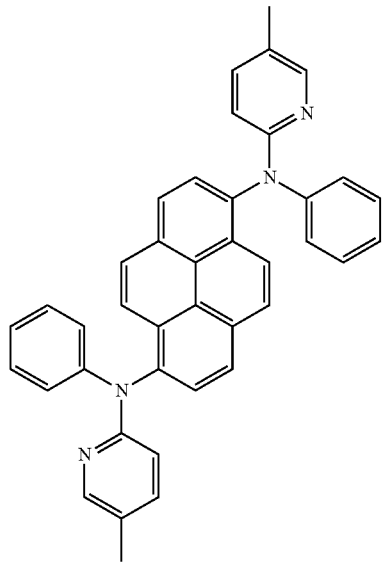

FD3

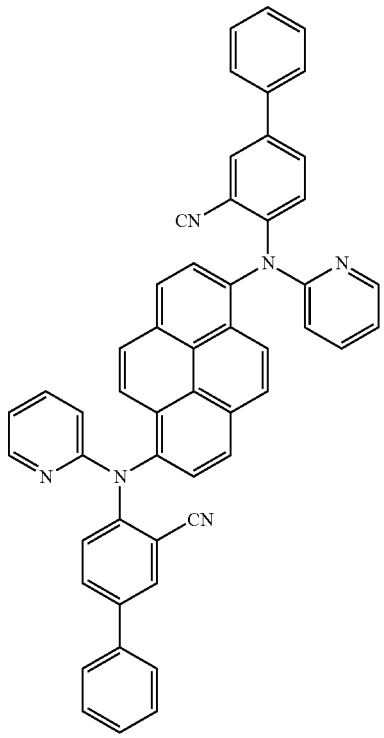

FD4

-continued
FD5
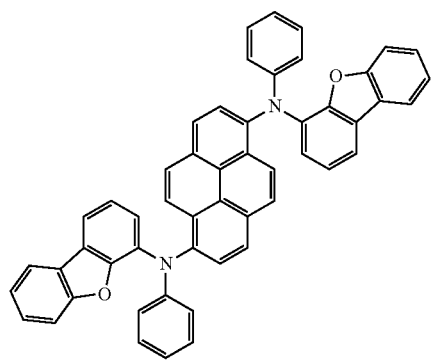
FD6
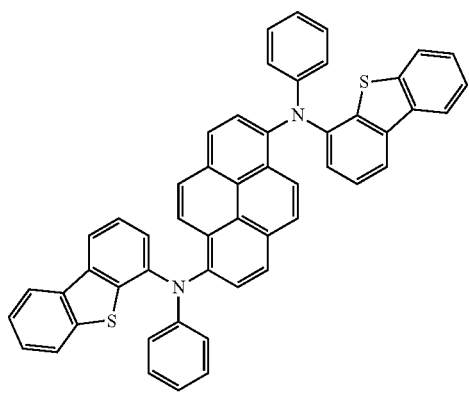
FD7
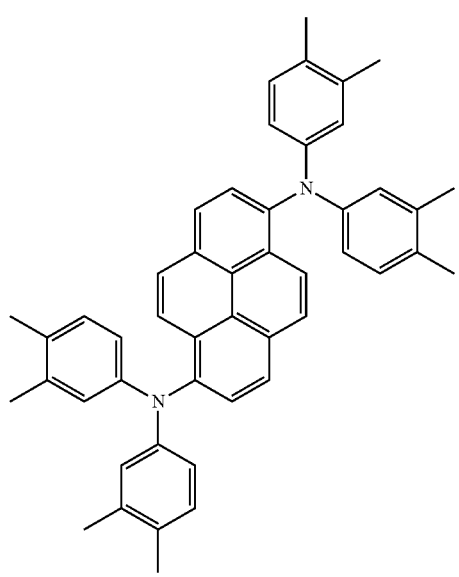
FD8
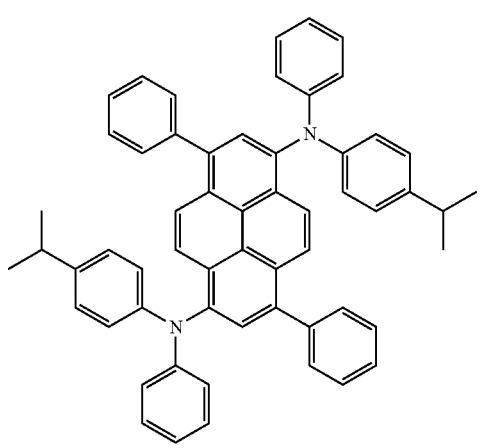
FD9
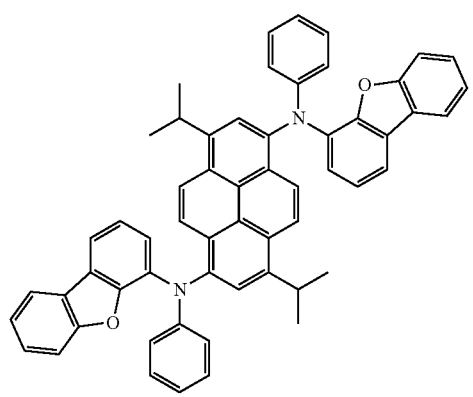
FD10
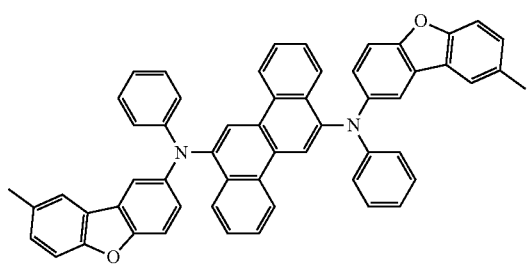

-continued
FD11
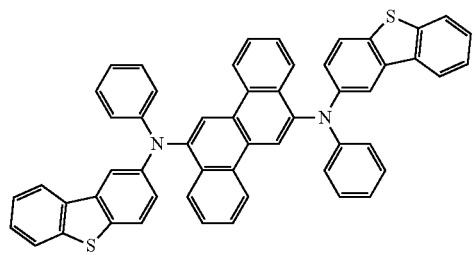
FD12
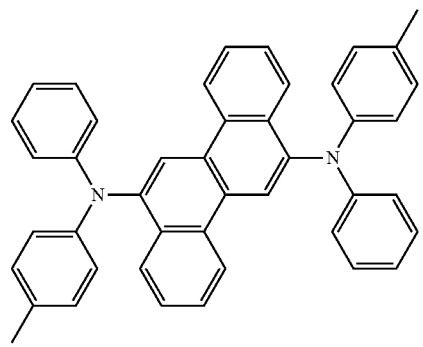
FD13
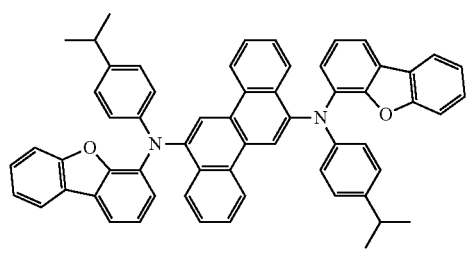
FD14
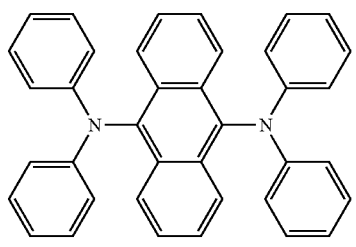
FD15
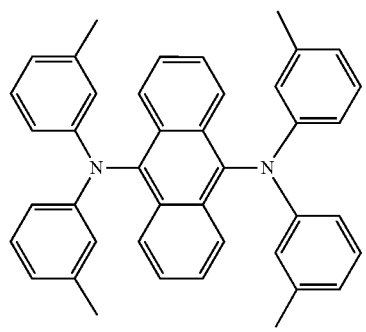
FD16
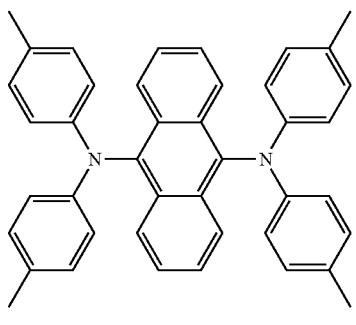
FD17
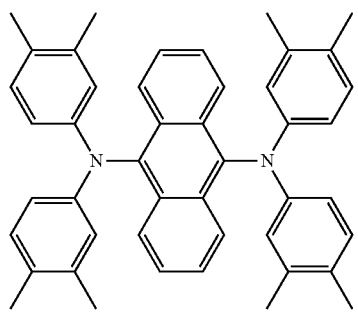
FD18
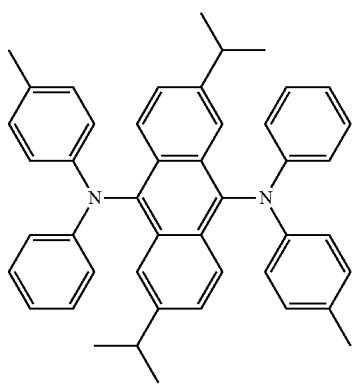

-continued
FD19
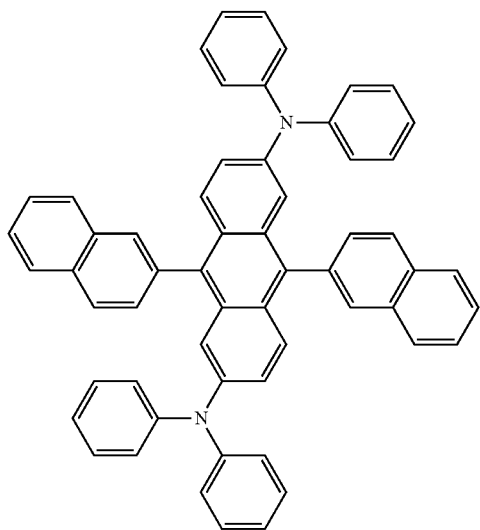
FD20
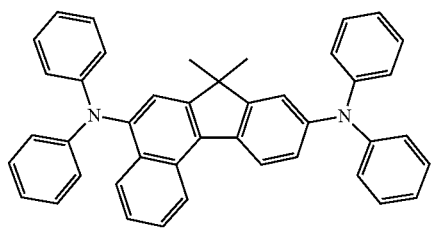
FD21
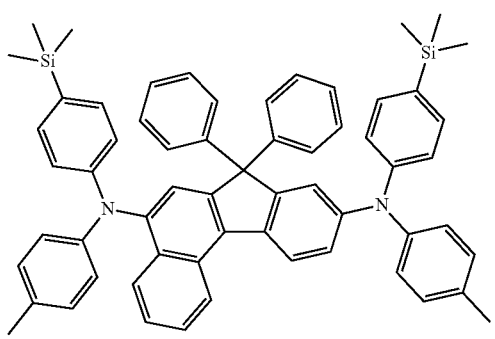
FD22
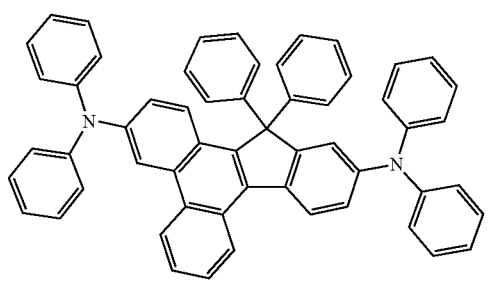
FD23
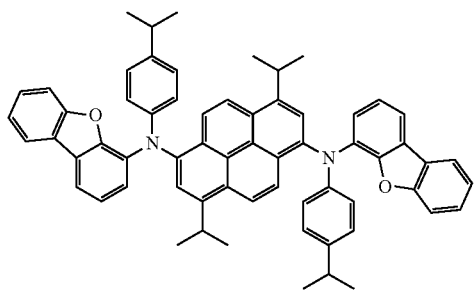
FD24
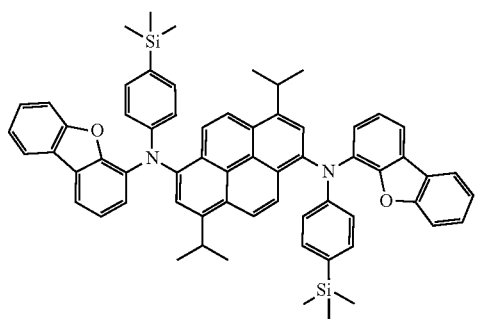
FD25
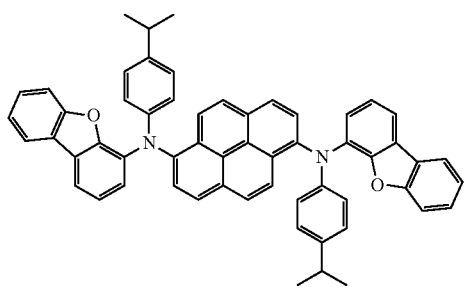
FD26
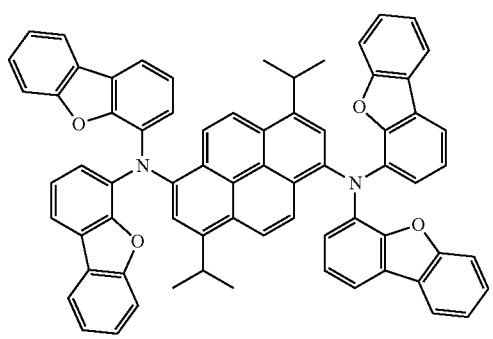

-continued
FD27
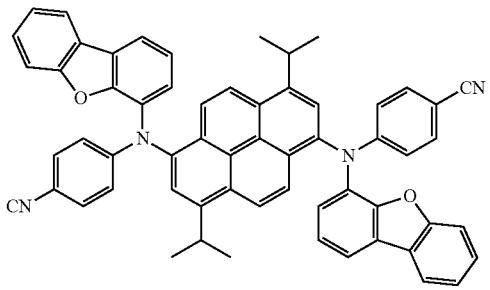
FD28
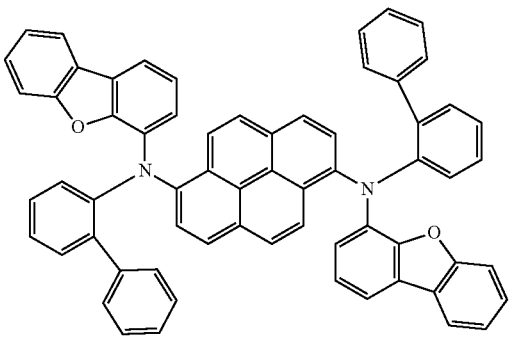
FD29
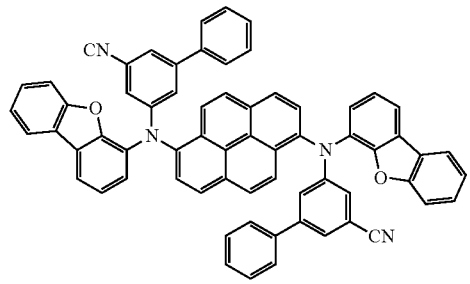
FD30
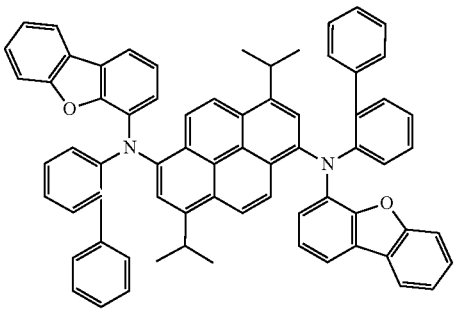
FD31
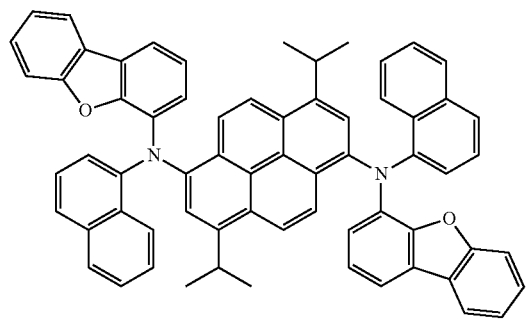
FD32
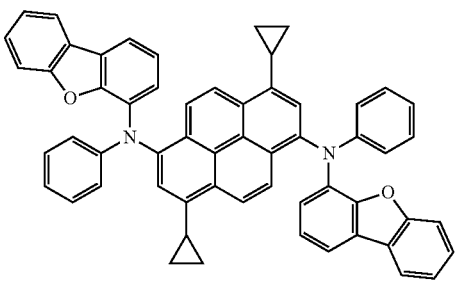
FD33
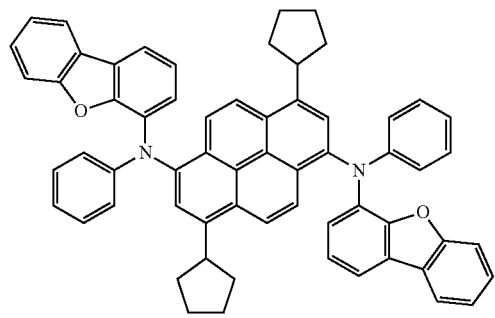
FD34
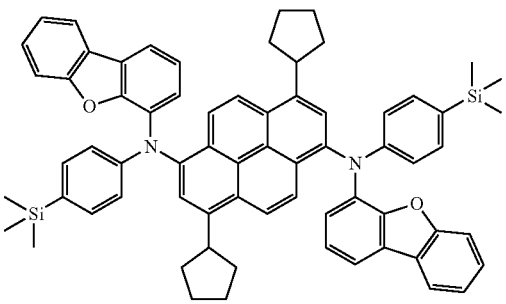
FD35
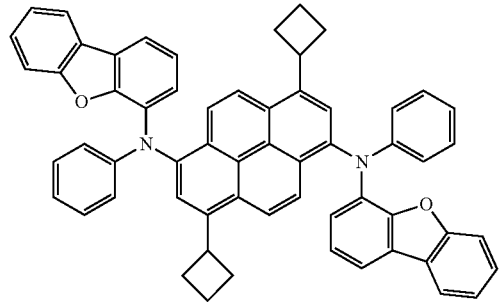
FD36
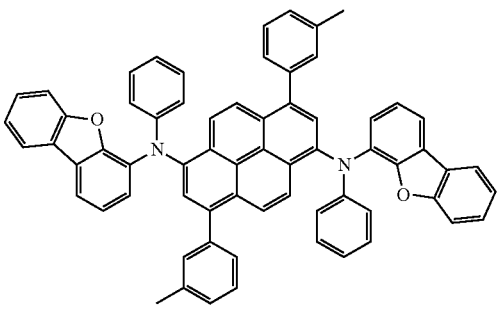

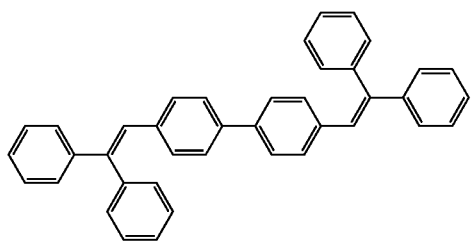

DPVBi

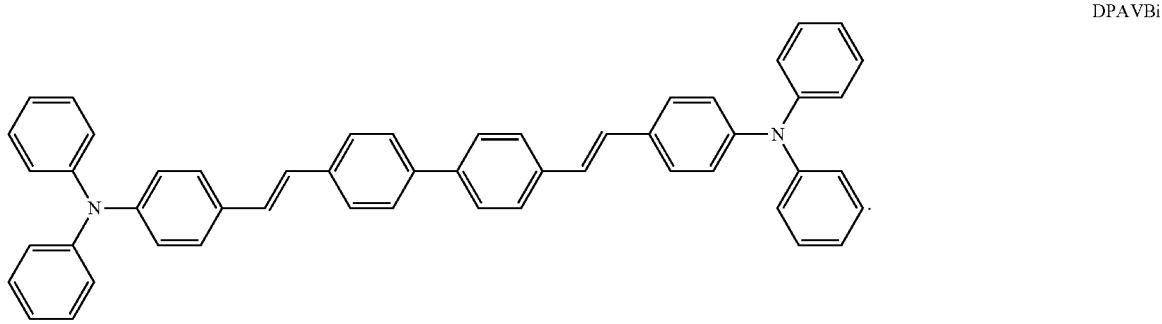

DPAVBi

Delayed Fluorescence Material

The emission layer may include a delayed fluorescence material.

In the present specification, the delayed fluorescence material may be selected from compounds capable of emitting delayed fluorescence based on a delayed fluorescence emission mechanism.

The delayed fluorescence material included in the emission layer may act as a host or a dopant depending on the type (or composition) of other materials included in the emission layer.

In an embodiment, the difference between the triplet energy level (eV) of the delayed fluorescence material and the singlet energy level (eV) of the delayed fluorescence material may be greater than or equal to 0 eV and less than or equal to 0.5 eV. When the difference between the triplet energy level (eV) of the delayed fluorescence material and the singlet energy level (eV) of the delayed fluorescence material satisfies the above-described range, up-conversion from the triplet state to the singlet state of the delayed fluorescence materials may effectively occur, and thus, the luminescence efficiency of the light-emitting device 10 may be improved.

In an embodiment, the delayed fluorescence material may include i) a material including at least one electron donor (for example, a π electron-rich $C_3$-$C_{60}$ cyclic group, such as a carbazole group) and at least one electron acceptor (for example, a sulfoxide group, a cyano group, or a π electron-deficient nitrogen-containing $C_1$-$C_{60}$ cyclic group), and ii) a material including a $C_8$-$C_{60}$ polycyclic group in which two or more cyclic groups are condensed (e.g., combined together) while sharing boron (B) (e.g., having a boron atom that is a ring forming atom of two or more cyclic groups).

Examples of the delayed fluorescence material may include at least one selected from Compounds DF1 to DF9:

DF1

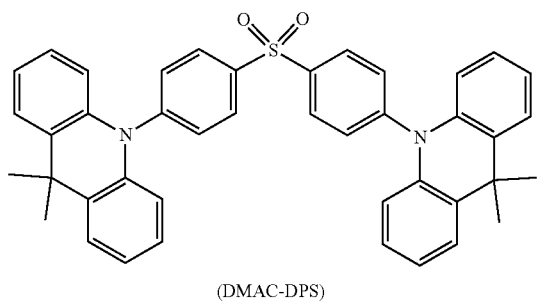

(DMAC-DPS)

DF2

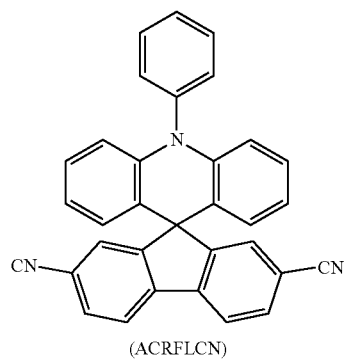

(ACRFLCN)

-continued

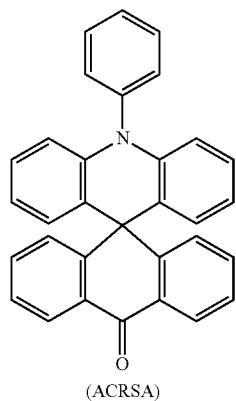

(ACRSA)

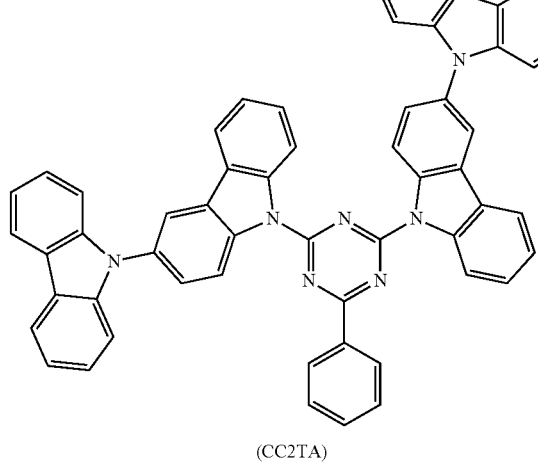

(CC2TA)

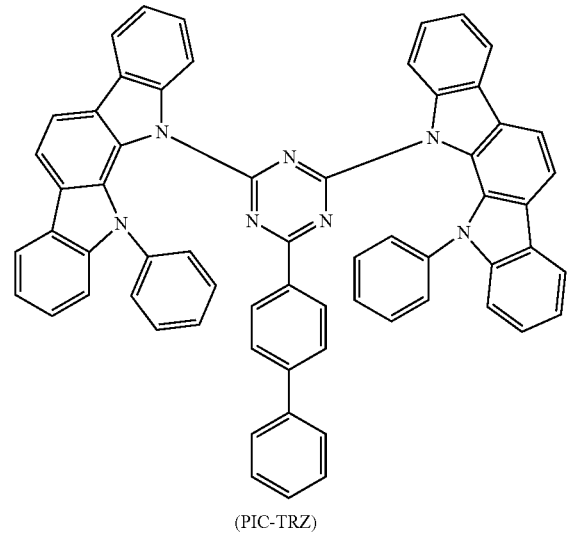

(PIC-TRZ)

-continued

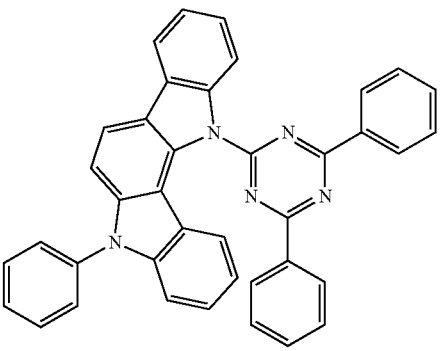

(PIC-TRZ2)

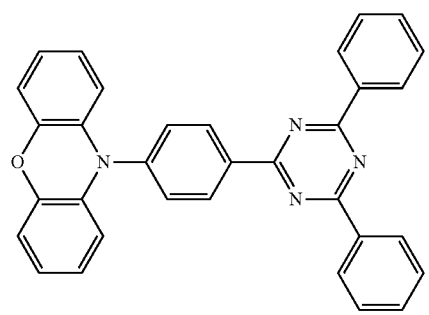

(PXZ-TRZ)

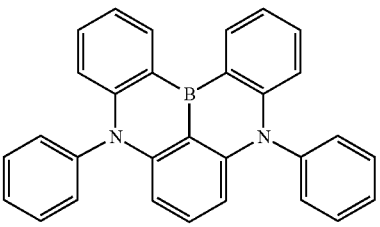

(DABNA-1)

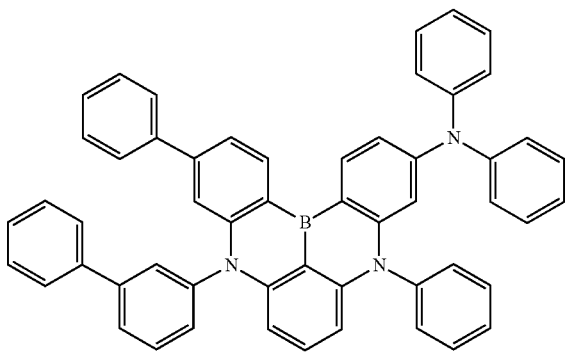

(DABNA-2)

Quantum Dot

The emission layer may include a quantum dot.

In the present specification, a quantum dot refers to a crystal of a semiconductor compound, and may include any suitable material capable of emitting light of various suitable emission wavelengths according to the size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or any suitable process similar thereto.

According to the wet chemical process, a precursor material is mixed with an organic solvent to grow a quantum dot particle crystal. When the crystal grows, the organic solvent naturally acts as a dispersant coordinated on the surface of the quantum dot crystal and controls the growth of the crystal so that the growth of quantum dot particles can be controlled through a process which is more easily performed than vapor deposition methods, such as metal organic chemical vapor deposition (MOCVD) or molecular beam epitaxy (MBE), and which requires low costs.

The quantum dot may include Group II-VI semiconductor compounds, Group III-V semiconductor compounds, Group III-VI semiconductor compounds, Group I-III-VI semiconductor compounds, Group IV-VI semiconductor compounds, Group IV element or compound; or any combination thereof.

Examples of the Group II-VI semiconductor compound include a binary compound, such as CdSe, CdTe, ZnS, ZnSe, ZnTe, ZnO, HgS, HgSe, HgTe, MgSe, and/or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound, such as CdZnSeS, CdZnSeTe, CdZnSTe, CdHgSeS, CdHgSeTe, CdHgSTe, HgZnSeS, HgZnSeTe, and/or HgZnSTe; or any combination thereof.

Examples of the Group III-V semiconductor compound are a binary compound, such as GaN, GaP, GaAs, GaSb, AlN, AlP, AlAs, AlSb, InN, InP, InAs, InSb, and/or the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and/or the like; a quaternary compound, such as GaAlNAs, GaAlNSb, GaAlPAs, GaAlPSb, GaInNP, GaInNAs, GaInNSb, GaInPAs, GaInPSb, GaAlNP, InAlNP, InAlNAs, InAlNSb, InAlPAs, InAlPSb, and/or the like; or any combination thereof. In one or more embodiments, the Group III-V semiconductor compound may further include Group II elements. Examples of the Group III-V semiconductor compound further including Group II elements include InZnP, InGaZnP, InAlZnP, etc.

Examples of the Group III-VI semiconductor compound include a binary compound, such as GaS, GaSe, $Ga_2Se_3$, GaTe, InS, InSe, $In_2S_3$, $In_2Se_3$, and/or InTe; a ternary compound, such as $InGaS_3$, and/or $InGaSe_3$; and any combination thereof.

Examples of the Group I-III-VI semiconductor compound include a ternary compound, such as AgInS, $AgInS_2$, CuInS, $CuInS_2$, $CuGaO_2$, $AgGaO_2$, and/or $AgAlO_2$; or any combination thereof.

Examples of the Group IV-VI semiconductor compound include a binary compound, such as SnS, SnSe, SnTe, PbS, PbSe, PbTe, and/or the like; a ternary compound, such as SnSeS, SnSeTe, SnSTe, PbSeS, PbSeTe, PbSTe, SnPbS, SnPbSe, SnPbTe, and/or the like; a quaternary compound, such as SnPbSSe, SnPbSeTe, SnPbSTe, and/or the like; or any combination thereof.

The Group IV element or compound may include a single element compound, such as Si or Ge; a binary compound, such as SiC and/or SiGe; or any combination thereof.

Each element included in a multi-element compound such as the binary compound, ternary compound and quaternary compound, may exist in a particle having a uniform concentration or non-uniform concentration.

In one or more embodiments, the quantum dot may have a single structure or a dual core-shell structure. In the case of the quantum dot having a single structure, the concentration of each element included in the corresponding quantum dot is uniform (e.g., substantially uniform). In one or more embodiments, the material contained in the core and the material contained in the shell may be different from each other.

The shell of the quantum dot may act as a protective layer to prevent or reduce chemical degeneration of the core to maintain semiconductor characteristics and/or as a charging layer to impart electrophoretic characteristics to the quantum dot. The shell may be a single layer or a multi-layer. The interface between the core and the shell may have a concentration gradient that decreases along a direction toward the center of the element present in the shell.

Examples of the shell of the quantum dot may include an oxide of metal, metalloid, and/or non-metal, a semiconductor compound, and any combination thereof. Examples of the oxide of metal, metalloid, and/or non-metal include a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound, such as $MgAl_2O_4$, $CoFe_2O_4$, $NiFe_2O_4$, and/or $CoMn_2O_4$; and any combination thereof. Examples of the semiconductor compound include, as described herein, Group II-VI semiconductor compounds; Group III-V semiconductor compounds; Group III-VI semiconductor compounds; Group I-III-VI semiconductor compounds; Group IV-VI semiconductor compounds; and any combination thereof. In addition, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be about 45 nm or less, for example, about 40 nm or less, for example, about 30 nm or less, and within these ranges, color purity and/or color gamut may be increased. In addition, because the light emitted from the quantum dot is emitted in all directions (or substantially all directions), the quantum dot may provide an improved wide viewing angle.

In addition, the quantum dot may include a spherical particle, a pyramidal particle, a multi-arm particle, a cubic nanoparticle, a nanotube particle, a nanowire particle, a nanofiber particle, and/or a nanoplate particle.

Because the energy band gap may be adjusted by controlling the size of the quantum dot, light having various suitable wavelength bands may be obtained from the quantum dot emission layer. Therefore, by using quantum dots of different sizes, a light-emitting device that emits light of various suitable wavelengths may be implemented. In one or more embodiments, the size of the quantum dot may be selected to emit red, green and/or blue light. In addition, the size of the quantum dot may be configured to emit white light by combining light of various suitable colors.

Electron Transport Region in Interlayer 130

The electron transport region may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The electron transport region may include a buffer layer, a hole blocking layer, an electron control layer, an electron transport layer, an electron injection layer, or any combination thereof.

In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers are sequentially stacked from an emission layer.

In an embodiment, the electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601:

$$[Ar_{601}]_{xe11}-[(L_{601})_{xe1}-R_{601}]_{xe21} \quad \text{Formula 601}$$

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($O_{601}$)($O_{602}$)($O_{603}$), —C(=O)($Q_{601}$), —S(=O)$_2$($Q_{601}$), or —P(=O)($Q_{601}$)($Q_{602}$), $Q_{601}$ to $Q_{603}$ are each the same as described in connection with $Q_1$, xe21 may be 1, 2, 3, 4, or 5, and at least one selected from $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}$(s) may be linked to each other via a single bond.

In one or more embodiments, $Ar_{601}$ in Formula 601 may be a substituted or unsubstituted anthracene group.

In one or more embodiments, the electron transport region may include a compound represented by Formula 601-1:

Formula 601-1

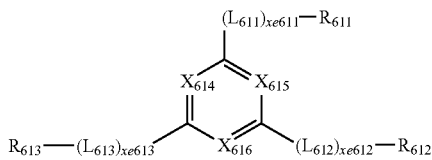

wherein, in Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ are each the same as described in connection with $L_{601}$, xe611 to xe613 are each the same as described in connection with xe1, $R_{611}$ to $R_{613}$ are each the same as described in connection with $R_{601}$, and $R_{614}$ to $R_{616}$ may each independently be hydrogen, -D, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, xe1 and xe611 to xe613 in Formulae 601 and 601-1 may each independently be 0, 1, or 2.

The electron transport region may include one or more selected from Compounds ET1 to ET45, 2,9-dimethyl-4,7-diphenyl-1,10-phenanthroline (BCP), 4,7-diphenyl-1,10-phenanthroline (Bphen), Alq$_3$, BAlq, TAZ, NTAZ, or any combination thereof:

ET1

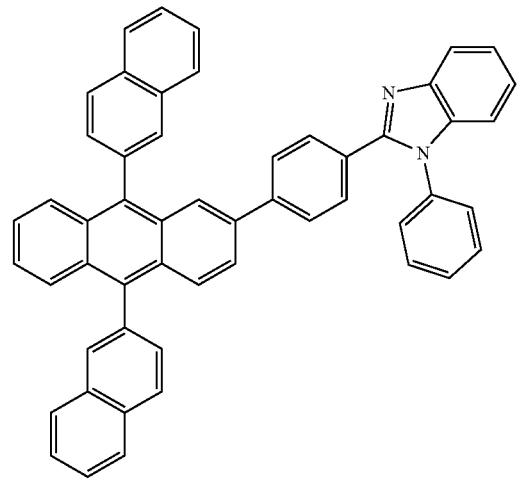

ET2

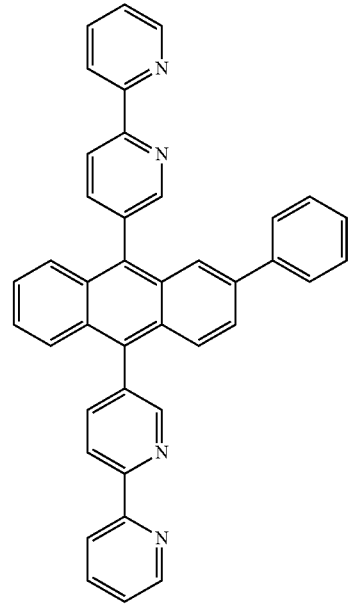

ET3
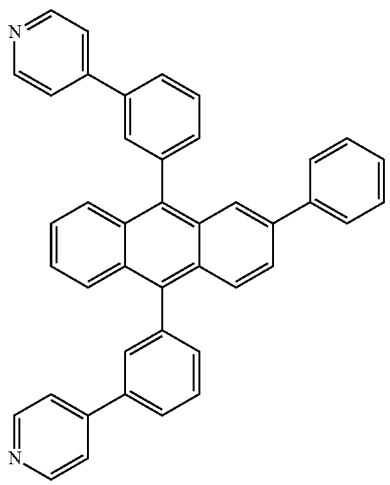
ET4
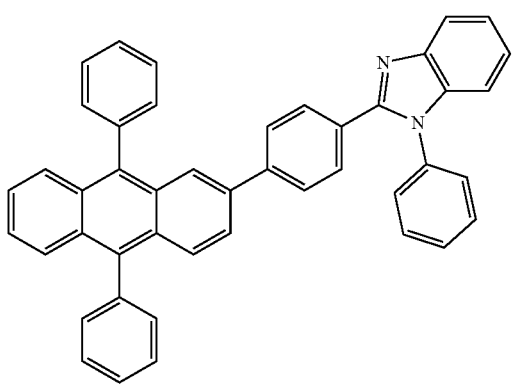
ET5
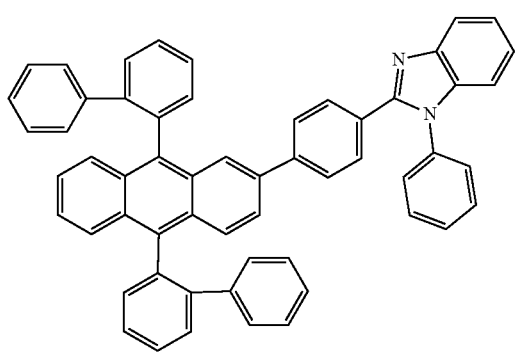
ET6
ET7
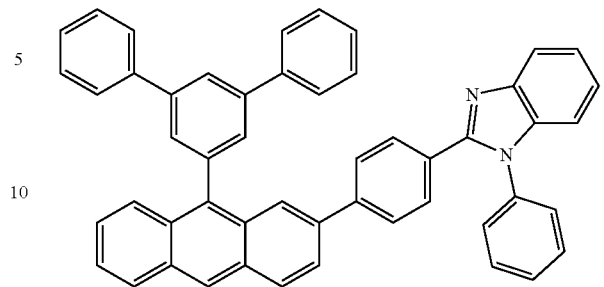
ET8
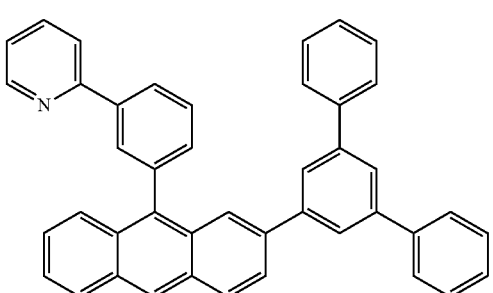
ET9
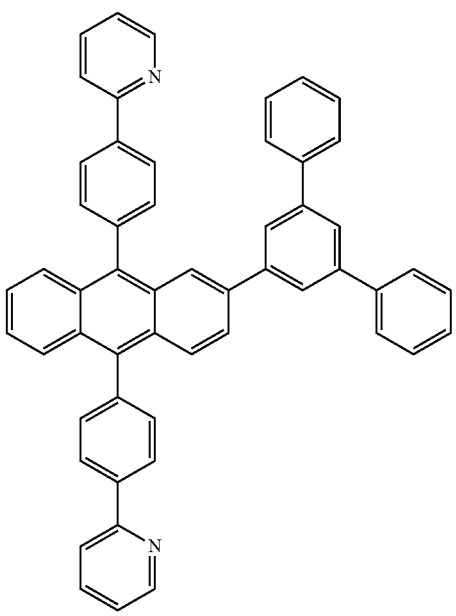

ET10
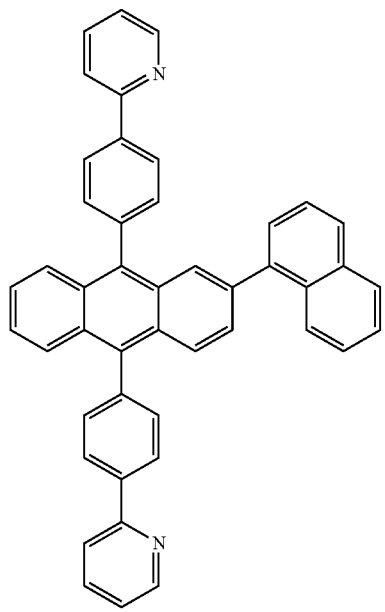
ET11
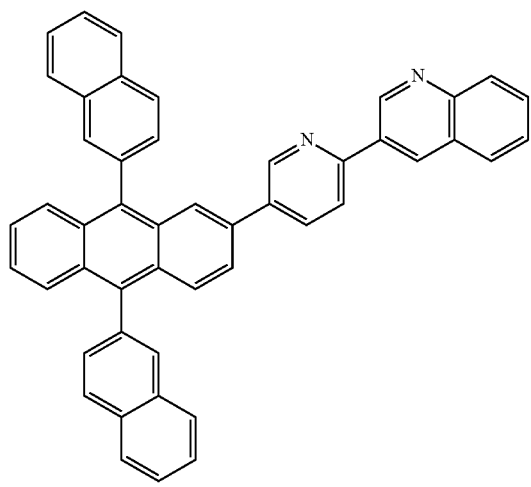
ET12
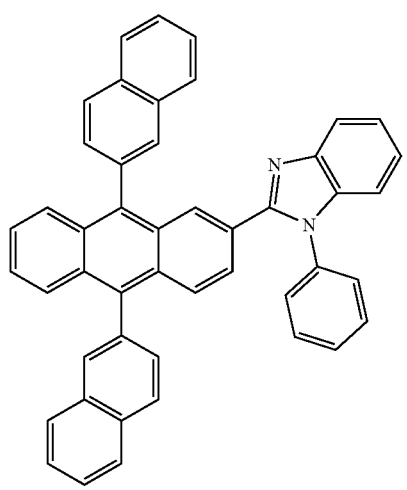
ET13
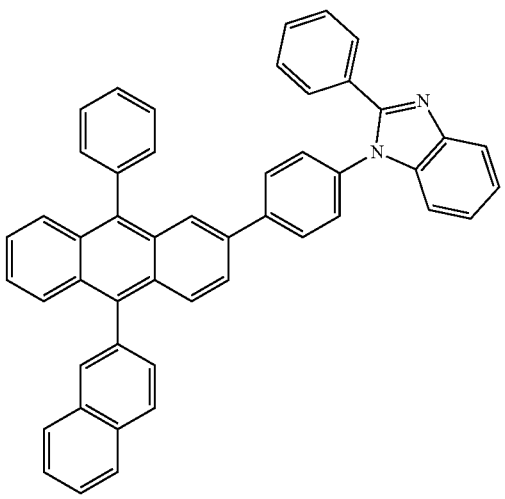
ET14
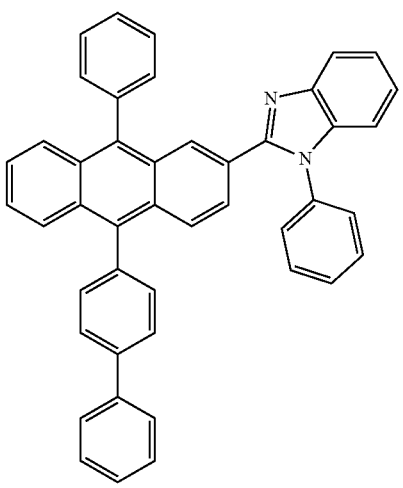
ET15
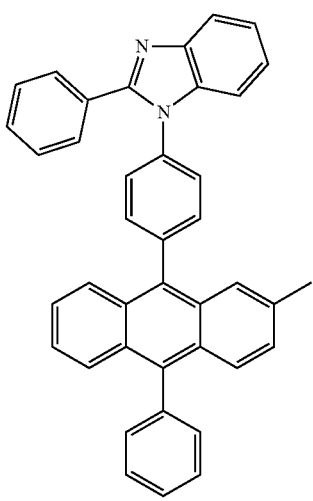

ET16
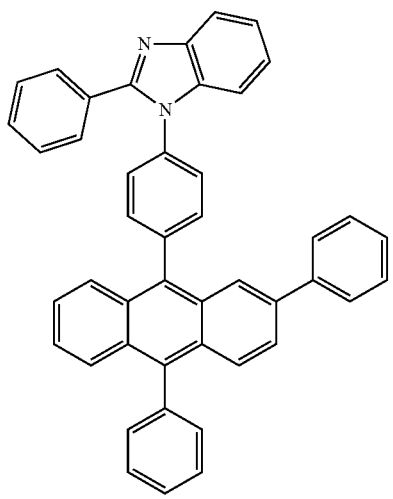
ET17
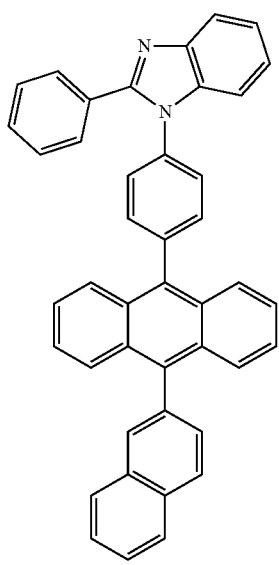
ET18
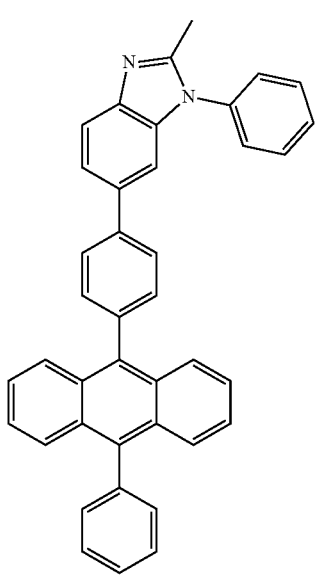
ET19
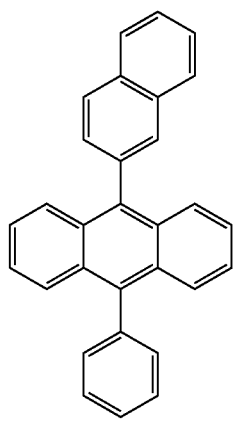
ET20
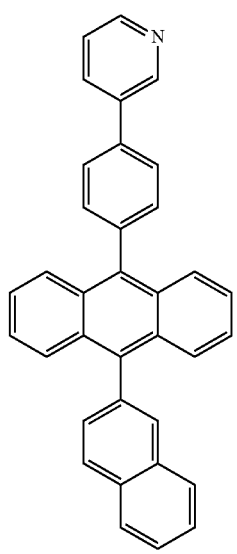
ET21
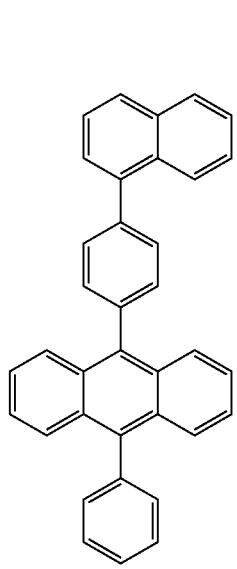

ET22
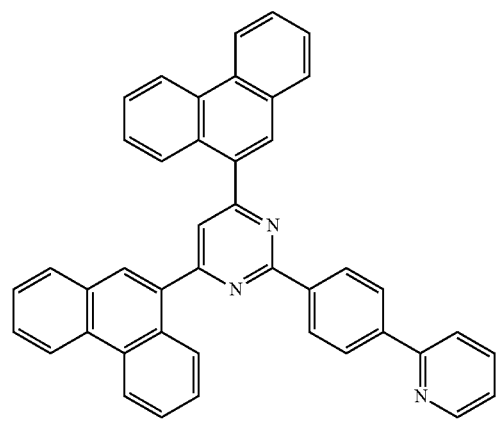
ET23
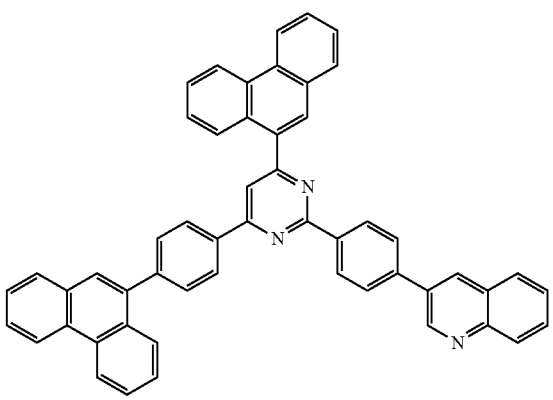
ET24
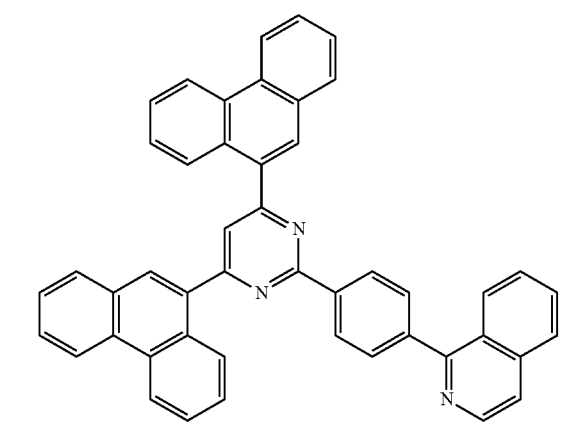
ET25
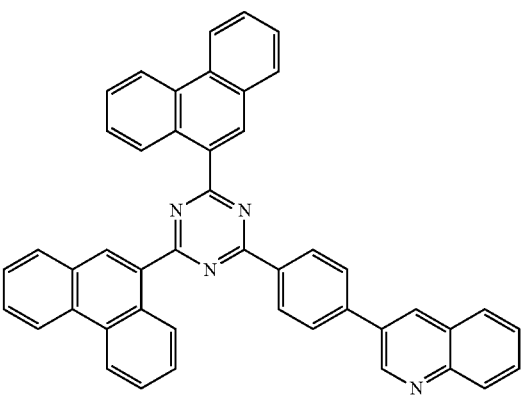
ET26
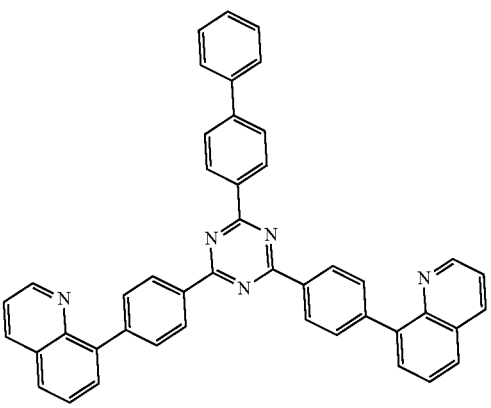
ET27
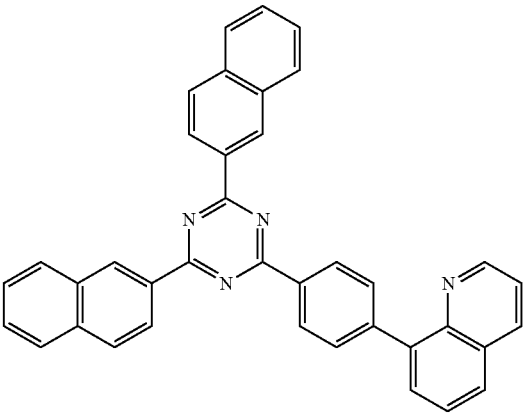
ET28
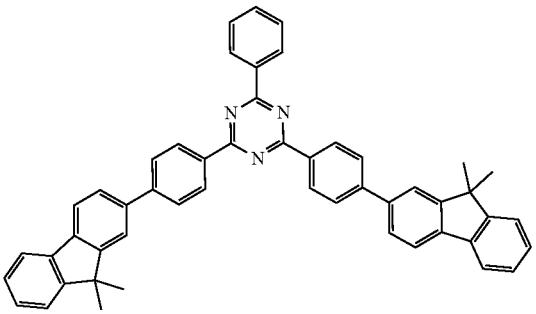

ET29
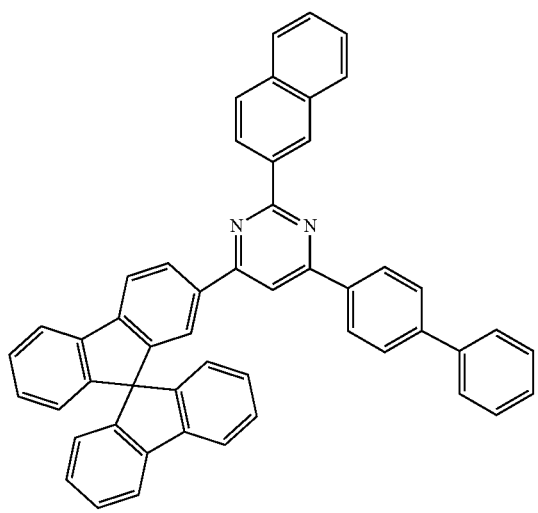
ET30
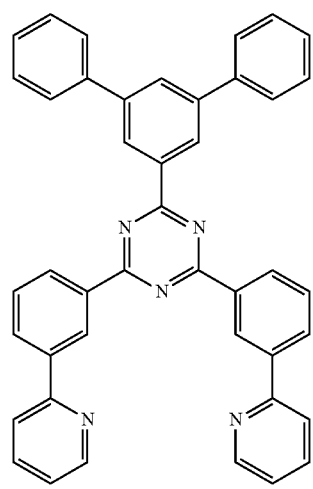
ET31
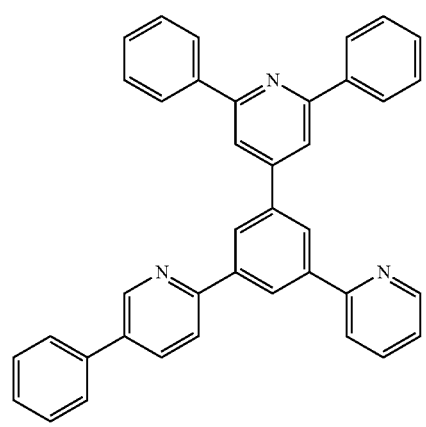
ET32
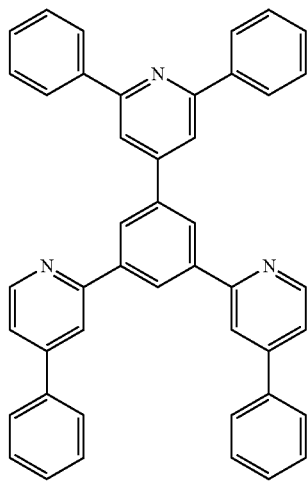
ET33
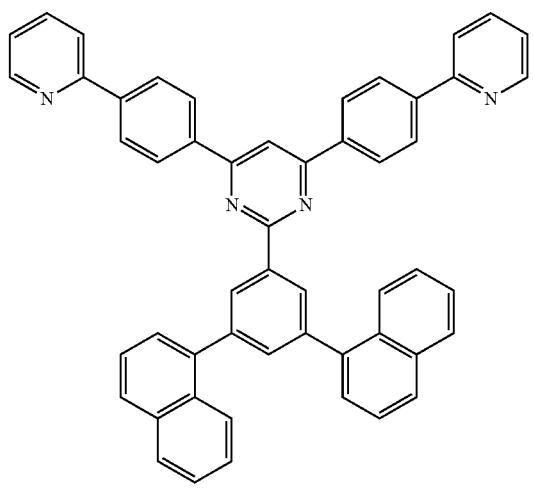
ET34
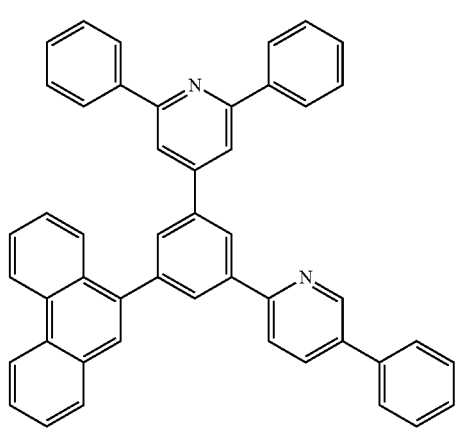

ET35
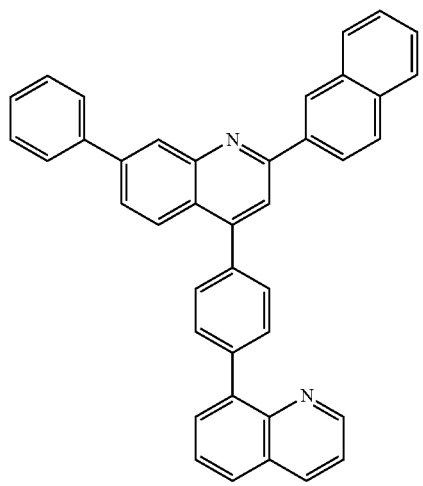
ET36
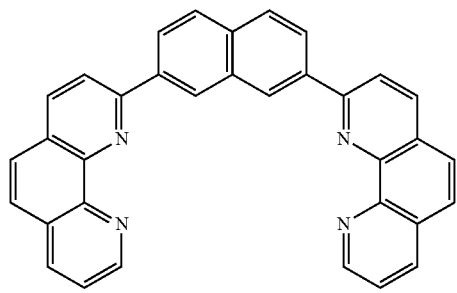
ET37
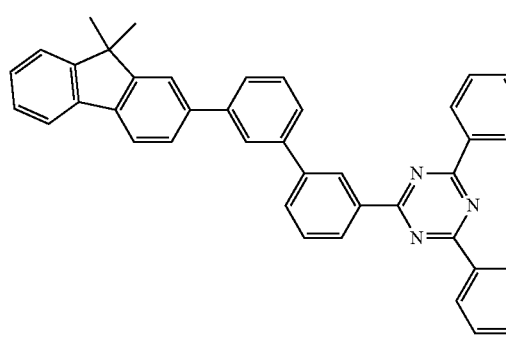
ET38
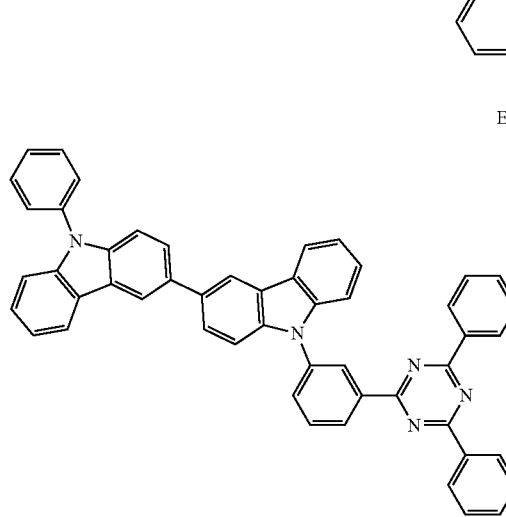
ET39
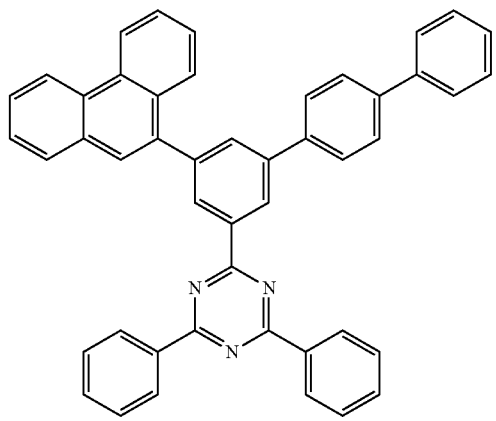
ET40
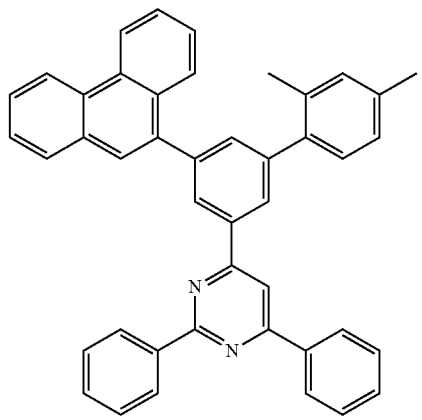
ET41
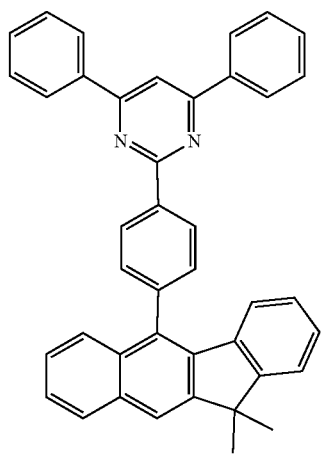

ET42

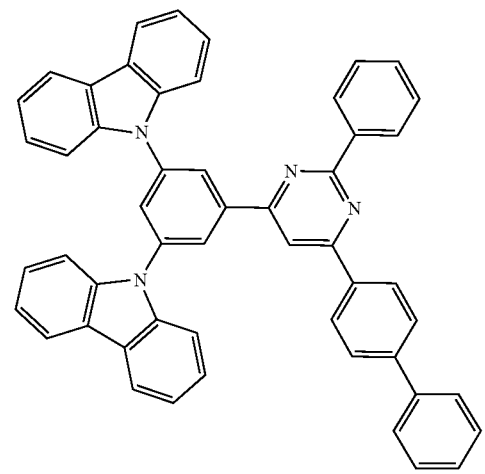

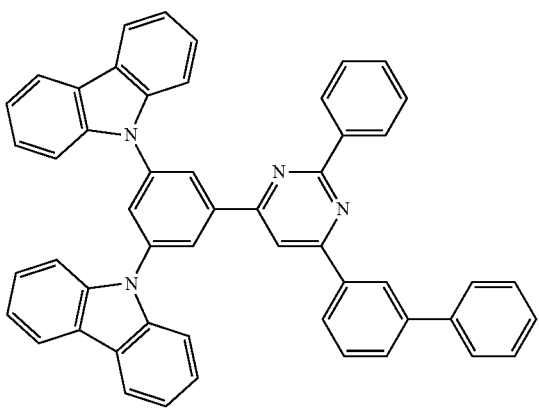

ET44

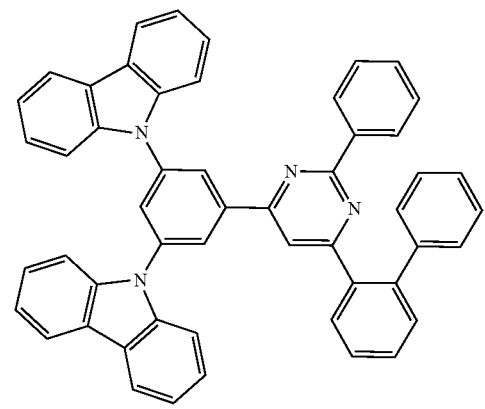

ET45

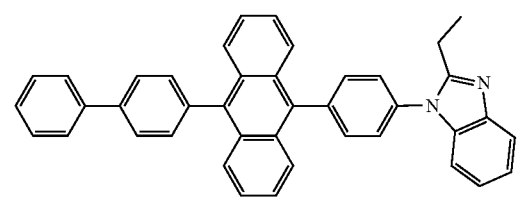

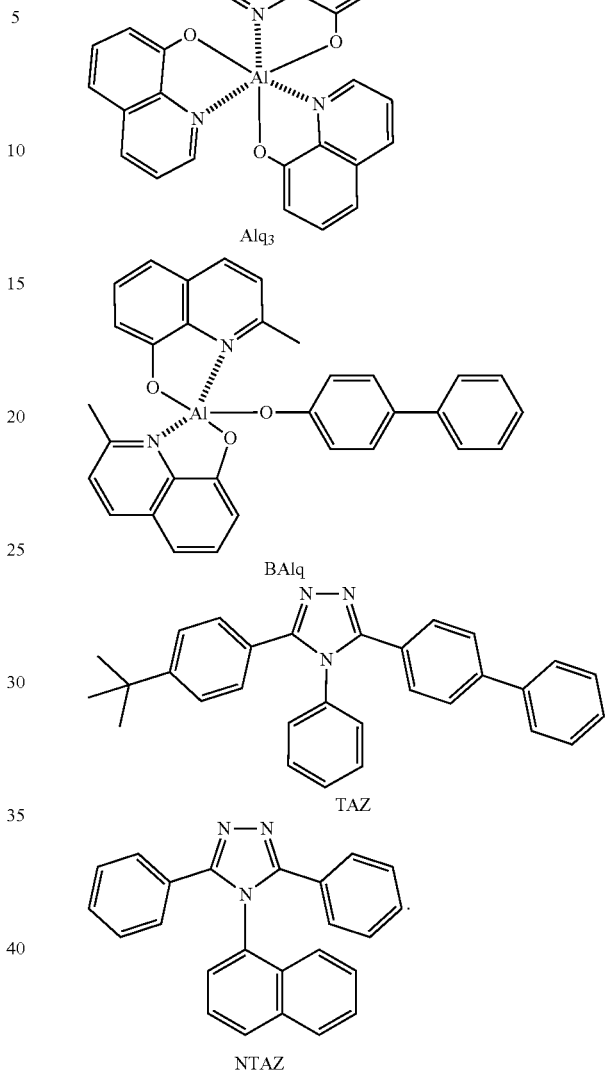

The thickness of the electron transport region may be from about 100 Å to about 5,000 Å, for example, from about 160 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be from about 20 Å to about 1,000 Å, for example, about 30 Å to about 300 Å, and a thickness of the electron transport layer may be from about 100 Å to about 1,000 Å, for example, about 150 Å to about 500 Å. When the thicknesses of the buffer layer, the hole blocking layer, the electron control layer, the electron transport layer and/or the electron transport layer are within the ranges described above, suitable or satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a Li ion, a Na ion, a K ion, a Rb ion, or a Cs ion, and a metal ion of the alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

In an embodiment, the metal-containing material may include a Li complex. The Li complex may include, for example, Compound ET-D1 (LiQ) or ET-D2:

ET-D1

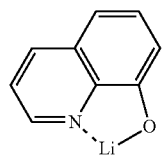

ET-D2

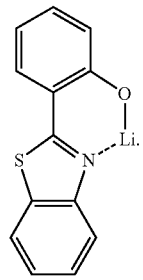

The electron transport region may include an electron injection layer that facilitates the injection of electrons from the cathode 150. The electron injection layer may directly contact (e.g., physically contact) the cathode 150.

The electron injection layer may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may be oxides, halides (for example, fluorides, chlorides, bromides, and/or iodides), and/or tellurides of the alkali metal, the alkaline earth metal, and the rare earth metal, or any combination thereof.

The alkali metal-containing compound may include alkali metal oxides, such as $Li_2O$, $Cs_2O$, and/or $K_2O$, alkali metal halides, such as LiF, NaF, CsF, KF, LiI, NaI, CsI, and/or KI, or any combination thereof. The alkaline earth metal-containing compound may include an alkaline earth metal compound, such as BaO, SrO, CaO, $Ba_xSr_{1-x}O$ (x is a real number satisfying the condition of 0<x<1), $Ba_xCa_{1-x}O$ (x is a real number satisfying the condition of 0<x<1), and/or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In one or more embodiments, the rare earth metal-containing compound may include lanthanide metal telluride. Examples of the lanthanide metal telluride include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), as a ligand bonded to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may include (e.g., consist of) an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In an embodiment, the electron injection layer may include (e.g., consist of) i) an alkali metal-containing compound (for example, an alkali metal halide), ii) a) an alkali metal-containing compound (for example, an alkali metal halide); and b) an alkali metal, an alkaline earth metal, a rare earth metal, or any combination thereof. In an embodiment, the electron injection layer may include a KI:Yb co-deposited layer, an RbI:Yb co-deposited layer, and/or the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material.

A thickness of the electron injection layer may be in a range of about 1 Å to about 100 Å, and, for example, about 3 Å to about 90 Å. When the thickness of the electron injection layer is within the range described above, the electron injection layer may have suitable or satisfactory electron injection characteristics without a substantial increase in driving voltage.

Cathode 150

The cathode 150 may be on the interlayer 130 having such a structure. The cathode 150 may be an electron injection electrode, and as the material for the cathode 150, a metal, an alloy, an electrically conductive compound, or any combination thereof, each having a low work function, may be used.

The cathode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The cathode 150 may be a transmissive electrode, a semi-transmissive electrode, or a reflective electrode.

The cathode 150 may have a single-layered structure or a multi-layered structure including two or more layers.

Capping Layer

A first capping layer may be outside the anode 110, and/or a second capping layer may be outside the cathode 150. In more detail, the light-emitting device 10 may have a structure in which the first capping layer, the anode 110, the interlayer 130, and the cathode 150 are sequentially stacked in this stated order, a structure in which the anode 110, the interlayer 130, the cathode 150, and the second capping layer are sequentially stacked in this stated order, or a structure in which the first capping layer, the anode 110, the interlayer 130, the cathode 150, and the second capping layer are sequentially stacked in this stated order.

Light generated in an emission layer of the interlayer 130 of the light-emitting device 10 may be extracted toward the outside through the anode 110, which is a semi-transmissive electrode or a transmissive electrode, and the first capping layer or light generated in an emission layer of the interlayer 130 of the light-emitting device 10 may be extracted toward the outside through the cathode 150, which is a semi-transmissive electrode or a transmissive electrode, and the second capping layer.

The first capping layer and the second capping layer may increase external emission efficiency according to the principle of constructive interference. Accordingly, the light extraction efficiency of the light-emitting device 10 is increased, so that the luminescence efficiency of the light-emitting device 10 may be improved.

Each of the first capping layer and second capping layer may include a material having a refractive index (at a wavelength of 589 nm) of 1.6 or more.

The first capping layer and the second capping layer may each independently include an organic capping layer including an organic material, an inorganic capping layer including an inorganic material, or an organic-inorganic composite capping layer including an organic material and an inorganic material.

At least one selected from the first capping layer and the second capping layer may each independently include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may be optionally substituted with a substituent containing O, N, S, Se, Si, F, Cl, Br, I, or any combination thereof. In one or more embodiments, at least one selected from the first capping layer and the second capping layer may each independently include an amine group-containing compound.

In one or more embodiments, at least one selected from the first capping layer and the second capping layer may each independently include a compound represented by Formula 201, a compound represented by Formula 202, or any combination thereof.

In one or more embodiments, at least one selected from the first capping layer and the second capping layer may each independently include one or more selected from Compounds HT28 to HT33, one or more selected from Compounds CP1 to CP6, β-NPB, or any combination thereof:

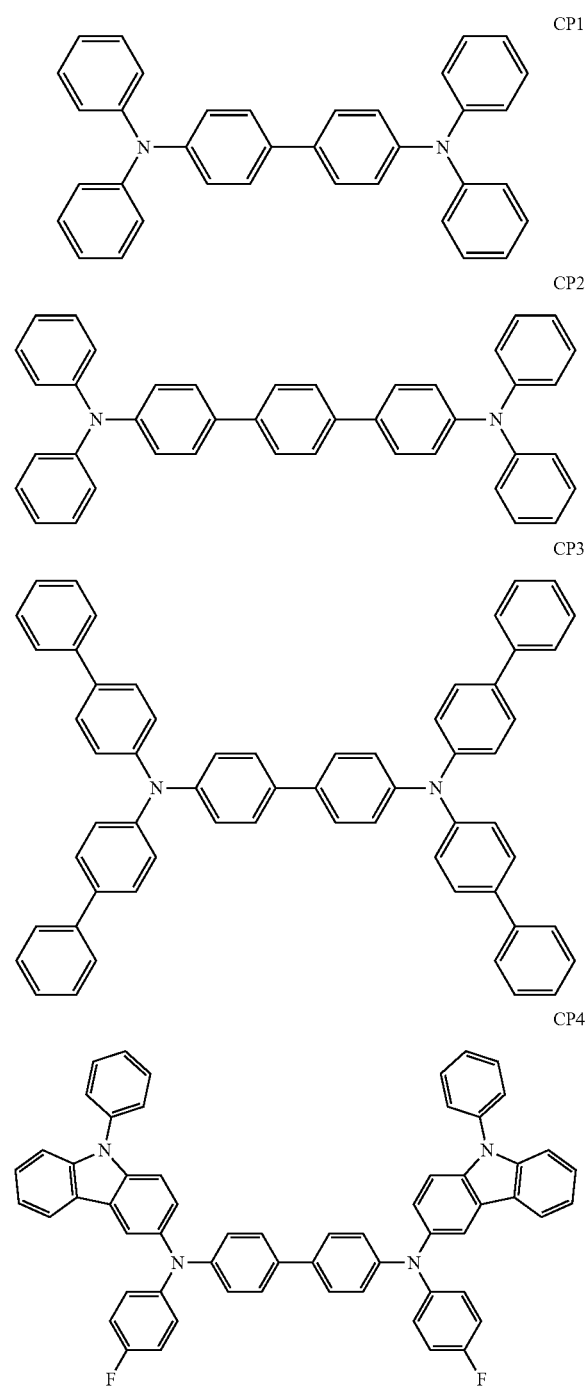

-continued

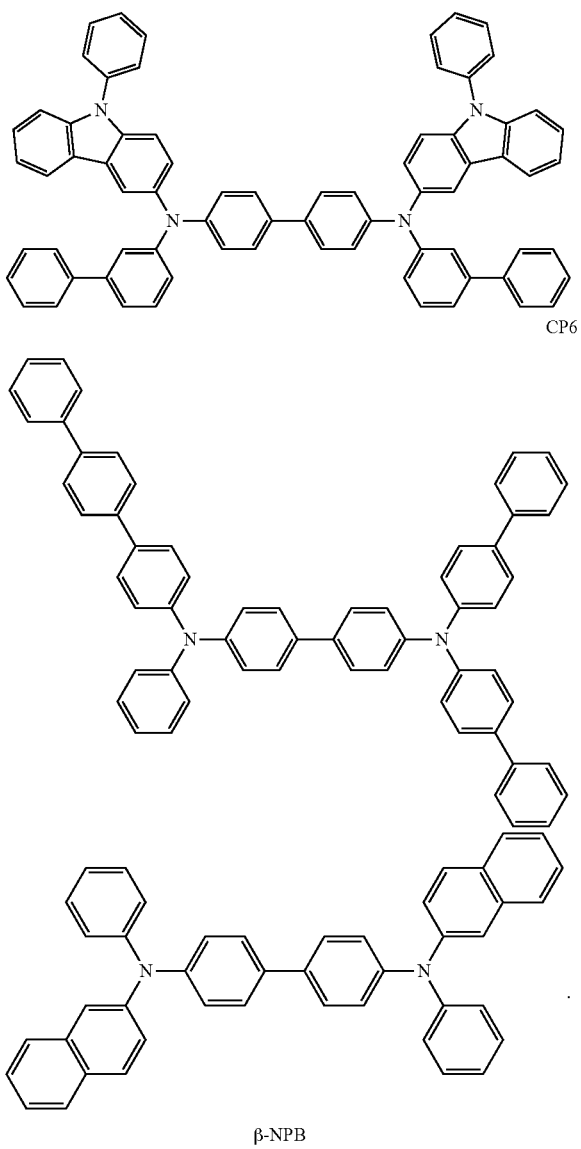

β-NPB

Electronic Apparatus

The light-emitting device may be included in various suitable electronic apparatuses. In an embodiment, the electronic apparatus including the light-emitting device may be a light-emitting apparatus, an authentication apparatus, and/or the like.

The electronic apparatus (for example, light-emitting apparatus) may further include, in addition to the light-emitting device, i) a color filter, ii) a color conversion layer, or iii) a color filter and a color conversion layer. The color filter and/or the color conversion layer may be in at least one traveling direction of light emitted from the light-emitting device. In an embodiment, the light emitted from the light-emitting device may be blue light or white light. The light-emitting device may be the same as described above. In an embodiment, the color conversion layer may include quantum dots. The quantum dot may be, for example, a quantum dot as described herein.

The electronic apparatus may include a first substrate. The first substrate may include a plurality of subpixel areas, the color filter may include a plurality of color filter areas respectively corresponding to the subpixel areas, and the color conversion layer may include a plurality of color conversion areas respectively corresponding to the subpixel areas.

A pixel-defining film may be located among the subpixel areas to define each of the subpixel areas.

The color filter may further include a plurality of color filter areas and light-shielding patterns located among the color filter areas, and the color conversion layer may include a plurality of color conversion areas and light-shielding patterns located among the color conversion areas.

The color filter areas (or the color conversion areas) may include a first area emitting first-color light, a second area emitting second-color light, and/or a third area emitting third-color light, and the first-color light, the second-color light, and/or the third-color light may have different maximum emission wavelengths from one another. In an embodiment, the first-color light may be red light, the second-color light may be green light, and the third-color light may be blue light. In an embodiment, the color filter areas (or the color conversion areas) may include quantum dots. In more detail, the first area may include a red quantum dot, the second area may include a green quantum dot, and the third area may not include a quantum dot. The quantum dot is the same as described in the present specification. The first area, the second area, and/or the third area may each include a scatterer (e.g., a light scatterer).

In an embodiment, the light-emitting device may emit a first light, the first area may absorb the first light to emit a first first-color light, the second area may absorb the first light to emit a second first-color light, and the third area may absorb the first light to emit a third first-color light. In this regard, the first first-color light, the second first-color light, and the third first-color light may have different maximum emission wavelengths from one another. In more detail, the first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an activation layer, wherein any one selected from the source electrode and the drain electrode may be electrically coupled to any one selected from the anode and the cathode of the light-emitting device.

The thin-film transistor may further include a gate electrode, a gate insulating film, and/or the like.

The activation layer may include crystalline silicon, amorphous silicon, organic semiconductor, oxide semiconductor, and/or the like.

The electronic apparatus may further include a sealing portion for sealing the light-emitting device. The sealing portion and/or the color conversion layer may be placed between the color filter and the light-emitting device. The sealing portion allows light from the light-emitting device to be extracted to the outside, while concurrently or simultaneously preventing or reducing penetration of ambient air and/or moisture into the light-emitting device. The sealing portion may be a sealing substrate including a transparent glass substrate and/or a plastic substrate. The sealing portion may be a thin-film encapsulation layer including at least one layer of an organic layer and/or an inorganic layer. When the sealing portion is a thin film encapsulation layer, the electronic apparatus may be flexible.

Various suitable functional layers may be additionally on the sealing portion, in addition to the color filter and/or the color conversion layer, according to the use of the electronic apparatus. The functional layers may include a touch screen layer, a polarizing layer, and/or the like. The touch screen layer may be a pressure-sensitive touch screen layer, a capacitive touch screen layer, and/or an infrared touch screen layer. The authentication apparatus may be, for example, a biometric authentication apparatus that authenticates an individual by using biometric information of a living body (for example, fingertips, pupils, etc.).

The authentication apparatus may further include, in addition to the light-emitting device, a biometric information collector.

The electronic apparatus may be applied to various suitable displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, and/or endoscope displays), fish finders, various suitable measuring instruments, meters (for example, meters for a vehicle, an aircraft, and/or a vessel), projectors, and/or the like.

Figure 3:
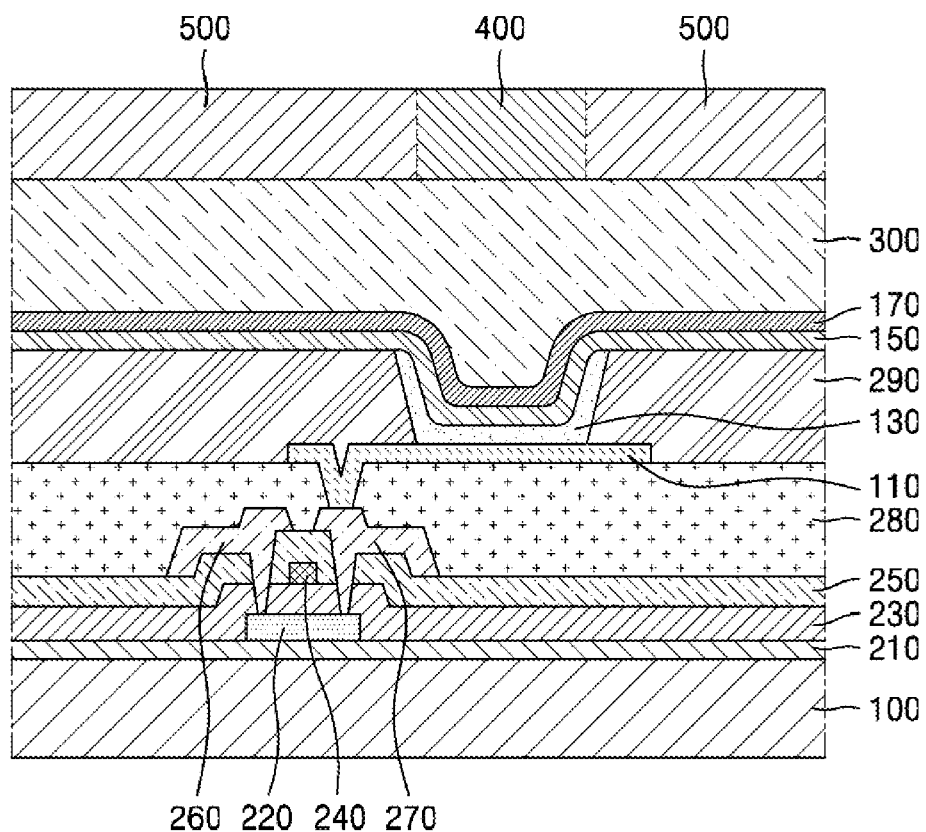
FIG. 3 is a schematic view of a light-emitting apparatus according to another embodiment.

Description of FIGS. 2 and 3

FIG. 2 is a cross-sectional view showing a light-emitting apparatus according to an embodiment of the present disclosure.

The light-emitting apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, and/or a metal substrate. A buffer layer 210 may be formed on the substrate 100. The buffer layer 210 may prevent or reduce penetration of impurities through the substrate 100 and may provide a flat surface (e.g., a substantially flat surface) on the substrate 100.

A TFT may be on the buffer layer 210. The TFT may include an activation layer 220, a gate electrode 240, a source electrode 260, and a drain electrode 270.

The activation layer 220 may include an inorganic semiconductor such as silicon and/or polysilicon, an organic semiconductor, and/or an oxide semiconductor, and may include a source region, a drain region and a channel region.

A gate insulating film 230 for insulating the activation layer 220 from the gate electrode 240 may be on the activation layer 220, and the gate electrode 240 may be on the gate insulating film 230.

An interlayer insulating film 250 may be on the gate electrode 240. The interlayer insulating film 250 may be between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be on the interlayer insulating film 250. The interlayer insulating film 250 and the gate insulating film 230 may be formed to expose the source region and the drain region of the activation layer 220, and the source electrode 260 and the drain electrode 270 may be in contact (e.g., physical contact) with the exposed portions of the source region and the drain region of the activation layer 220.

The TFT is electrically coupled to a light-emitting device to drive the light-emitting device, and is covered by a passivation layer 280. The passivation layer 280 may include an inorganic insulating film, an organic insulating film, or any combination thereof. A light-emitting device is provided on the passivation layer 280. The light-emitting device may include an anode 110, an interlayer 130, and a cathode 150.

The anode 110 may be on the passivation layer 280. The passivation layer 280 may not completely cover the drain electrode 270 and exposes a portion of the drain electrode 270, and the anode 110 is coupled to the exposed portion of the drain electrode 270.

A pixel defining layer 290 containing an insulating material may be on the anode 110. The pixel defining layer 290 may expose a region of the anode 110, and an interlayer 130 may be formed in the exposed region of the anode 110. The pixel defining layer 290 may include a polyimide and/or polyacrylic organic film. In some embodiments, at least some layers of the interlayer 130 may extend beyond the upper portion of the pixel defining layer 290 to be in the form of a common layer.

The cathode 150 may be on the interlayer 130, and a capping layer 170 may be additionally formed on the cathode 150. The capping layer 170 may be formed to cover the cathode 150.

The encapsulation portion 300 may be on the capping layer 170. The encapsulation portion 300 may be on a light-emitting device to protect the light-emitting device from moisture and/or oxygen. The encapsulation portion 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, and/or the like), an epoxy-based resin (for example, aliphatic glycidyl ether (AGE), and/or the like), or any combination thereof; or any combination of the inorganic film and the organic film.

FIG. 3 is a cross-sectional view of a light-emitting apparatus according to another embodiment of the present disclosure.

The light-emitting apparatus of FIG. 3 is substantially the same as the light-emitting apparatus of FIG. 2, except that a light-shielding pattern 500 and a functional region 400 are additionally on the encapsulation portion 300. The functional region 400 may be a combination of i) a color filter area, ii) a color conversion area, or iii) a combination of the color filter area and the color conversion area. In an embodiment, the light-emitting device included in the light-emitting apparatus of FIG. 3 may be a tandem light-emitting device.

Manufacture Method

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, the emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definition of at Least Some of the Terms The term "$C_3$-$C_{60}$ carbocyclic group," as used herein, refers to a cyclic group consisting of carbon only as a ring-forming atom and having three to sixty carbon atoms, and the term "$C_1$-$C_{60}$ heterocyclic group," as used herein, refers to a cyclic group that has one to sixty carbon atoms and further has, in addition to carbon, a heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are condensed with (e.g., combined together with) each other. In an embodiment, the number of ring-forming atoms of the $C_1$-$C_{60}$ heterocyclic group may be from 3 to 61.

The "cyclic group," as used herein, may include the $C_3$-$C_{60}$ carbocyclic group, and the $C_1$-$C_{60}$ heterocyclic group.

The term "π electron-rich $C_3$-$C_{60}$ cyclic group," as used herein, refers to a cyclic group that has three to sixty carbon atoms and does not include *—N=*' as a ring-forming moiety, and the term "π electron-deficient nitrogen-containing $C_1$-$C_{60}$ cyclic group" as used herein, refers to a heterocyclic group that has one to sixty carbon atoms and includes *—N=*' as a ring-forming moiety.

In an embodiment, the $C_3$-$C_{60}$ carbocyclic group may be i) group T1 or ii) a condensed cyclic group in which two or more groups T1 are condensed with (e.g., combined together with) each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be i) group T2, ii) a condensed cyclic group in which two or more groups T2 are condensed with (e.g., combined together with) each other, or iii) a condensed cyclic group in which at least one group T2 and at least one group T1 are condensed with (e.g., combined together with) each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be i) group T1, ii) a condensed cyclic group in which two or more groups T1 are condensed with (e.g., combined together with) each other, iii) group T3, iv) a condensed cyclic group in which two or more groups T3 are condensed with (e.g., combined together with) each other, or v) a condensed cyclic group in which at least one group T3 and at least one group T1 are condensed with (e.g., combined together with) each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be i) group T4, ii) a condensed cyclic group in which two or more groups T4 are condensed with (e.g., combined together with) each other, iii) a condensed cyclic group in which at least one group T4 and at least one group T1 are condensed with (e.g., combined together with) each other, iv) a condensed cyclic group in which at least one group T4 and at least one group T3 are condensed with (e.g., combined together with) each other, or v) a condensed cyclic group in which at least one group T4, at least one group T1, and at least one group T3 are condensed with (e.g., combined together with) one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group, group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, group T3 may be a furan group, a thiophene group, a 1H-pyrrole group, a silole group, or a borole group, and group T4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group," "the $C_3$-$C_{60}$ carbocyclic group," "the $C_1$-$C_{60}$ heterocyclic group," "the π electron-rich $C_3$-$C_{60}$ cyclic group," or "the π electron-deficient nitrogen-containing $C_1$-$C_{60}$ cyclic group," as used herein, refer to a group condensed to any cyclic group or a polyvalent group (for example, a divalent group, a trivalent group, a tetravalent group, etc.), depending on the structure of a formula in connection with which the terms are used. In an embodiment, "a benzene group" may be a benzo group, a phenyl group, a phenylene group, or the like, which may be easily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the monovalent $C_1$-$C_{60}$ heterocyclic group are a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group," as used herein, refers to a linear or branched aliphatic hydrocarbon monovalent group that has one to sixty carbon atoms, and examples thereof include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a monovalent hydrocarbon group having at least one carbon-carbon double bond at a main chain (e.g., in the middle) or at a terminal end (e.g., the terminus) of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a monovalent hydrocarbon group having at least one carbon-carbon triple bond at a main chain (e.g., in the middle) or at a terminal end (e.g., the terminus) of the $C_2$-$C_{60}$ alkyl group, and examples thereof include an ethynyl group and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon cyclic group having 3 to 10 carbon atoms, and examples thereof include a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent cyclic group that further includes, in addition to a carbon atom, at least one heteroatom as a ring-forming atom and has 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent cyclic group that has 3 to 10 carbon atoms and at least one carbon-carbon double bond in the ring thereof and no aromaticity (e.g., is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Examples of the $C_6$-$C_{60}$ aryl group include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be condensed with (e.g., combined together with) each other.

The term "$C_1$-$C_{60}$ heteroaryl group," as used herein, refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group," as used herein, refers to a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be condensed with (e.g., combined together with) each other.

The term "monovalent non-aromatic condensed polycyclic group," as used herein, refers to a monovalent group (for example, having 8 to 60 carbon atoms) having two or more rings condensed to each other (e.g., combined together with each other), only carbon atoms as ring-forming atoms, and no aromaticity in its entire molecular structure (e.g., no aromatic conjugation system extends across the entire structure, although portions of the group may contain conjugated systems). Examples of the monovalent non-aromatic condensed polycyclic group include an indenyl group, a fluorenyl group, a spiro-bifluorenyl group, a benzofluorenyl group, an indenophenanthrenyl group, and an indeno anthracenyl group. The term "divalent non-aromatic condensed polycyclic group," as used herein, refers to a divalent group having substantially the same structure as a monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together with each other), at least one heteroatom other than carbon atoms, as a ring-forming atom, and non-aromaticity in its entire molecular structure (e.g., no aromatic conjugation system extends across the entire structure, although portions of the group may contain conjugated systems). Examples of the monovalent non-aromatic condensed heteropolycyclic group include a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic heterocondensed polycyclic group," as used herein, refers to a divalent group having substantially the same structure as a monovalent non-aromatic heterocondensed polycyclic group.

The term "$C_6$-$C_{60}$ aryloxy group," as used herein, indicates —$OA_{102}$ (wherein $A_{102}$ is the $C_6$-$C_{60}$ aryl group), and the term "$C_6$-$C_{60}$ arylthio group," as used herein, indicates —$SA_{103}$ (wherein $A_{103}$ is the $C_6$-$C_{60}$ aryl group).

The term "$C_7$-$C_{60}$ aryl alkyl group," as used herein, refers to -$A_{104}A_{105}$ (where $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group," as used herein, refers to -$A_{106}A_{107}$ (where $A_{106}$ may be a $C_1$-$C_{59}$ alkylene group, and $A_{107}$ may be a $C_1$-$C_{59}$ heteroaryl group).

The term "$R_{10a}$," as used herein, refers to:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with -D, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with -D, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

$Q_{11}$ to $Q_{13}$, $Q_{21}$ to $Q_{23}$, and $Q_{31}$ to $Q_{33}$, as described herein may each independently be: hydrogen; -D; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with -D, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom," as used herein, refers to any atom other than a carbon atom. Examples of the heteroatom are O, S, N, P, Si, B, Ge, Se, and any combination thereof.

The term "the third-row transition metal," as used herein, includes hafnium (Hf), tantalum (Ta), tungsten (W), rhenium (Re), osmium (Os), iridium (Ir), platinum (Pt), gold (Au), etc.

The term "Ph," as used herein, refers to a phenyl group, the term "Me," as used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a substituted phenyl group having, as a substituent, a $C_6$-$C_{60}$ aryl group substituted with a $C_6$-$C_{60}$ aryl group.

* and *', as used herein, unless defined otherwise, each refer to a binding site to a neighboring atom in a corresponding formula or moiety.

EXAMPLES

Evaluation Example 1: Measurement of Charge Mobility

A hole only device (HOD) including Compounds of Table 1 was manufactured, and a current amount according to a voltage of the HOD was measured. A current-voltage graph was fitted to find an interval in which a space charge limited current (SCLC) was formed, and then, the charge mobility was calculated therefrom. Results thereof are shown in Table 1.

TABLE 1

| Compound No. | Charge mobility (cm$^2$/Vs) |
| --- | --- |
| 1 | $4.27 \times 10^{-5}$ |
| 2 | $4.05 \times 10^{-5}$ |
| 3 | $5.31 \times 10^{-5}$ |
| 4 | $3.64 \times 10^{-5}$ |
| HT3 | $1.37 \times 10^{-4}$ |
| β-NPB | $1.48 \times 10^{-4}$ |

Example 1

As an anode, an ITO substrate was cut to a size of 50 mm×50 mm×0.5 mm, respectively sonicated with acetone, isopropyl alcohol, and pure water each for 5 minutes, and then cleaned by exposure to ultraviolet rays and ozone for 30 minutes. Then, the ITO substrate was provided to a vacuum deposition apparatus.

Compound 1 was deposited on the ITO substrate to form a first layer having a thickness of 15 nm (NDP9 1 wt % doping, 1 nm), HT3 was vacuum-deposited on the first layer to form a second layer having a thickness of 85 nm, an emission layer was formed on the second layer, and an electron transport layer was formed on the emission layer. Al was deposited on the electron transport layer to form a cathode having a thickness of 1,200 Å, thereby completing the manufacture of a light-emitting device.

Examples 2 to 3 and Comparative Examples 1 to 3

Light-emitting devices were manufactured in substantially the same manner as in Example 1, except that a first layer and a second layer were formed by using Compounds shown in Table 2.

Evaluation Example 2

With respect to the light-emitting devices manufactured according to Examples 1 to 3 and Comparative Examples 1 and 3, an amount of the current flowing in an anode of a subpixel closest to the subpixel into which the current was injected was measured under a driving voltage of 0 V to 9 V by a probe station. Results thereof are shown in Table 2 and FIG. 4.

TABLE 2

| | First layer | Second layer | Lateral current loss (%) |
| --- | --- | --- | --- |
| Example 1 | Compound 1 | HT3 | 29 |
| Example 2 | Compound 2 | HT3 | 30 |
| Example 3 | Compound 3 | HT3 | 16 |
| Comparative Example 1 | HT3 | HT3 | 100 |
| Comparative Example 2 | β-NPB | HT3 | 85 |
| Comparative Example 3 | HT3 | β-NPB | 93 |

Figure 4:
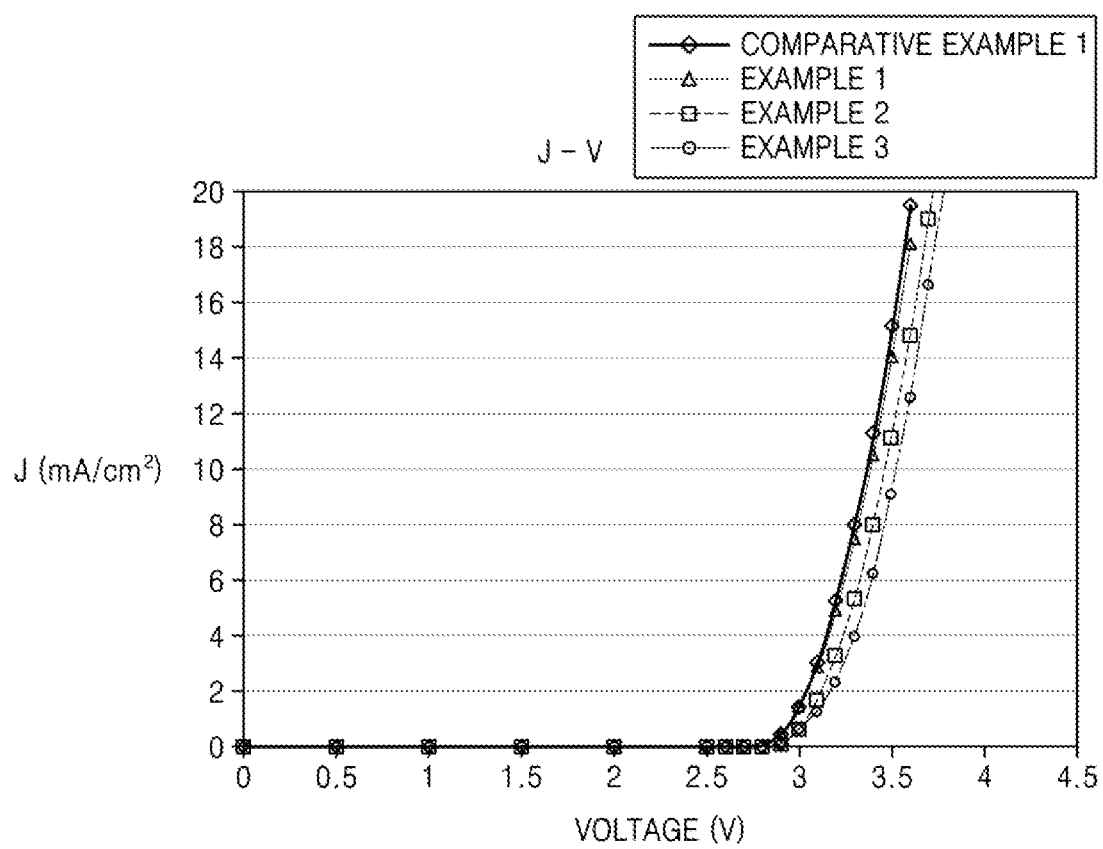
FIG. 4 is a graph of a lateral current amount according to a driving voltage of Examples 1 to 3 and Comparative Example 1.

Referring to Table 2 and FIG. 4, it can be seen that Example 1, Example 2, and Example 3 show lateral the current loss of about 29%, about 30%, and about 16%, respectively, with respect to the lateral current loss of Comparative Example 1.

In the cases of Comparative Examples 2 and 3, the lateral current loss was about 85% and about 93%, respectively, with respect to the lateral current loss of Comparative Example 1, and thus, no significant improvement was shown.

Evaluation Example 3

The driving voltage and current density of the light-emitting devices manufactured according to Examples 1 to 3 and Comparative Example 1 were measured by using a source meter (Keithley Instrument, 2400 Series). A J-V graph thereof is shown in FIG. 5.

Figure 5:
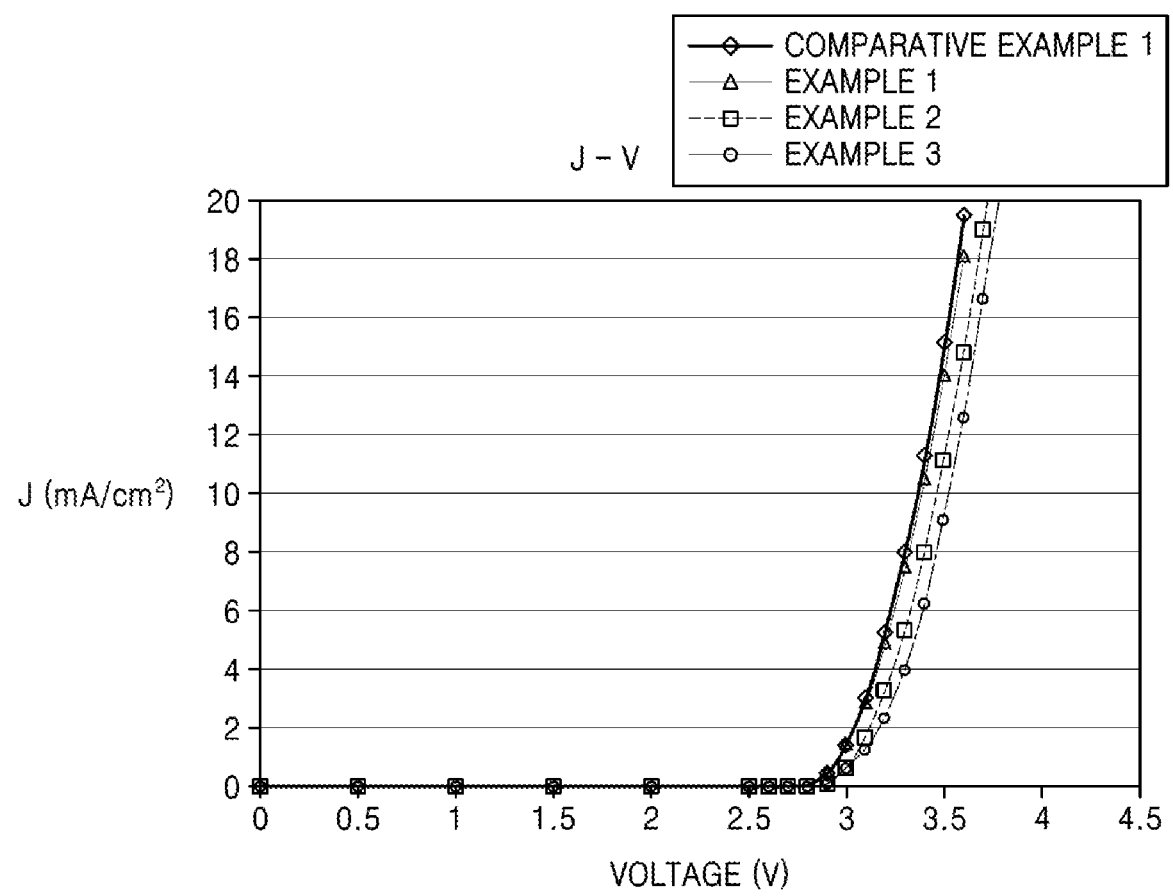
FIG. 5 is a graph of current versus driving voltage of Examples 1 to 3 and Comparative Example 1.

Referring FIG. 5, it can be seen that Examples 1 to 3 each show a J-V curve equivalent to that of Comparative Example 1. From these results, it can be seen that Examples 1 to 3 may reduce only the lateral current loss without current loss in the vertical direction.

A light-emitting device having reduced lateral current loss may be provided.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims, and equivalents thereof.

What is claimed is:

1. A light-emitting device comprising:
an anode;
a cathode;
an interlayer comprising an emission layer between the anode and the cathode; and
a hole transport region between the anode and the emission layer,
wherein the hole transport region comprises a first layer and a second layer,
the first layer is between the anode and the second layer,
the first layer comprises a first compound represented by Formula 1,
the second layer comprises a second compound, and
a charge mobility of the first compound is lower than a charge mobility of the second compound:

Formula 1

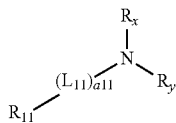

wherein, in Formula 1,
$L_{11}$ is a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$,
a11 is an integer from 0 to 5,
$R_x$ and $R_y$ are each a group represented by Formula 2, and $R_x$ and $R_y$ are identical to each other, Formula 2

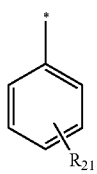

wherein, in Formula 2,
$R_{21}$ is a cyclopentyl group, a cyclohexyl group, a tert-butyl group, or a $C_5$-$C_{10}$ alkyl group, and
$R_{10a}$ is:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with -D, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{11})(Q_{12})(Q_{13})$, —C$(Q_{11})(Q_{12})(Q_{13})$, —B$(Q_{11})(Q_{12})$, —N$(Q_{11})(Q_{12})$, —P$(Q_{11})(Q_{12})$, —C(=O)$(Q_{11})$, —S(=O)$(Q_{11})$, —S(=O)$_2(Q_{11})$, —P(=O)$(Q_{11})(Q_{12})$, —P(=S)$(Q_{11})(Q_{12})$, or any combination thereof;
a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with -D, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{21})(Q_{22})(Q_{23})$, —C$(Q_{21})(Q_{22})(Q_{23})$, —B$(Q_{21})(Q_{22})$, —N$(Q_{21})(Q_{22})$, —P$(Q_{21})(Q_{22})$, —C(=O)$(Q_{21})$, —S(=O)$(Q_{21})$, —S(=O)$_2(Q_{21})$, —P(=O)$(Q_{21})(Q_{22})$ or —P(=S)$(Q_{21})(Q_{22})$, or any combination thereof; or
—Si$(Q_{31})(Q_{32})(Q_{33})$, —C$(Q_{31})(Q_{32})(Q_{33})$, —B$(Q_{31})(Q_{32})$, —N$(Q_{31})(Q_{32})$, —P$(Q_{31})(Q_{32})$, —C(=O)$(Q_{31})$, —S(=O)$(Q_{31})$, —S(=O)$_2(Q_{31})$, —P(=O)$(Q_{31})(Q_{32})$, or —P(=S)$(Q_{31})(Q_{32})$,
wherein $Q_{11}$ to $Q_{13}$, $Q_{21}$ to $Q_{23}$, and $Q_{31}$ to $Q_{33}$ are each independently: hydrogen; -D; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with -D, —F, a cyano group, a $C_1$-$C_{60}$ alkyl group, a $C_1$-$C_{60}$ alkoxy group, a phenyl group, a biphenyl group, or any combination thereof,

* indicates a binding site to a neighboring atom, wherein $R_{11}$ is a group represented by one selected from Formulae 6-1 to 6-173:

6-1

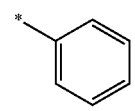

6-2

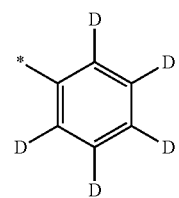

6-3

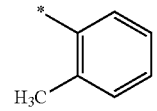

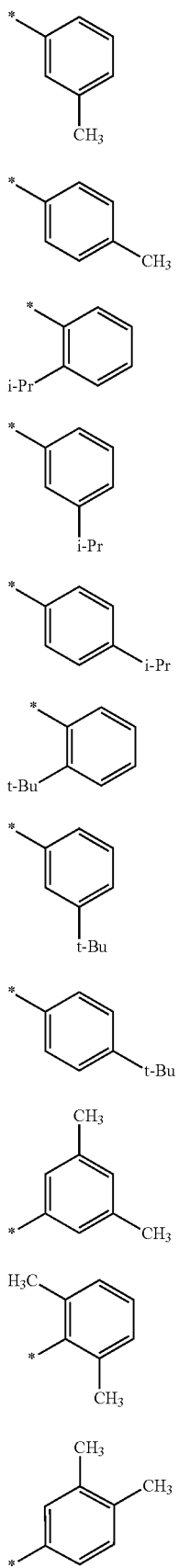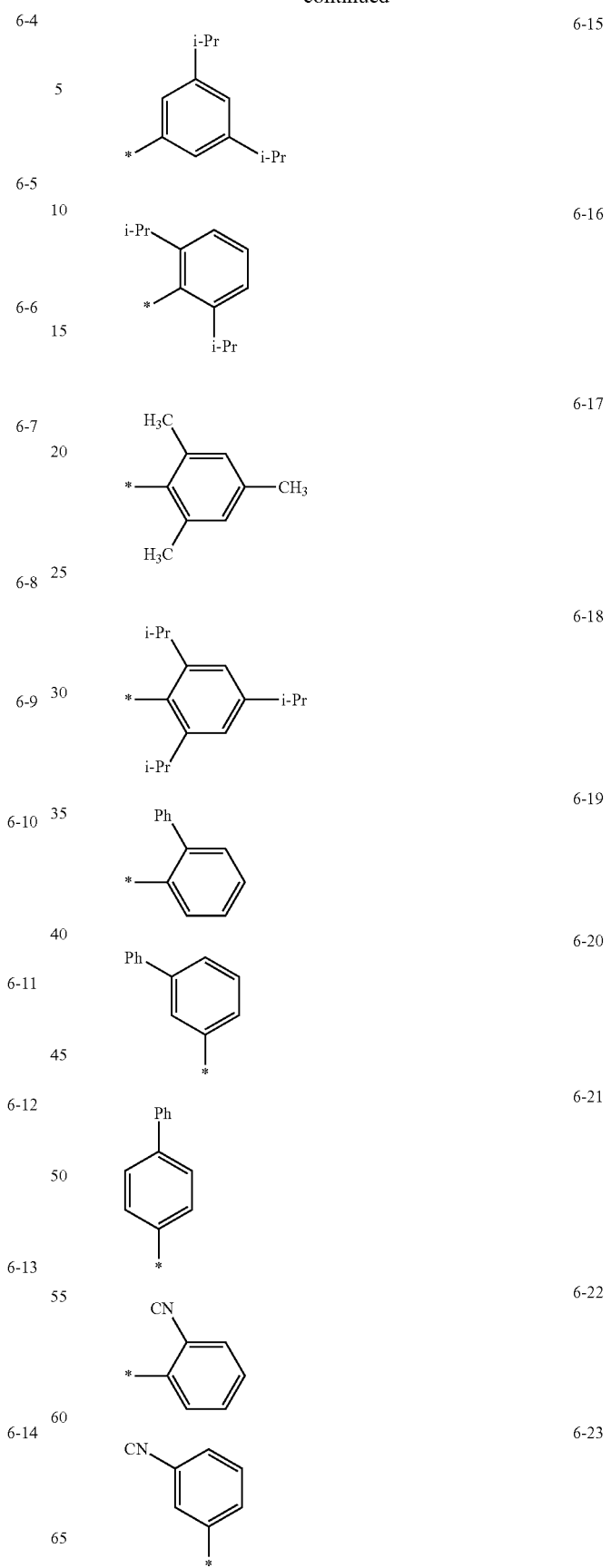

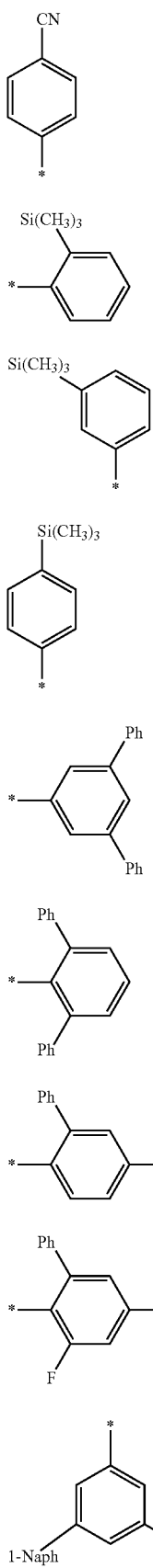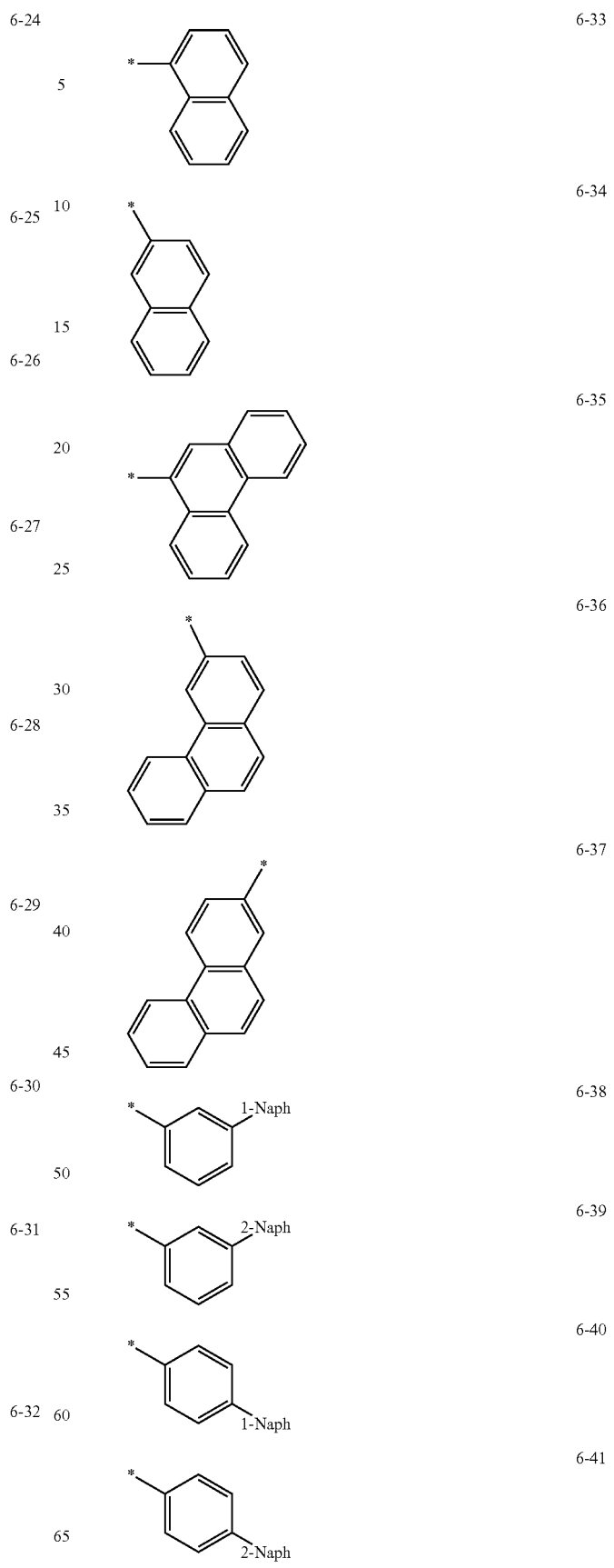

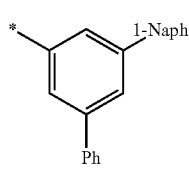
6-42
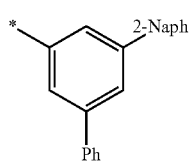
6-43
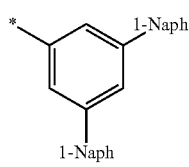
6-44
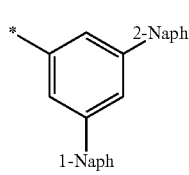
6-45
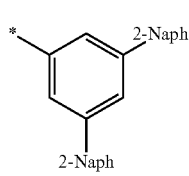
6-46
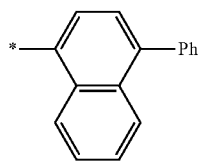
6-47
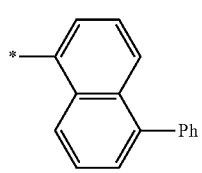
6-48
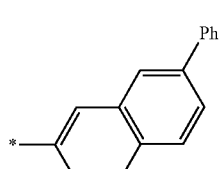
6-49
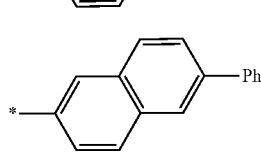
6-50
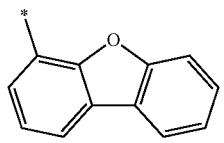
6-51
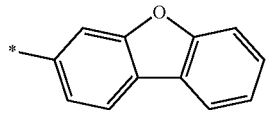
6-52
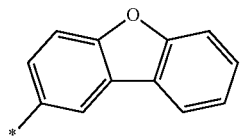
6-53
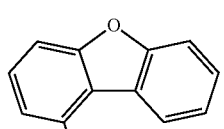
6-54
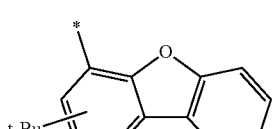
6-55
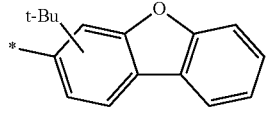
6-56
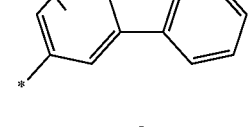
6-57
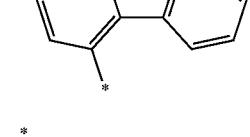
6-58
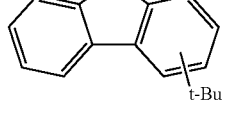
6-59
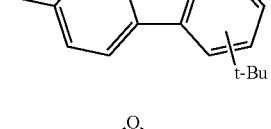
6-60
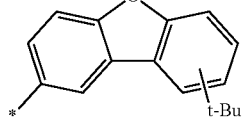
6-61

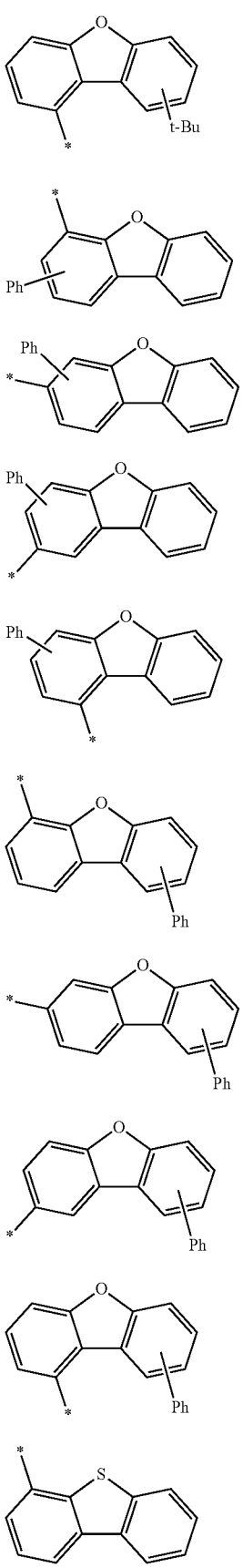
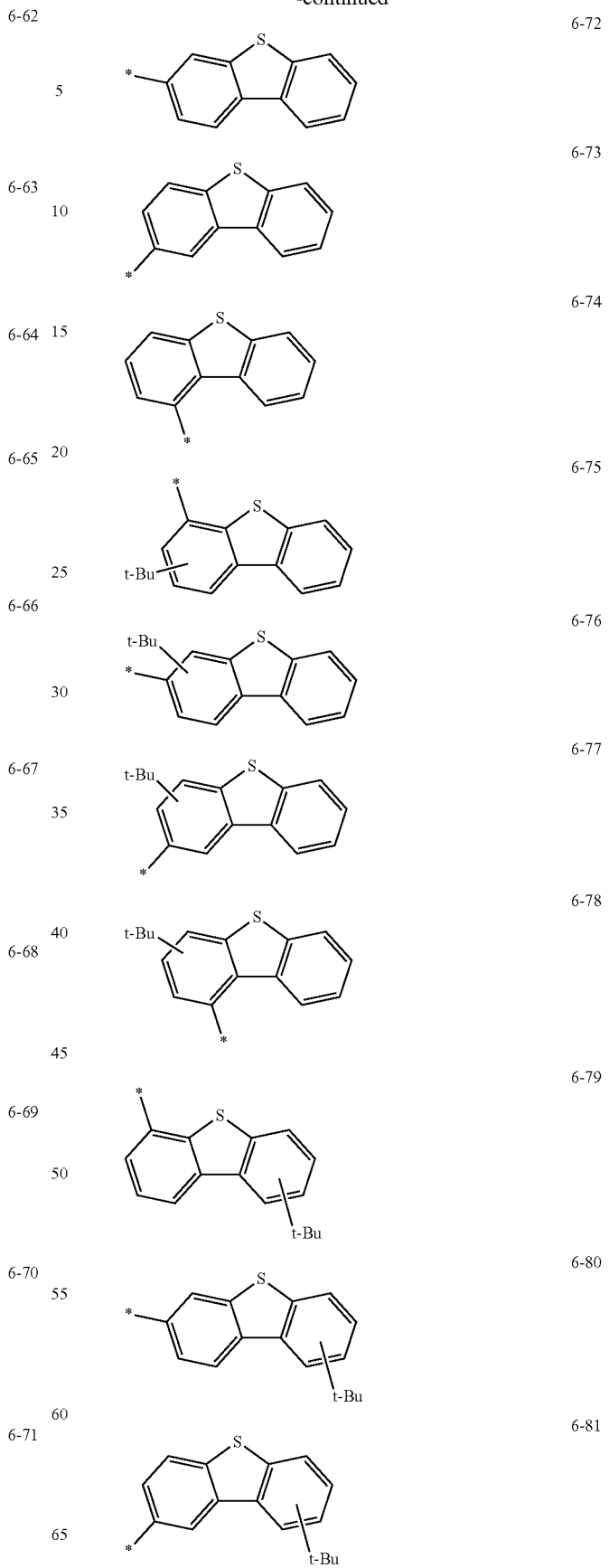

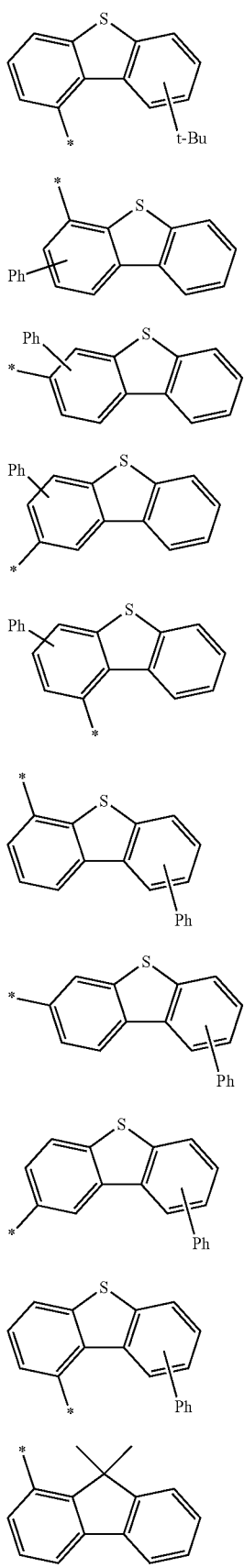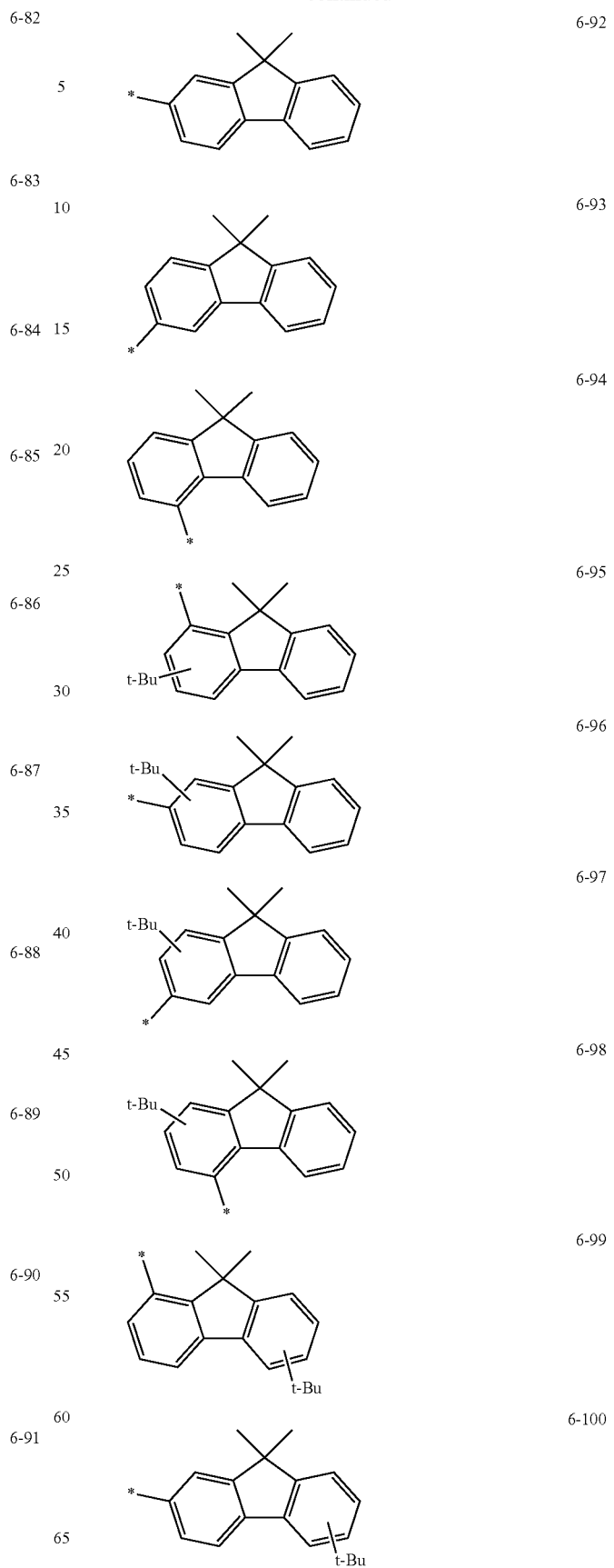

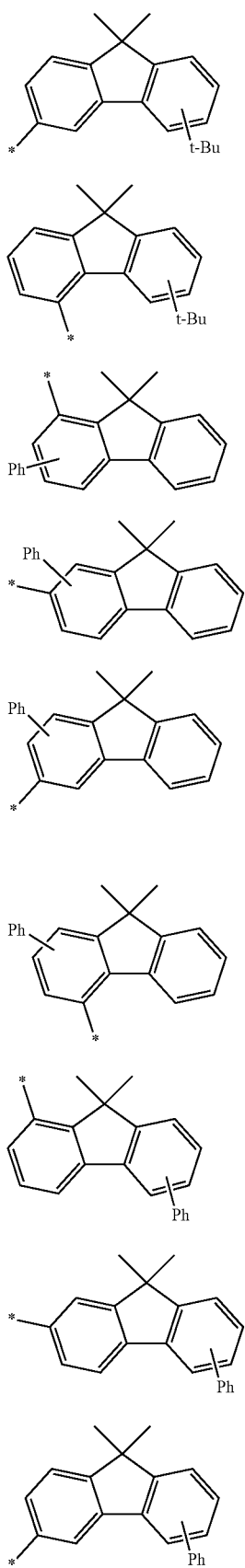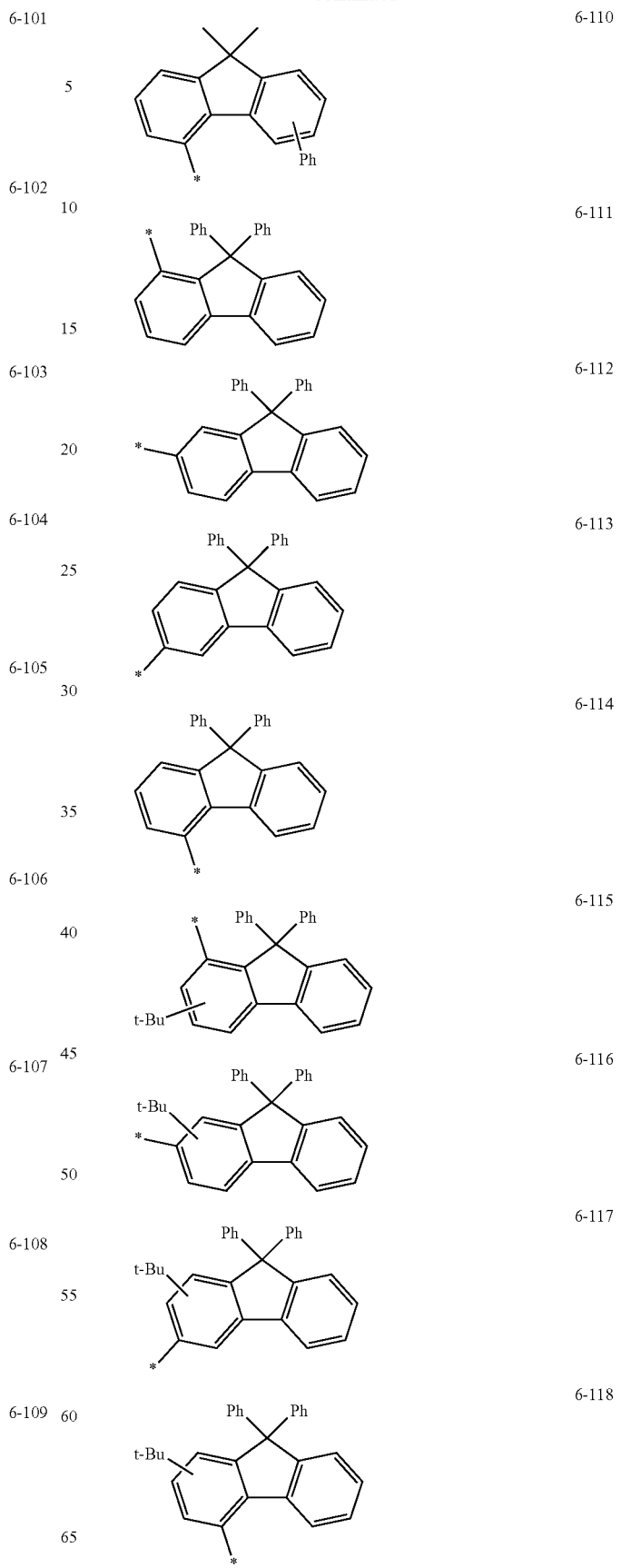

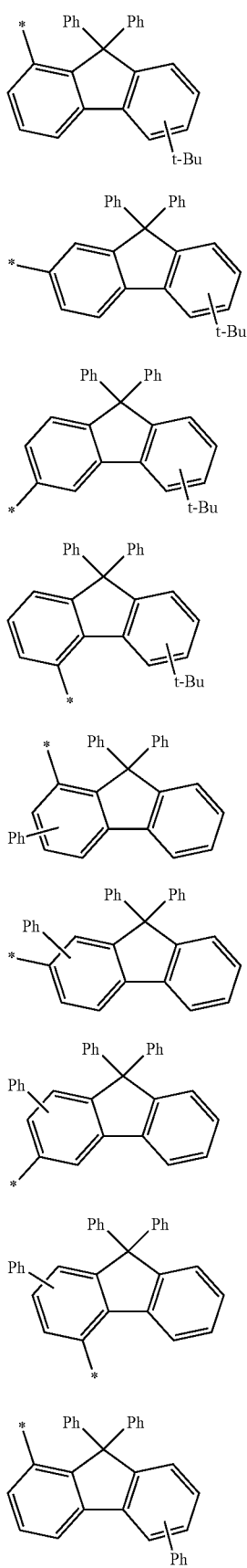
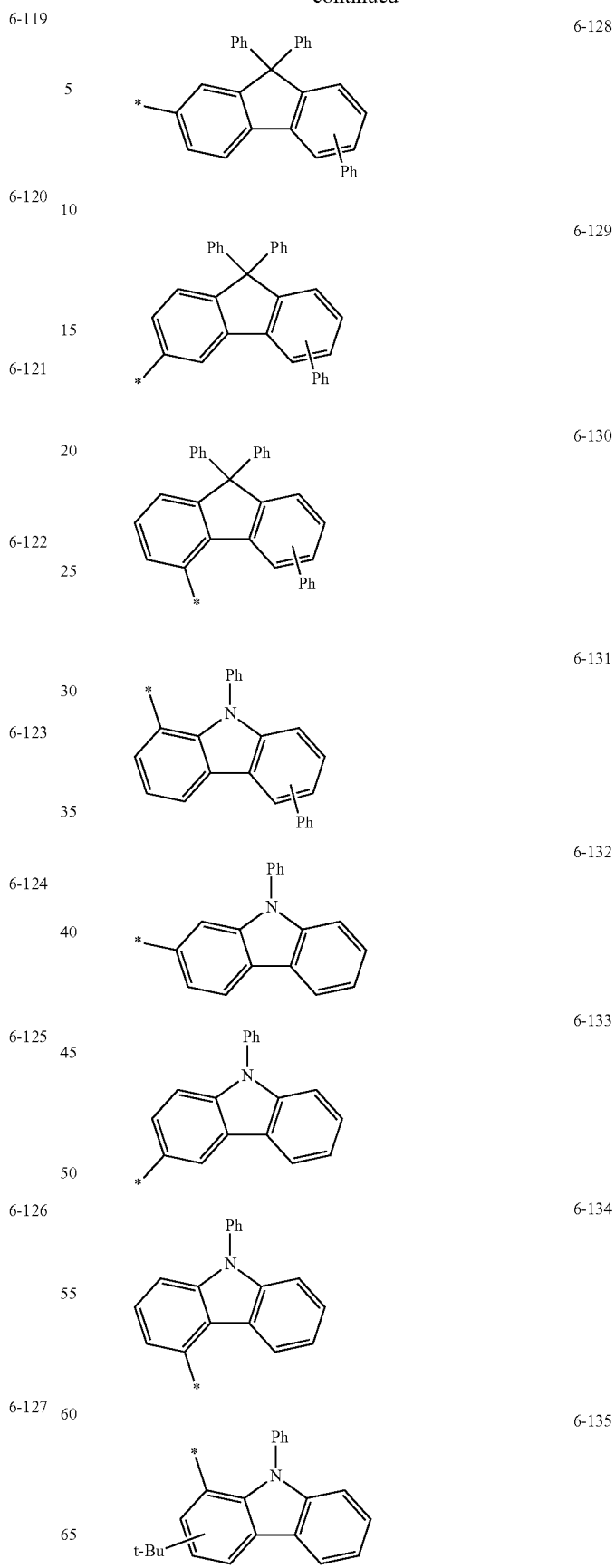

-continued
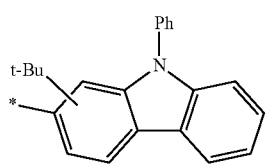 6-136
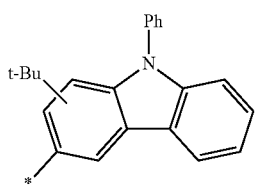 6-137
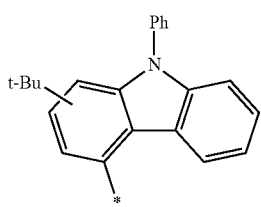 6-138
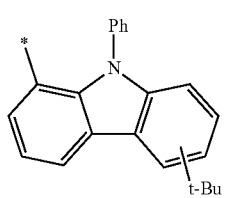 6-139
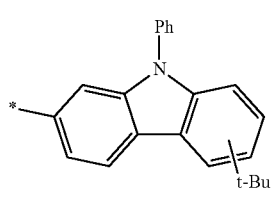 6-140
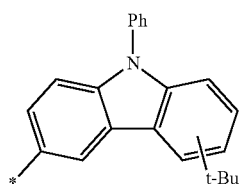 6-141
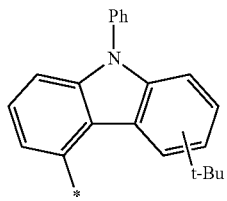 6-142
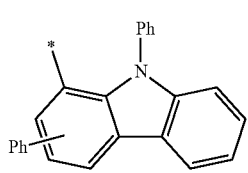 6-143
-continued
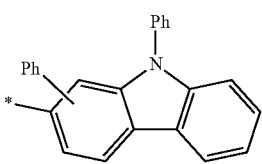 6-144
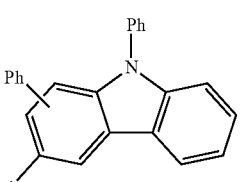 6-145
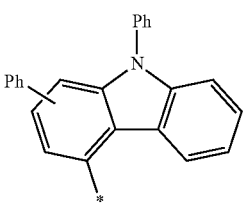 6-146
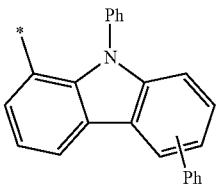 6-147
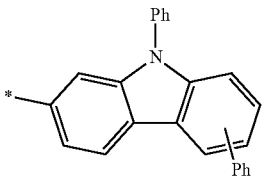 6-148
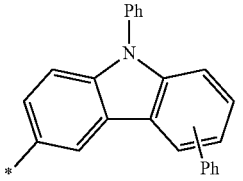 6-149
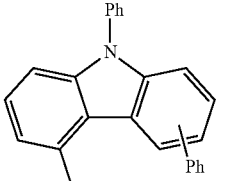 6-150
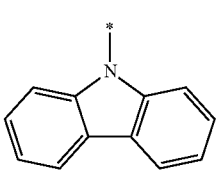 6-151

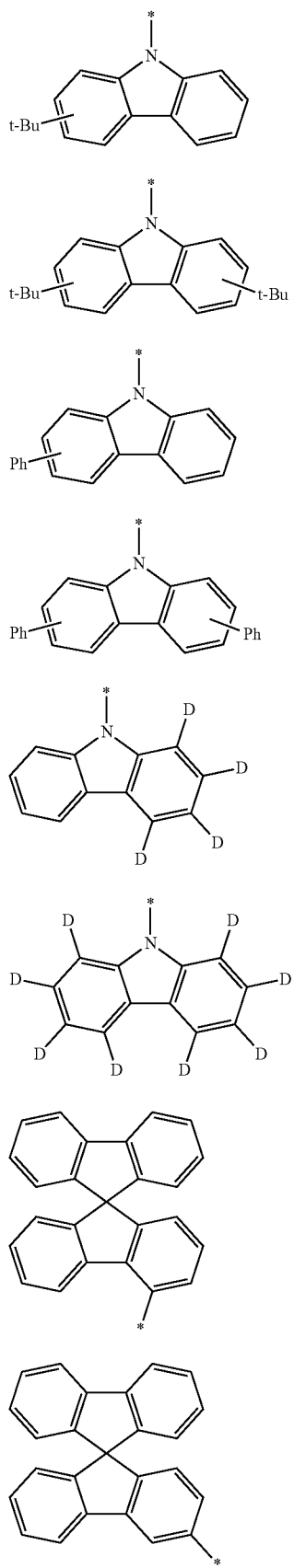
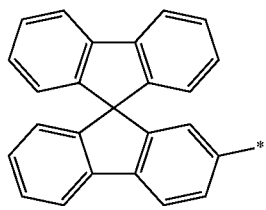
6-152
6-153
6-154
6-155
6-156
6-157
6-158
6-159
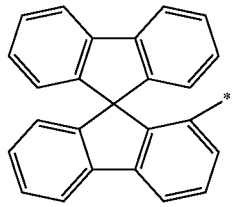
6-160
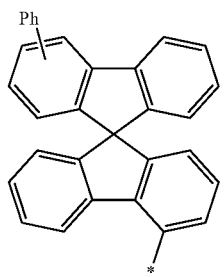
6-161
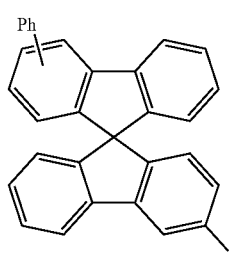
6-162
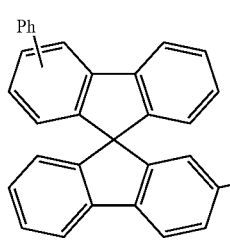
6-163
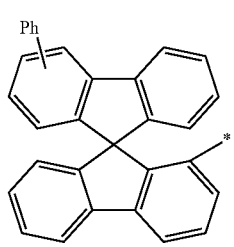
6-164
6-165

6-166 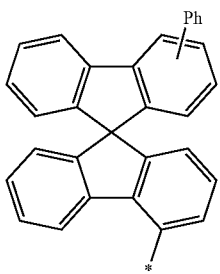

6-167 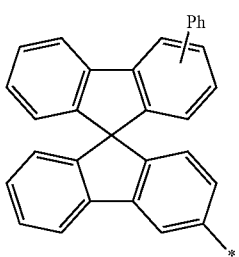

6-168 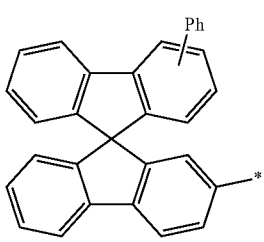

6-169 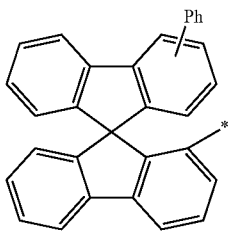

6-170 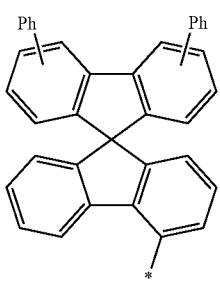

6-171 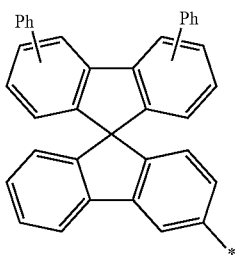

6-172 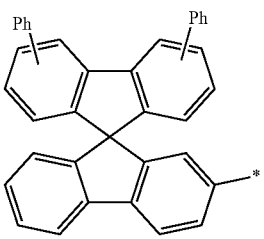

6-173 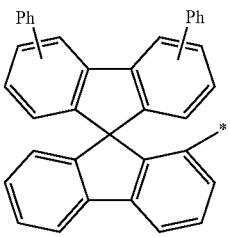

wherein, in Formulae 6-1 to 6-173,
i-Pr is an isopropyl group;
t-Bu is a tert-butyl group;
Ph is a phenyl group;
1-Naph is an 1-naphthyl group;
2-Naph is a 2-naphthyl group; and
* indicates a binding site to a neighboring atom, and
wherein when $R_{11}$ is represented by one selected from Formulae 5-10 to 5-13 and $X_{51}$ is $C(R_{53})(R_{54})$ and $R_{53}$ and $R_{54}$ are each independently a $C_1$-$C_{20}$ alkyl group, then $R_{21}$ is a tert-butyl group, wherein b54 is an integer from 1 to 4, b55 is an integer from 1 to 3, and $R_{51}$ and $R_{52}$ are each independently hydrogen, -D, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one phenyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrimidinyl group, a pyrazinyl group, a triazinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a dibenzofuranyl group, a dibenzothiophenyl group, a dibenzosilolyl group, —Si($Q_{31}$)($Q_{32}$)($Q_{33}$), —C($Q_{31}$)($Q_{32}$)($Q_{33}$), —N($Q_{31}$)($Q_{32}$), or —B($Q_{31}$)($Q_{32}$), 5-10 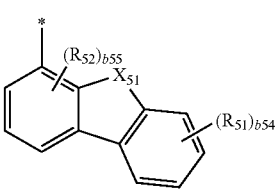

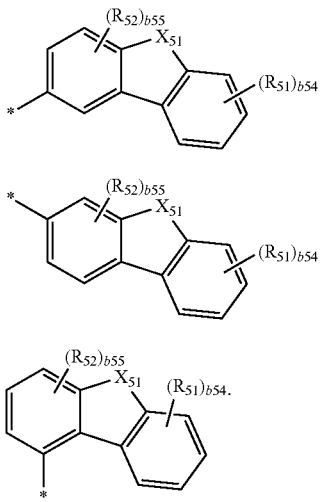

2. The light-emitting device of claim 1, wherein the charge mobility of the first compound is $1\times10^{-6}$ cm$^2$/Vs or more.

3. The light-emitting device of claim 1, wherein the charge mobility of the first compound is from about $5\times10^{-6}$ cm$^2$/Vs to about $5\times10^{-5}$ cm$^2$/Vs, and
the charge mobility of the second compound is from about $1\times10^{-4}$ cm$^2$/Vs to about $9\times10^{-4}$ cm$^2$/Vs.

4. The light-emitting device of claim 1, wherein a thickness of the first layer is 30 nm or less.

5. The light-emitting device of claim 1, wherein the first layer further comprises a charge-generation material.

6. The light-emitting device of claim 1, wherein $L_{11}$ is a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a dibenzofuran group, a dibenzothiophene group, a carbazole group, a benzosilole group, a dibenzosilole group, a quinoline group, an isoquinoline group, a benzimidazole group, an imidazopyridine group, or an imidazopyrimidine group, each unsubstituted or substituted with -D, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a triazinyl group, a benzofuranyl group, a benzothiophenyl group, a dibenzofuranyl group, a dibenzothiophenyl group, a carbazolyl group, a benzosilolyl group, a dibenzosilolyl group, a quinolinyl group, an isoquinolinyl group, a benzimidazolyl group, an imidazopyridinyl group, an imidazopyrimidinyl group, —Si(Q$_{31}$)(Q$_{32}$)(Q$_{33}$), —C(Q$_{31}$)(Q$_{32}$)(Q$_{33}$), —B(Q$_{31}$)(Q$_{32}$), —N(Q$_{31}$)(Q$_{32}$), —P(Q$_{31}$)(Q$_{32}$), —C(=O)(Q$_{31}$), —S(=O)(Q$_{31}$), —S(=O)$_2$(Q$_{31}$), —P(=O)(Q$_{31}$)(Q$_{32}$), —P(=S)(Q$_{31}$)(Q$_{32}$), or any combination thereof.

7. The light-emitting device of claim 1, wherein $L_{11}$ is a group represented by one selected from Formulae 3-1 to 3-38:

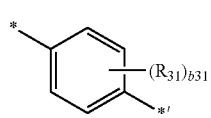

3-1

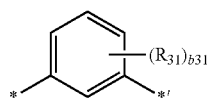

3-2

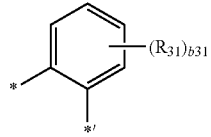

3-3

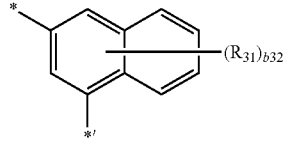

3-4

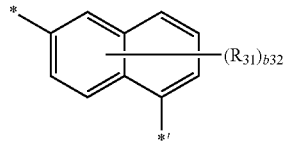

3-5

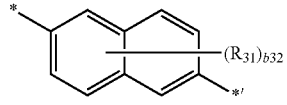

3-6

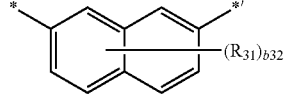

3-7

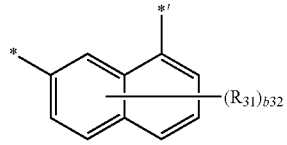

3-8

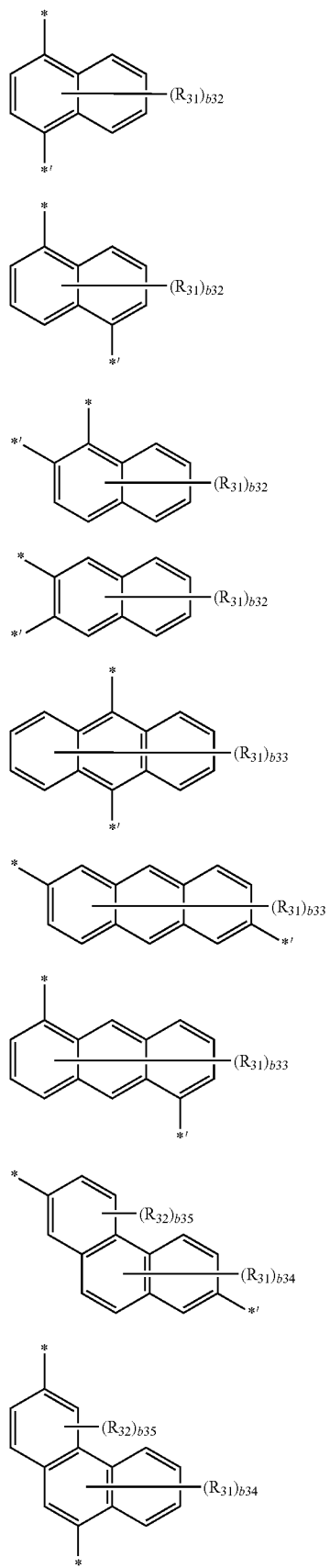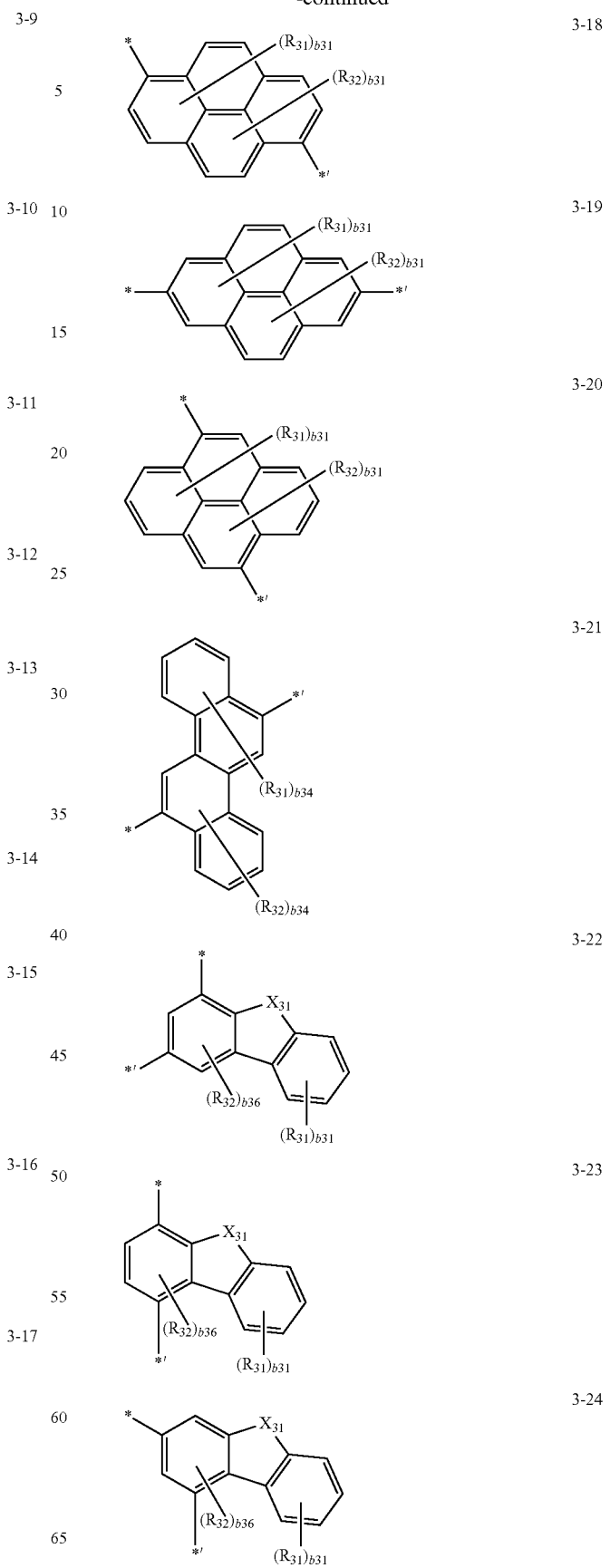

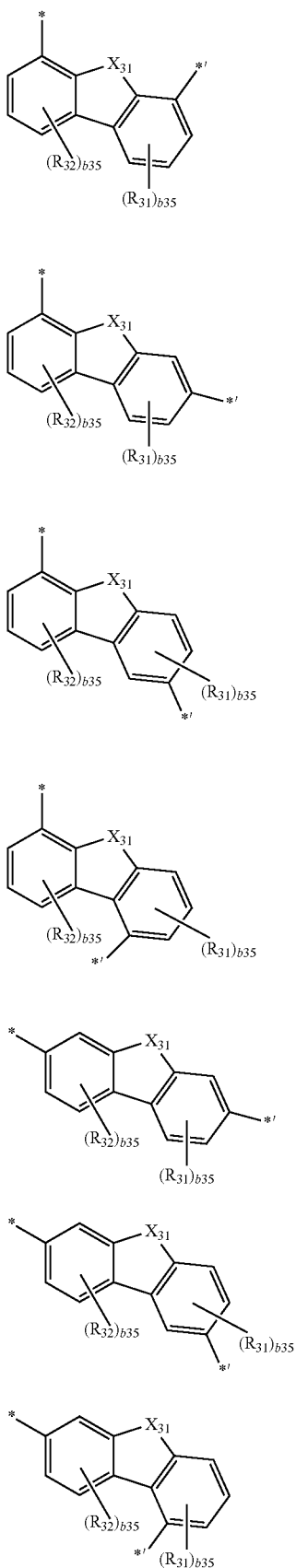
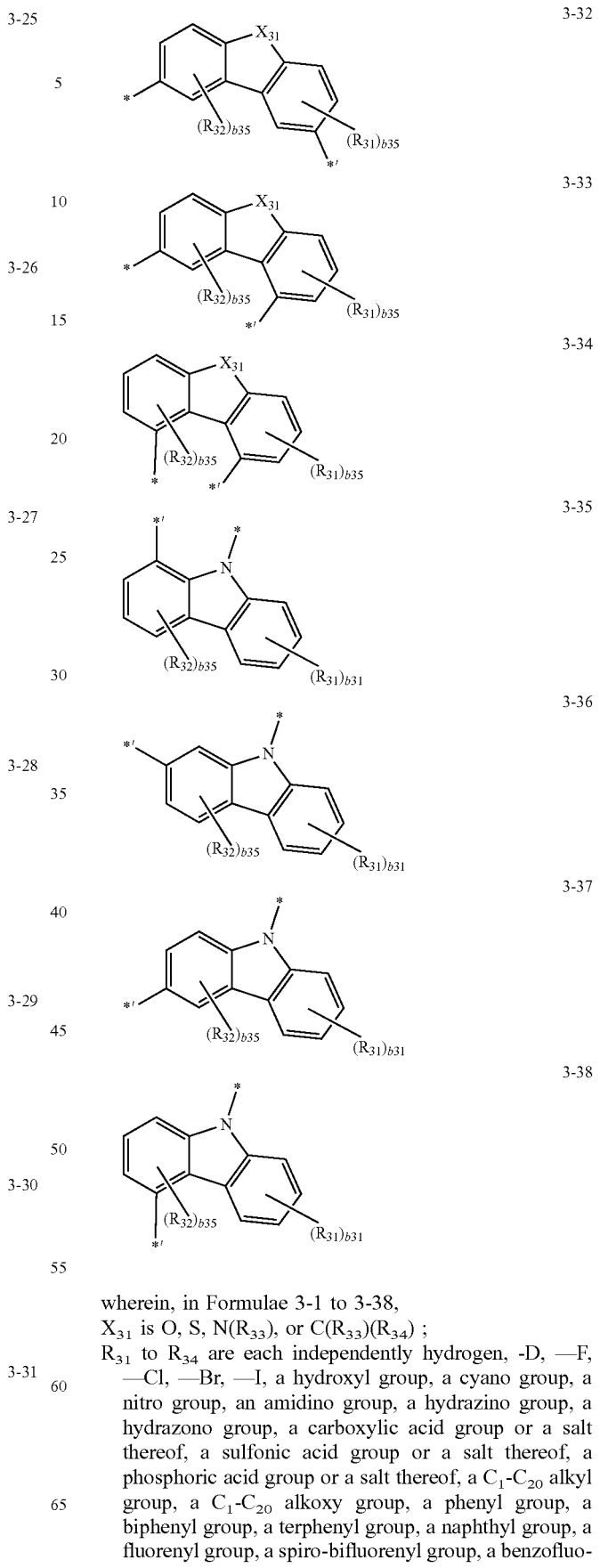

wherein, in Formulae 3-1 to 3-38,
$X_{31}$ is O, S, N($R_{33}$), or C($R_{33}$)($R_{34}$);
$R_{31}$ to $R_{34}$ are each independently hydrogen, -D, —F, —Cl, —Br, —I, a hydroxyl group, a cyano group, a nitro group, an amidino group, a hydrazino group, a hydrazono group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a carbazolyl group, a dibenzofuranyl group, a dibenzothiophenyl group, a triazinyl group, a benzimidazolyl group, a phenanthrolinyl group, —Si$(Q_{31})(Q_{32})(Q_{33})$, —C$(Q_{31})(Q_{32})(Q_{33})$, —N$(Q_{31})(Q_{32})$, or —B$(Q_{31})(Q_{32})$, $Q_{31}$ to $Q_{33}$ are each independently a $C_1$-$C_{10}$ alkyl group, a $C_1$-$C_{10}$ alkoxy group, a phenyl group, a phenyl group substituted with a cyano group, a biphenyl group, a terphenyl group, or a naphthyl group, b31 is an integer from 0 to 4, b32 is an integer from 0 to 6, b33 is an integer from 0 to 8, b34 is an integer from 0 to 5, b35 is an integer from 0 to 3, b36 is an integer from 0 to 2, and

* and *' each indicate a binding site to a neighboring atom.

8. The light-emitting device of claim 1, wherein $R_x$ and $R_y$ are each a group represented by one selected from Formulae 2-1 to 2-3, and $R_x$ and $R_y$ are identical to each other:

2-1
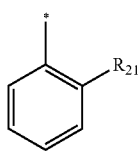

2-2
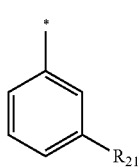

2-3
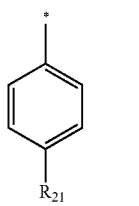

wherein, in Formulae 2-1 to 2-3, $R_{21}$ is a cyclohexyl group, a tert-butyl group, or an n-hexyl group, and

* indicates a binding site to a neighboring atom.

9. The light-emitting device of claim 8, wherein $R_x$ and $R_y$ are each a group represented by Formula 2-3, and $R_x$ and $R_y$ are identical to each other.

10. The light-emitting device of claim 1, wherein $R_x$ and $R_y$ are each a group represented by Formula 2-11, or $R_x$ and $R_y$ are each a group represented by Formula 2-12:

2-11
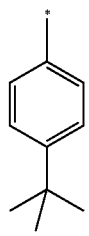

2-12
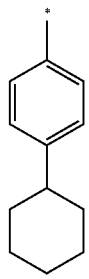

wherein, in Formulae 2-11 and 2-12,

* indicates a binding site to a neighboring atom.

11. The light-emitting device of claim 1, wherein the second compound is represented by Formula 201:

Formula 201
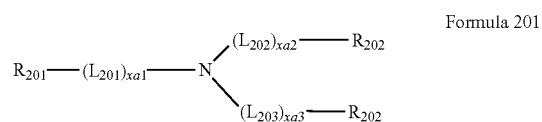

wherein, in Formula 201, $L_{201}$ to $L_{203}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xa1 to xa3 are each independently an integer from 0 to 5, $R_{201}$ to $R_{203}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and $R_{201}$ and $R_{202}$ are optionally linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$.

12. The light-emitting device of claim 11, wherein the second compound comprises at least one selected from groups represented by Formulae CY201 to CY217:

CY201
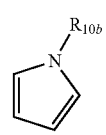

CY202
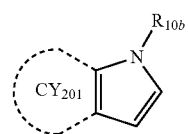

-continued

CY203 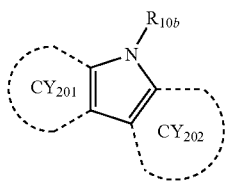

CY204 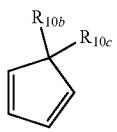

CY205 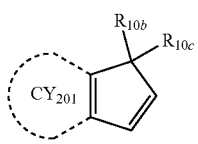

CY206 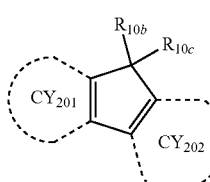

CY207 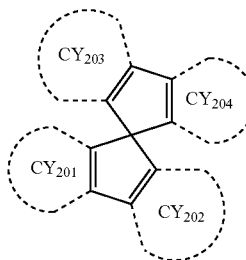

CY208 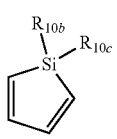

CY209 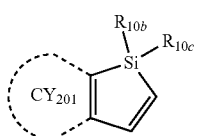

CY210 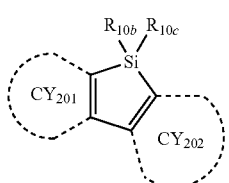

-continued

CY211 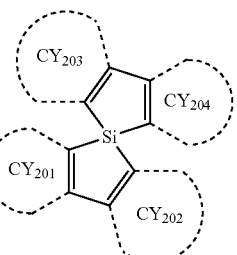

CY212 

CY213 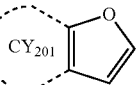

CY214 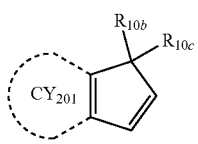

CY215 

CY216 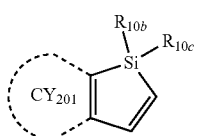

CY217 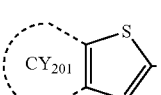

wherein, in Formulae CY201 to CY217, $R_{10b}$ and $R_{10c}$ are the same as described in connection with $R_{10a}$, ring CY201 to ring CY204 are each independently a $C_3$-$C_{20}$ carbocyclic group or a $C_1$-$C_{20}$ heterocyclic group, and at least one hydrogen in Formulae CY201 to CY217 is unsubstituted or substituted with $R_{10a}$.

13. The light-emitting device of claim 12, wherein the second compound comprises at least one selected from groups represented by Formulae CY201 to CY203 and at least one selected from groups represented by Formulae CY204 to CY217.

14. An electronic apparatus comprising the light-emitting device of claim 1 and a thin-film transistor,
wherein the thin-film transistor comprises a source electrode and a drain electrode, and the anode of the light-emitting device is electrically coupled to one selected from the source electrode and the drain electrode of the thin-film transistor.

15. The electronic apparatus of claim 14, further comprising a color filter, a color conversion layer, a touch screen layer, a polarizing layer, or any combination thereof.

16. A light-emitting device comprising:
an anode;
a cathode;

an interlayer comprising an emission layer between the anode and the cathode; and a hole transport region between the anode and the emission layer, wherein the hole transport region comprises a first layer and a second layer, the first layer is between the anode and the second layer, the first layer comprises a first compound, the second layer comprises a second compound, and a charge mobility of the first compound is lower than a charge mobility of the second compound, and wherein the first compound is selected from compounds of Group I:

Group I

1

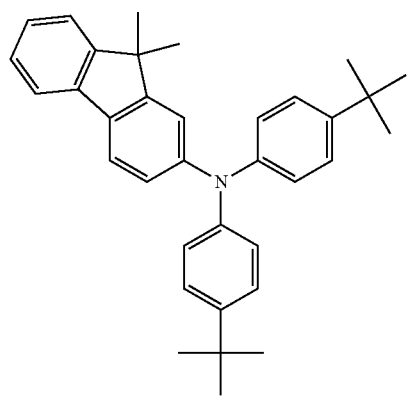

2

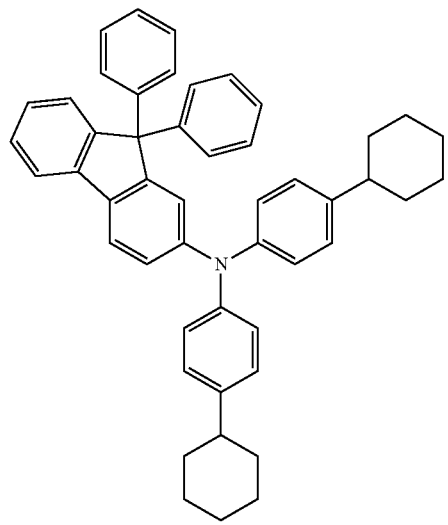

-continued

3

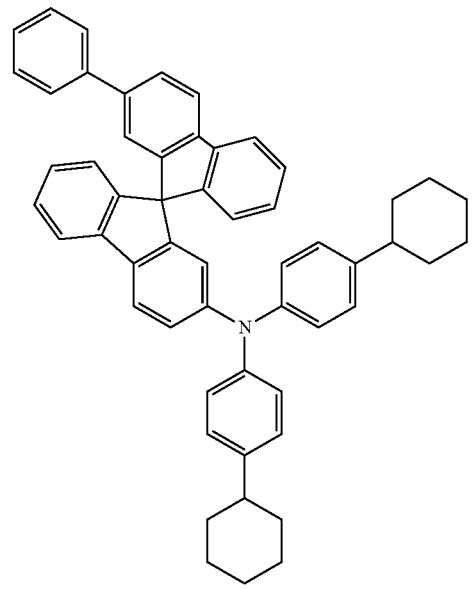

4

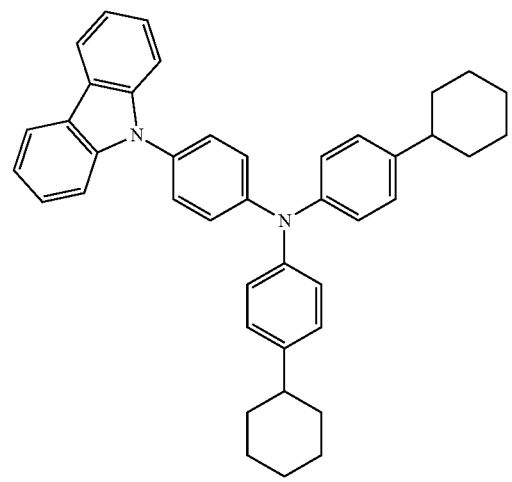

5

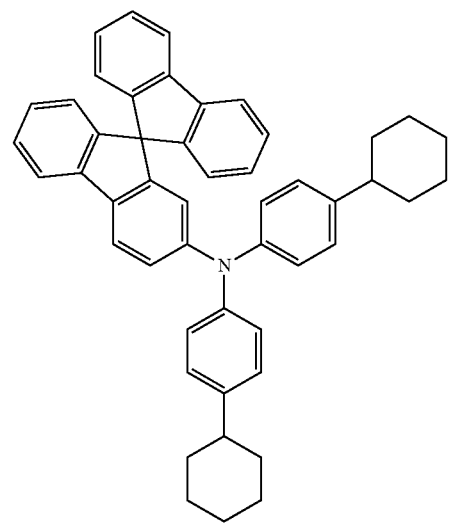

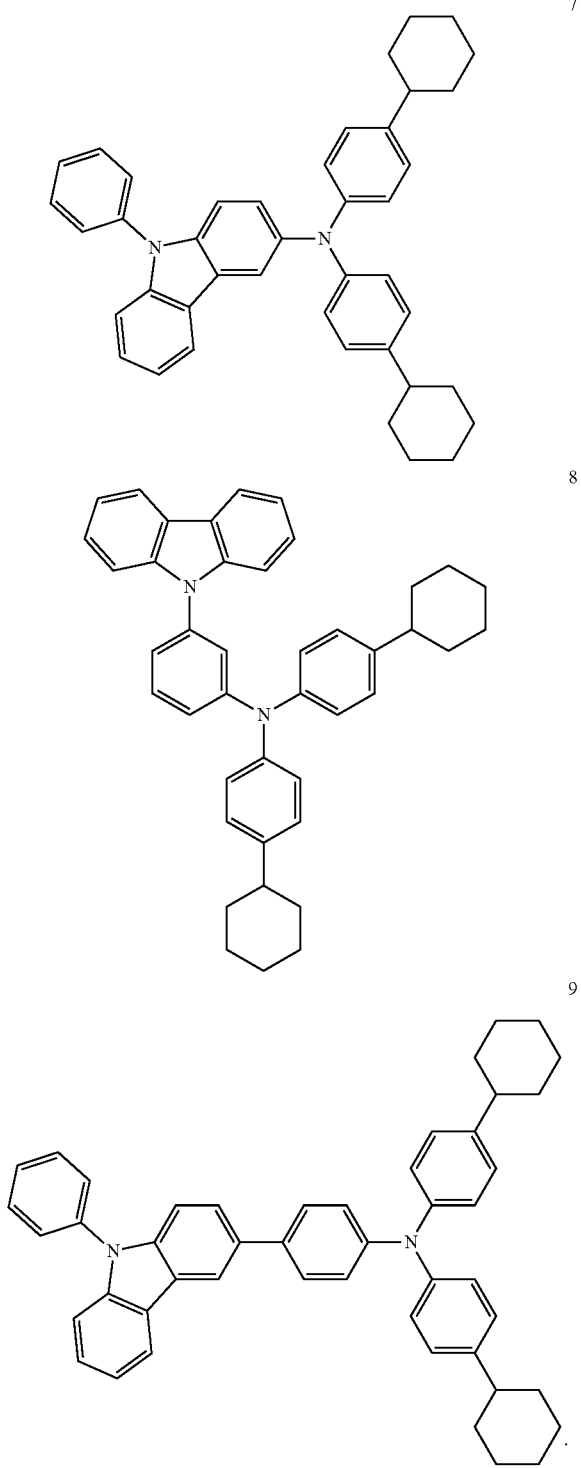

17. A light-emitting device comprising:
a substrate partitioned into a first subpixel area, a second subpixel area, and a third subpixel area;
a plurality of anodes respectively in the first subpixel area, the second subpixel area, and the third subpixel area of the substrate;
a cathode facing the plurality of anodes; and
an interlayer comprising an emission layer and a hole transport region, the emission layer being between the plurality of anodes and the cathode, and the hole transport region being between the plurality of anodes and the emission layer,
wherein the hole transport region comprises a first layer and a second layer,
the first layer comprises a first compound represented by Formula 1,
the second layer comprises a second compound, and
the first compound and the second compound are different from each other:

Formula 1

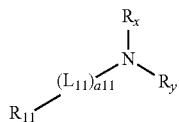

wherein, in Formula 1,
$L_{11}$ is a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$,
a11 is an integer from 0 to 5,
$R_x$ and $R_y$ are each a group represented by Formula 2, and $R_x$ and $R_y$ are identical to each other, Formula 2

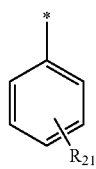

wherein, in Formula 2,
$R_{21}$ is a cyclopentyl group, a cyclohexyl group, a tert-butyl group, or a $C_5$-$C_{10}$ alkyl group, and
$R_{10a}$ is:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with -D, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —C($Q_{11}$)($Q_{12}$)($Q_{13}$), —B($Q_{11}$)($Q_{12}$), —N($Q_{11}$)($Q_{12}$), —P($Q_{11}$)($Q_{12}$), —C(=O)($Q_{11}$), —S(=O)($Q_{11}$), —S(=O)$_2$($Q_{11}$), —P(=O)($Q_{11}$)($Q_{12}$), —P(=S)($Q_{11}$)($Q_{12}$), or any combination thereof;
a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with -D, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —C($Q_{21}$)($Q_{22}$)($Q_{23}$), —B($Q_{21}$)($Q_{22}$), —N($Q_{21}$)($Q_{22}$), —P($Q_{21}$)($Q_{22}$), —C(=O)($Q_{21}$), —S(=O)($Q_{21}$), —S(=O)$_2$($Q_{21}$), —P(=O)($Q_{21}$)($Q_{22}$) or —P(=S)($Q_{21}$)($Q_{22}$), or any combination thereof; or —Si(Q$_{31}$)(Q$_{32}$)(Q$_{33}$), —C(Q$_{31}$)(Q$_{32}$)(Q$_{33}$), —B(Q$_{31}$)(Q$_{32}$), —N(Q$_{31}$)(Q$_{32}$), —P(Q$_{31}$)(Q$_{32}$), —C(=O)(Q$_{31}$), —S(=O)(Q$_{31}$), —S(=O)$_2$(Q$_{31}$), —P(=O)(Q$_{31}$)(Q$_{32}$), or —P(=S)(Q$_{31}$)(Q$_{32}$), wherein Q$_{11}$ to Q$_{13}$, Q$_{21}$ to Q$_{23}$, and Q$_{31}$ to Q$_{33}$ are each independently: hydrogen; -D; —F; —Cl; —Br; —I; a hydroxyl group; a cyano group; a nitro group; a C$_1$-C$_{60}$ alkyl group; a C$_2$-C$_{60}$ alkenyl group; a C$_2$-C$_{60}$ alkynyl group; a C$_1$-C$_{60}$ alkoxy group; or a C$_3$-C$_{60}$ carbocyclic group or a C$_1$-C$_{60}$ heterocyclic group, each unsubstituted or substituted with -D, —F, a cyano group, a C$_1$-C$_{60}$ alkyl group, a C$_1$-C$_{60}$ alkoxy group, a phenyl group, a biphenyl group, or any combination thereof,

* indicates a binding site to a neighboring atom, and wherein R$_{11}$ is a group represented by one selected from Formulae 6-1 to 6-173:

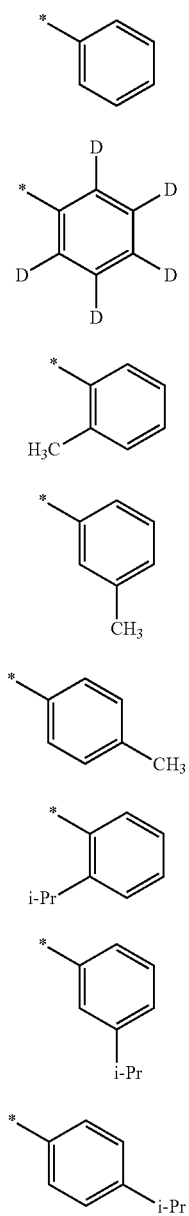

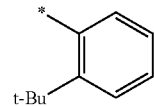
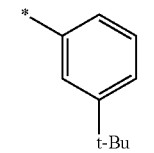
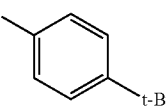
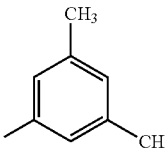
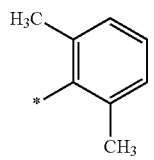
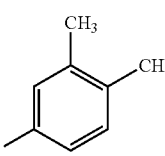
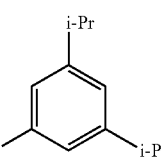
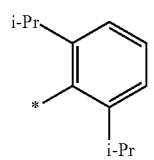
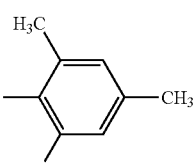
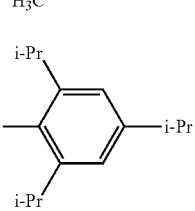

| 203 -continued | | 204 -continued | |
|---|---|---|---|
| 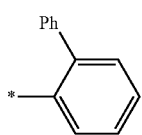 | 6-19 | 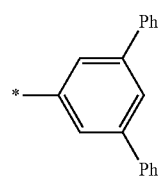 | 6-28 |
| 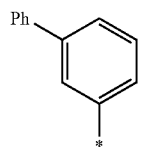 | 6-20 | 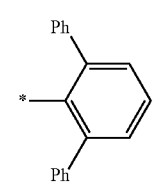 | 6-29 |
| 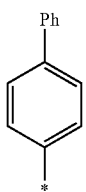 | 6-21 | 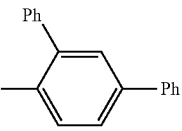 | 6-30 |
| 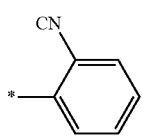 | 6-22 | 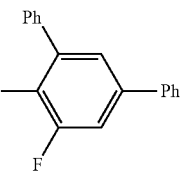 | 6-31 |
| 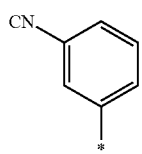 | 6-23 | 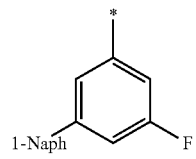 | 6-32 |
| 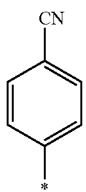 | 6-24 | 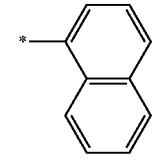 | 6-33 |
| 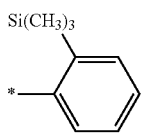 | 6-25 | 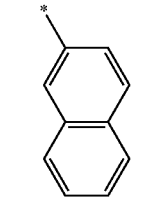 | 6-34 |
| 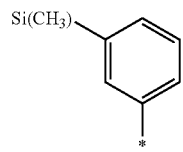 | 6-26 | 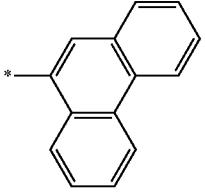 | 6-35 |
| 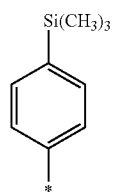 | 6-27 | | |

| | |
|---|---|
| 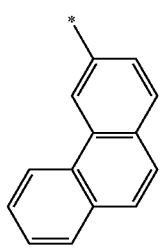 | 6-36 |
| 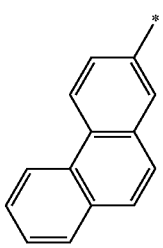 | 6-37 |
| 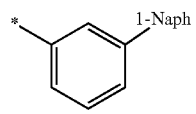 | 6-38 |
| 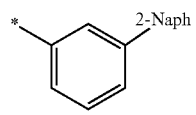 | 6-39 |
| 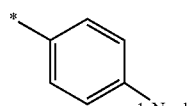 | 6-40 |
| 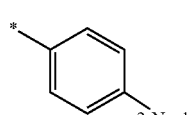 | 6-41 |
| 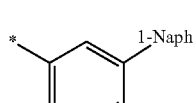 | 6-42 |
| 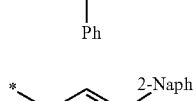 | 6-43 |
| 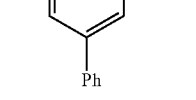 | 6-44 |
| 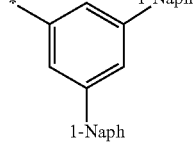 | |
| | |
|---|---|
| 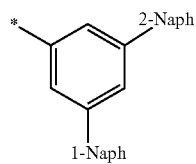 | 6-45 |
| 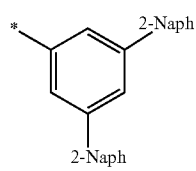 | 6-46 |
| 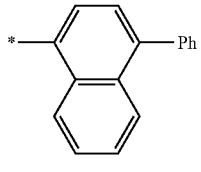 | 6-47 |
| 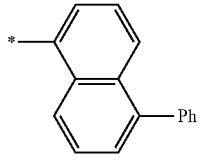 | 6-48 |
| 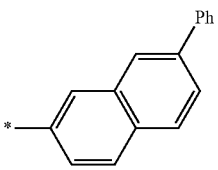 | 6-49 |
| 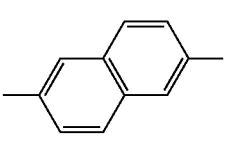 | 6-50 |
| 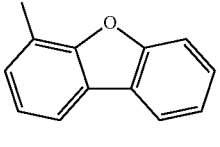 | 6-51 |
| 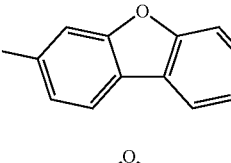 | 6-52 |
| 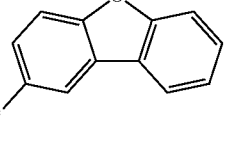 | 6-53 |
| 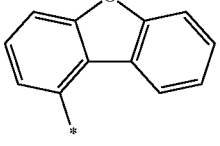 | 6-54 |

| | |
|---|---|
| 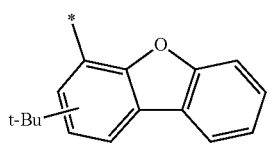 6-55 | 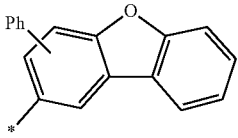 6-65 |
| 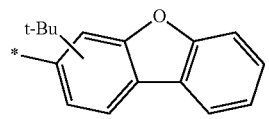 6-56 | 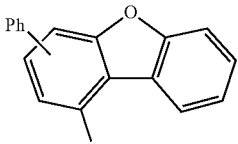 6-66 |
| 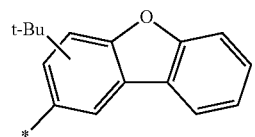 6-57 | |
| 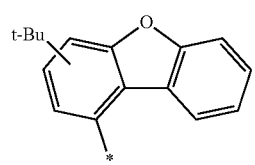 6-58 | 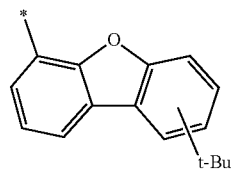 6-67 |
| 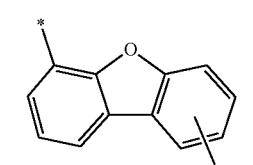 6-59 | 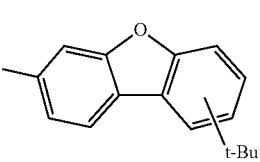 6-68 |
| 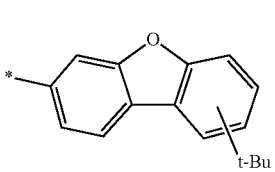 6-60 | 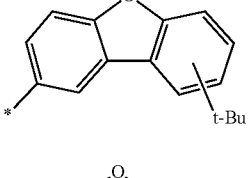 6-69 |
| 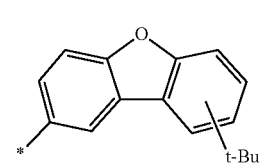 6-61 | 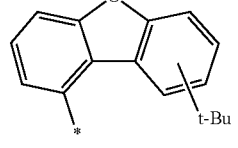 6-70 |
| 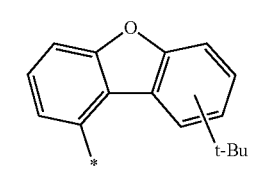 6-62 | 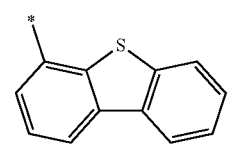 6-71 |
| 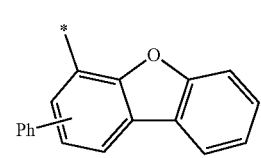 6-63 | 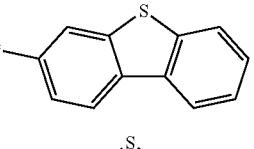 6-72 |
| 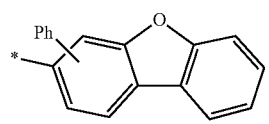 6-64 | 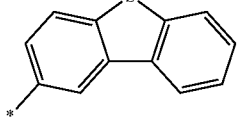 6-73 |

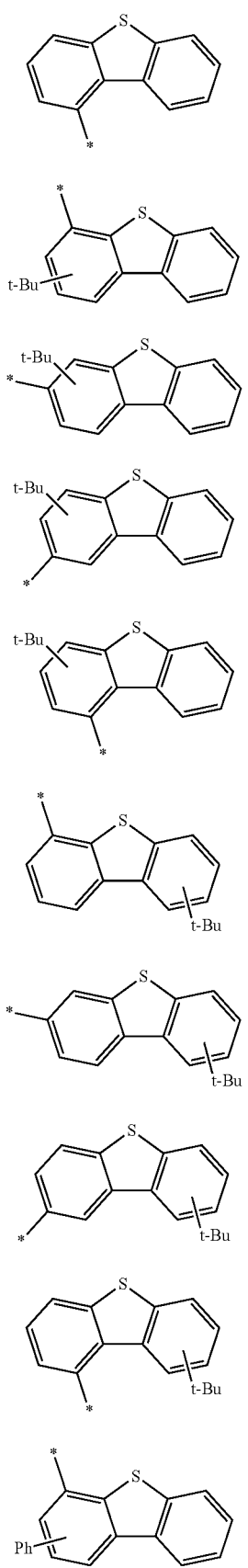
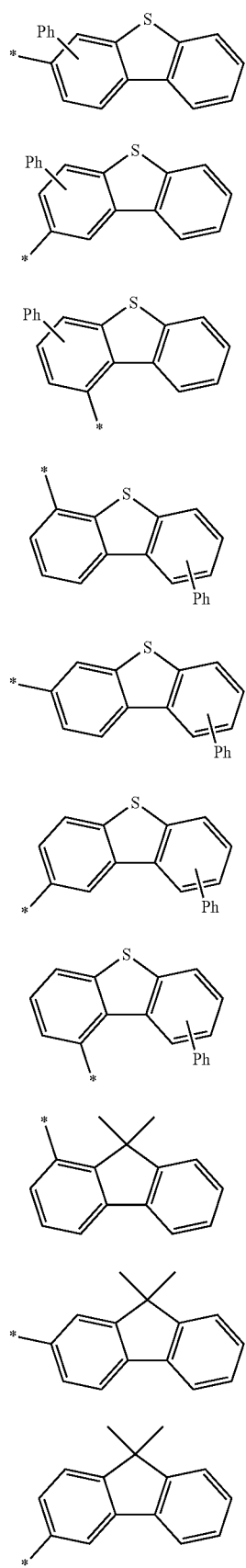

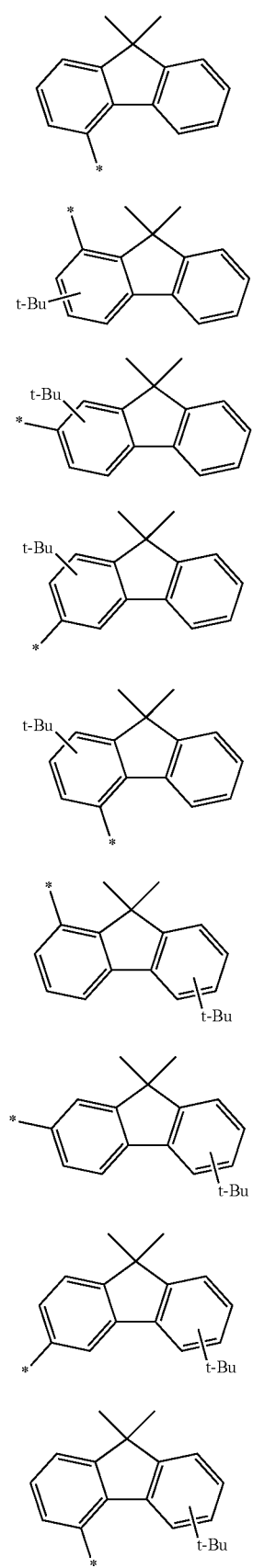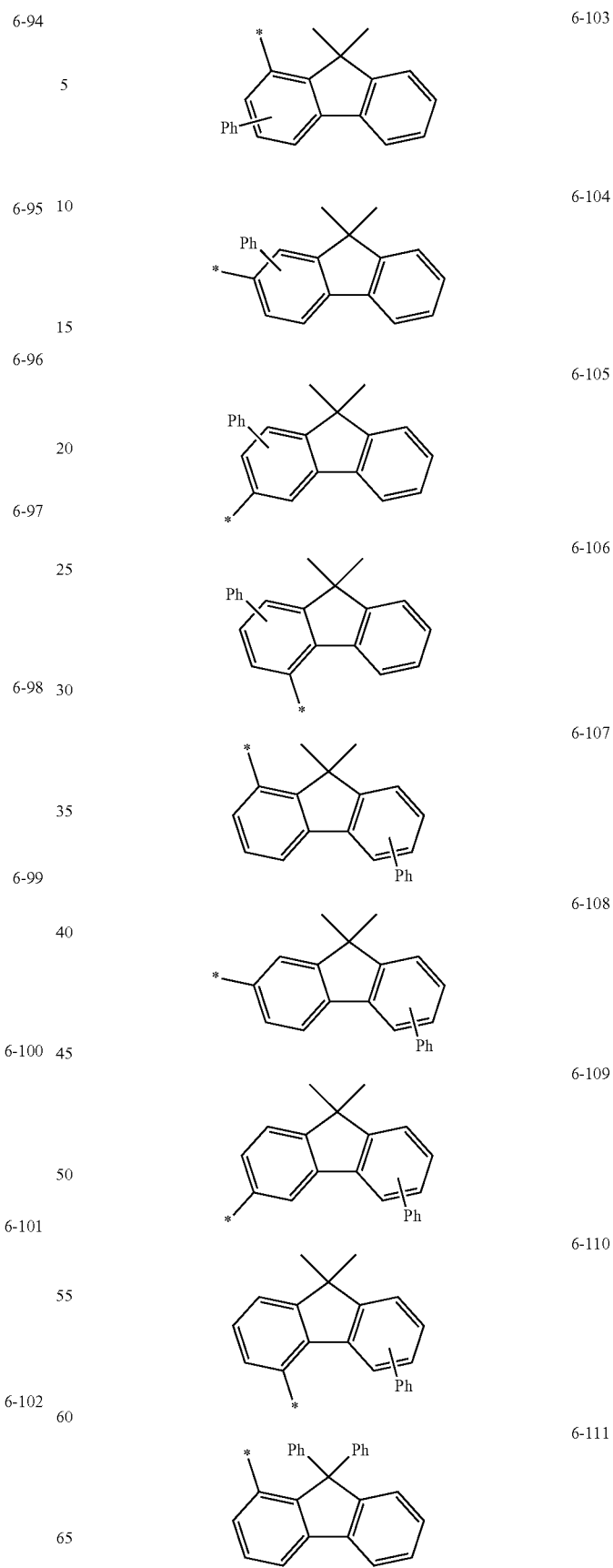

-continued
6-112 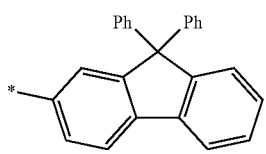
6-113 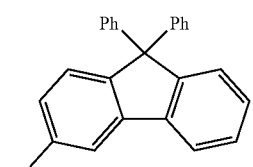
6-114 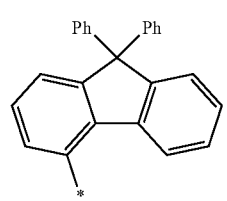
6-115 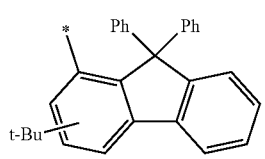
6-116 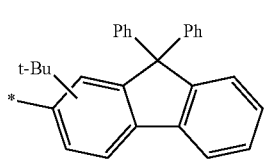
6-117 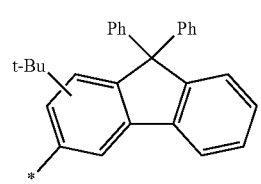
6-118 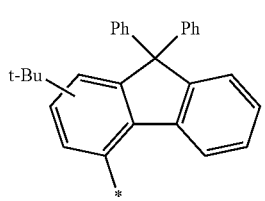
6-119 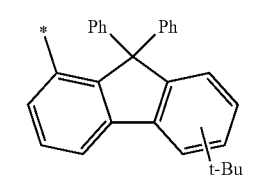
6-120 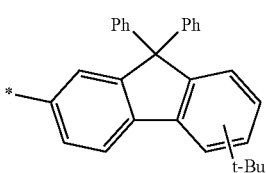
-continued
6-121 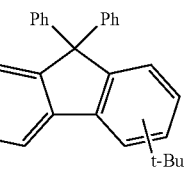
6-122 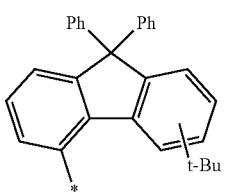
6-123 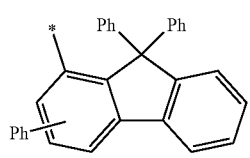
6-124 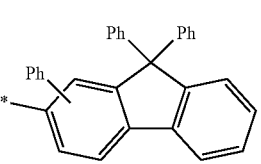
6-125 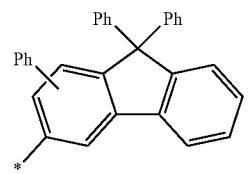
6-126 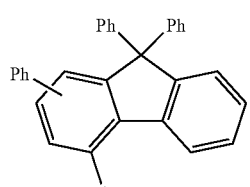
6-127 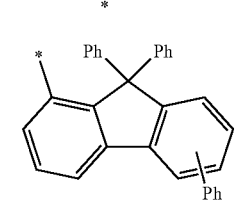
6-128 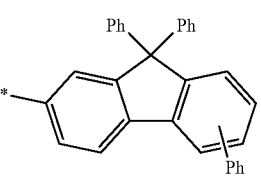
6-129 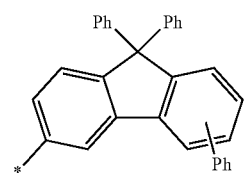

-continued 6-130

6-131

6-132

6-133

6-134

6-135

6-136

6-137

-continued 6-138

6-139

6-140

6-141

6-142

6-143

6-144

6-145

| 6-146 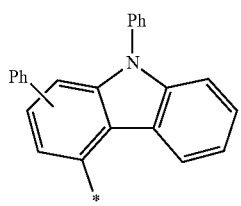 | 6-154 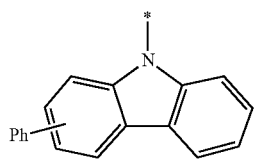 |
| --- | --- |
| 6-147 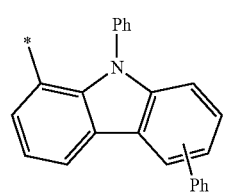 | 6-155 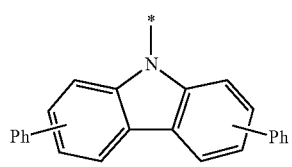 |
| 6-148 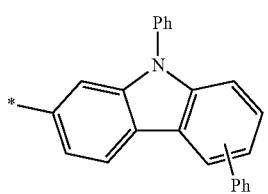 | 6-156 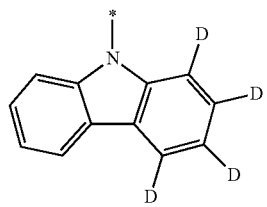 |
| 6-149 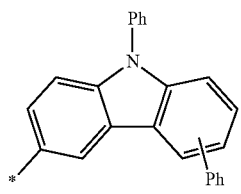 | 6-157 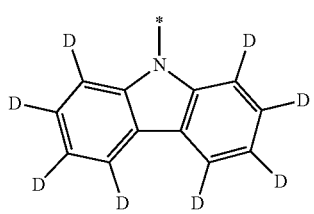 |
| 6-150 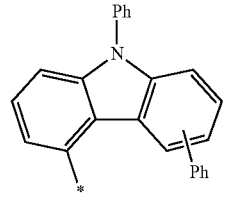 | 6-158 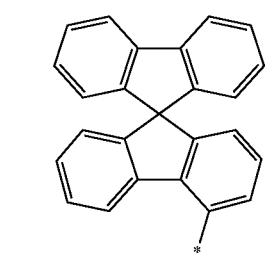 |
| 6-151 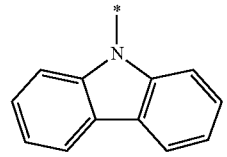 | 6-159 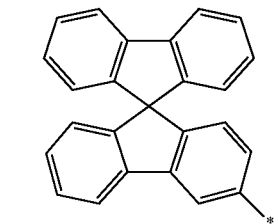 |
| 6-152 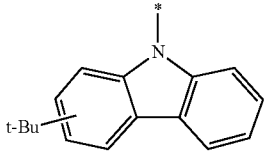 | 6-160 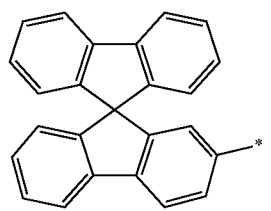 |
| 6-153 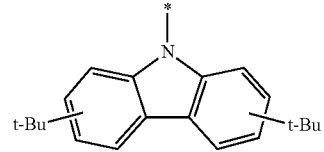 | |

-continued
6-161
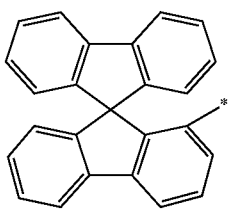
6-162
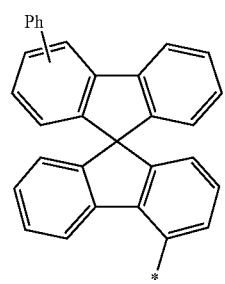
6-163
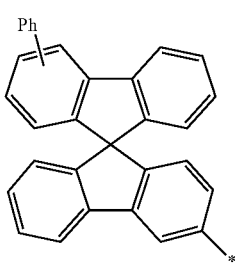
6-164
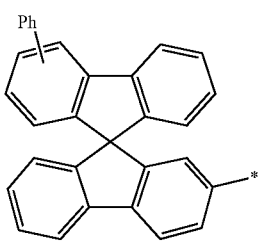
6-165
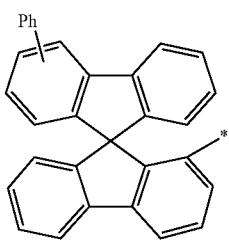
6-166
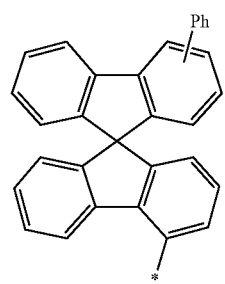
-continued
6-167
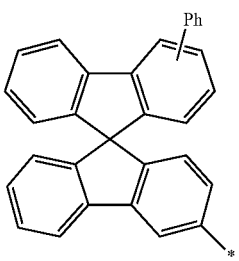
6-168
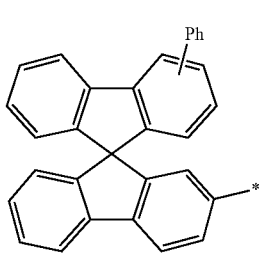
6-169
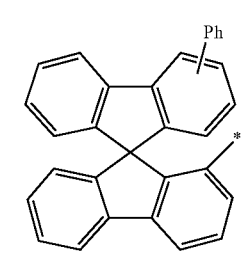
6-170
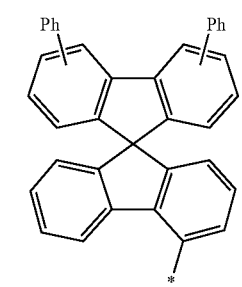
6-171
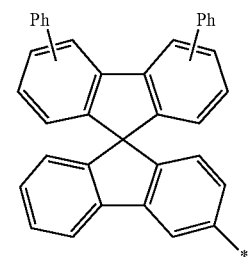
6-172
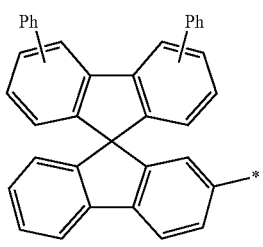

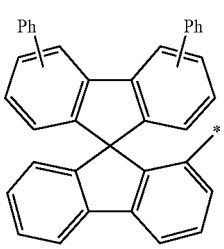

6-173 wherein, in Formulae 6-1 to 6-173,
i-Pr is an isopropyl group;
t-Bu is a tert-butyl group;
Ph is a phenyl group;
1-Naph is an 1-naphthyl group;
2-Naph is a 2-naphthyl group; and
* indicates a binding site to a neighboring atom, and
wherein when $R_{11}$ is represented by one selected from Formulae 5-10 to 5-13 and $X_{51}$ is $C(R_{53})(R_{54})$ and $R_{53}$ and $R_{54}$ are each independently a $C_1$-$C_{20}$ alkyl group, then $R_{21}$ is a tert-butyl group, wherein b54 is an integer from 1 to 4, b55 is an integer from 1 to 3, and $R_{51}$ and $R_{52}$ are each independently hydrogen, -D, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one phenyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a naphthyl group, a fluorenyl group, a spiro-bifluorenyl group, a spiro-fluorene-benzofluorenyl group, a benzofluorenyl group, a dibenzofluorenyl group, a phenalenyl group, a phenanthrenyl group, an anthracenyl group, a fluoranthenyl group, a triphenylenyl group, a pyridinyl group, a pyrimidinyl group, a pyrazinyl group, a triazinyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a dibenzofuranyl group, a dibenzothiophenyl group, a dibenzosilolyl group, —Si($Q_{31}$)($Q_{32}$)($Q_{33}$), —C($Q_{31}$)($Q_{32}$)($Q_{33}$), —N($Q_{31}$)($Q_{32}$), or —B($Q_{31}$)($Q_{32}$),

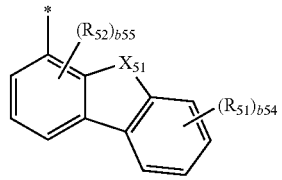

5-10

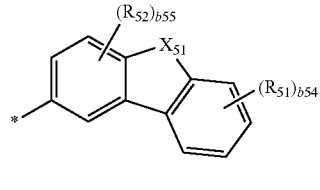

5-11

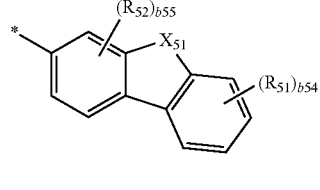

5-12

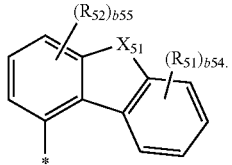

5-13

* * * * *